United States Patent [19]

Alpins

[11] Patent Number: 5,975,084

[45] Date of Patent: Nov. 2, 1999

[54] METHOD FOR SURGICALLY ACHIEVING MINIMUM ASTIGMATISM MEASURED REFRACTIVELY AND TOPOGRAPHICALLY

[76] Inventor: Noel A. Alpins, 7 Chesterville Road, Cheltenham, Victoria 3192, Australia

[21] Appl. No.: 09/063,678

[22] Filed: Apr. 21, 1998

Related U.S. Application Data

[63] Continuation of application No. 08/476,449, Jun. 7, 1995, Pat. No. 5,740,815.

[51] Int. Cl.⁶ .................................................... A61B 19/00
[52] U.S. Cl. ............................................... 128/897; 606/5
[58] Field of Search ...................... 128/897–98; 623/4–6; 606/204.25, 4–6

[56] References Cited

U.S. PATENT DOCUMENTS

| | | |
|---|---|---|
| 3,947,097 | 3/1976 | Humphrey . |
| 4,718,418 | 1/1988 | L'Esperance . |
| 4,721,379 | 1/1988 | L'Esperance . |
| 5,102,409 | 4/1992 | Balgorod . |
| 5,190,057 | 3/1993 | Sarfarazi . |

FOREIGN PATENT DOCUMENTS

| | | |
|---|---|---|
| 247260 | 12/1987 | European Pat. Off. . |
| 257836 | 12/1988 | European Pat. Off. . |
| 296982 | 12/1988 | European Pat. Off. . |

OTHER PUBLICATIONS

Cravy, T.V. "Calculation of the Change . . . " Ophthalmic Surgery, vol. 10, No. 1, Jan. 1979, pp. 38–49.

Jaffe, N.S. et al. "The Pathophysiology of Corneal Astigmatism . . . " Trans Am Acad. Opthaalmoi Otolaryngol, vol. 79, 1975 pp. 615–630.

*Primary Examiner*—John P. Lacyk
*Attorney, Agent, or Firm*—Ladas & Parry

[57] ABSTRACT

A method of surgically treating an eye of a patient to correct astigmatism in which values of astigmatism are measured topographically and refractively, and limit values of targeted induced astigmatism for the topographically and refractively measured astigmatism values are obtained by summating the topographically value of astigmatism with the refractive value of astigmatism and vice versa. Respective target values of astigmatism for refraction and topography based on the limit values are obtained and surgical treatment is effected with a target induced astigmatism which is intermediate the limit values and provided respective topographical and refractive non-zero target astigmatism values whose sum is a minimum.

30 Claims, 44 Drawing Sheets

| ASTIGMATISM | | |
|---|---|---|
| | | EXAMPLE |
| PRE OP | $K_1$ Ax $\theta_1$ | 4.00 Ax 20 |
| AIMED | $K_2$ Ax $\theta_2$ | 0.75 Ax 70 |
| ACHIEVED | $K_3$ Ax $\theta_3$ | 1.25 Ax 125 |
| ANGLE OF CORRECTION | $\theta_3 - \theta_2$ | +55 |

DOUBLE ANGLE VECTOR DIAGRAM

SURGICAL VECTORS

| SURGICAL VECTORS | | |
|---|---|---|
| | | EXAMPLE |
| AIMED INDUCED ASTIGMATISM (AIA) | $K_{12}$ | 4.20 Ax 105 |
| SURGICALLY INDUCED ASTIGMATISM (AIA) | $K_{13}$ | 5.12 Ax 114 |
| DIFFERENCE | $K_{32}$ | 1.66 Ax 48 |

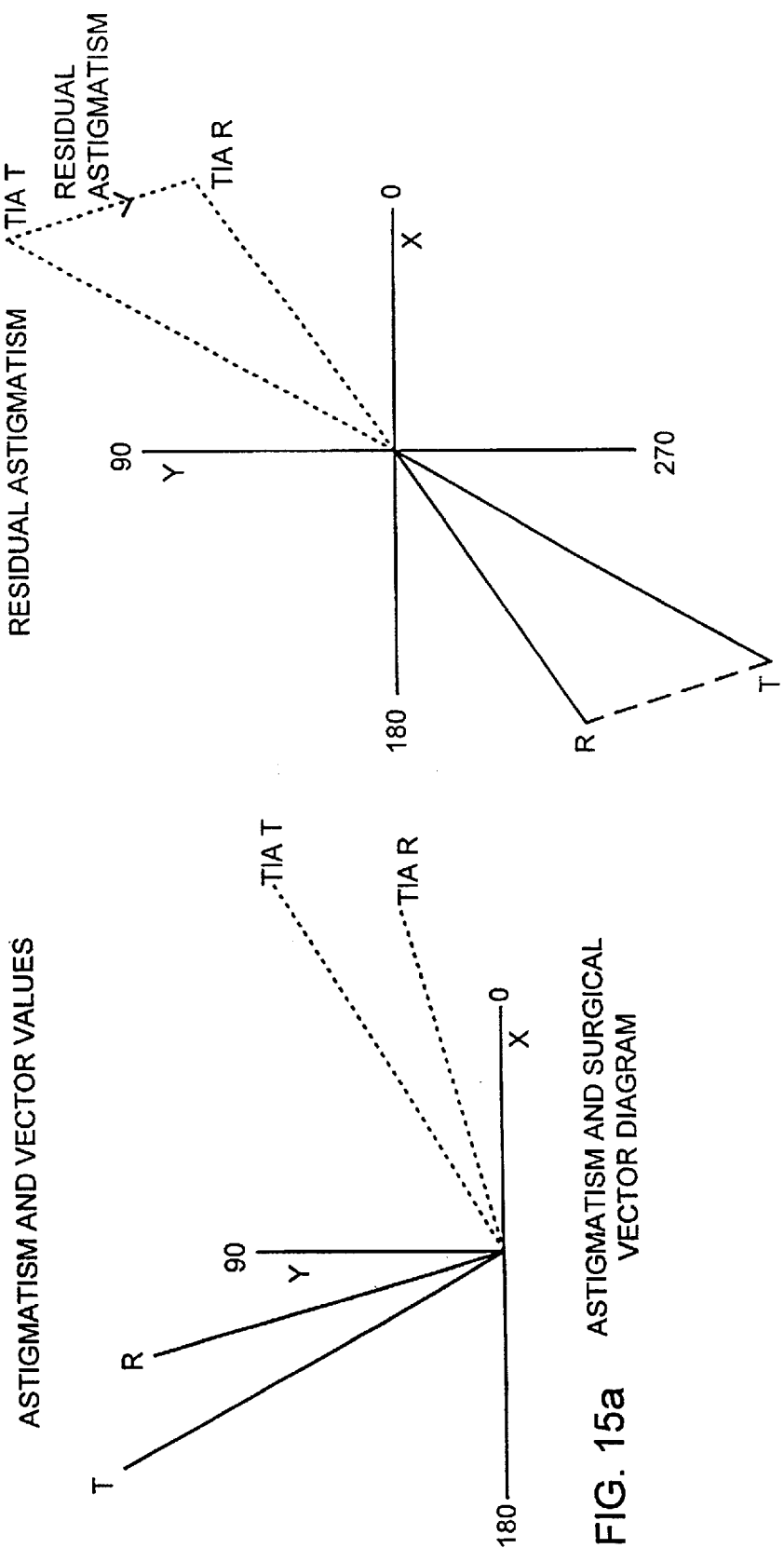

TREATMENT BY TOPOGRAPHY
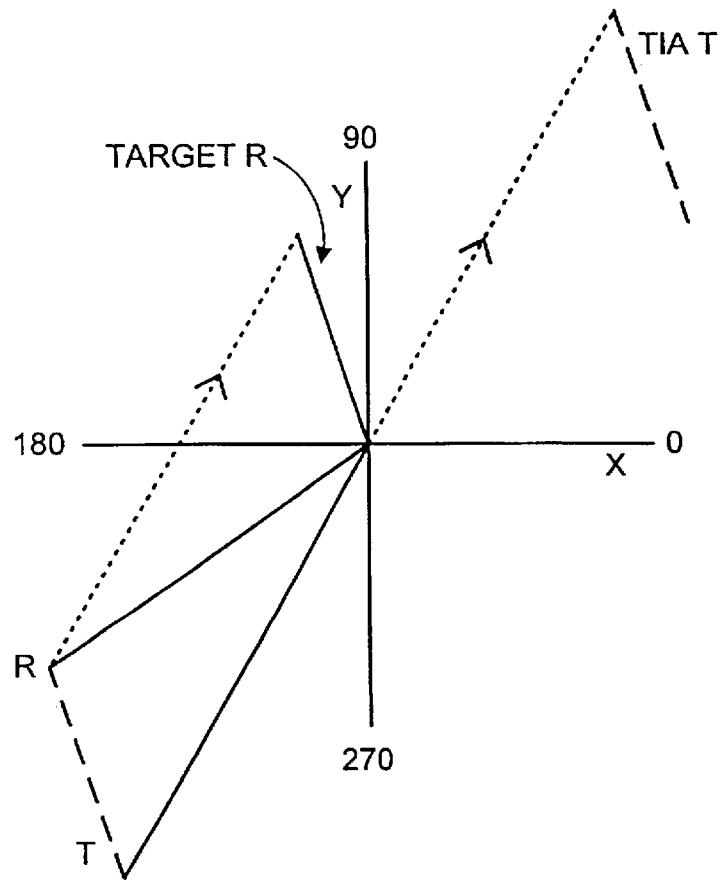
| | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | | 1.70 Ax 30 | |
| TARGET | 0.00 Ax | +0.76 Ax 57 | -0.76 Ax 147 |
| EMPHASIS | 100% | 0% | |
FIG. 16a DOUBLE ANGLE VECTOR DIAGRAM TREATMENT BY REFRACTION
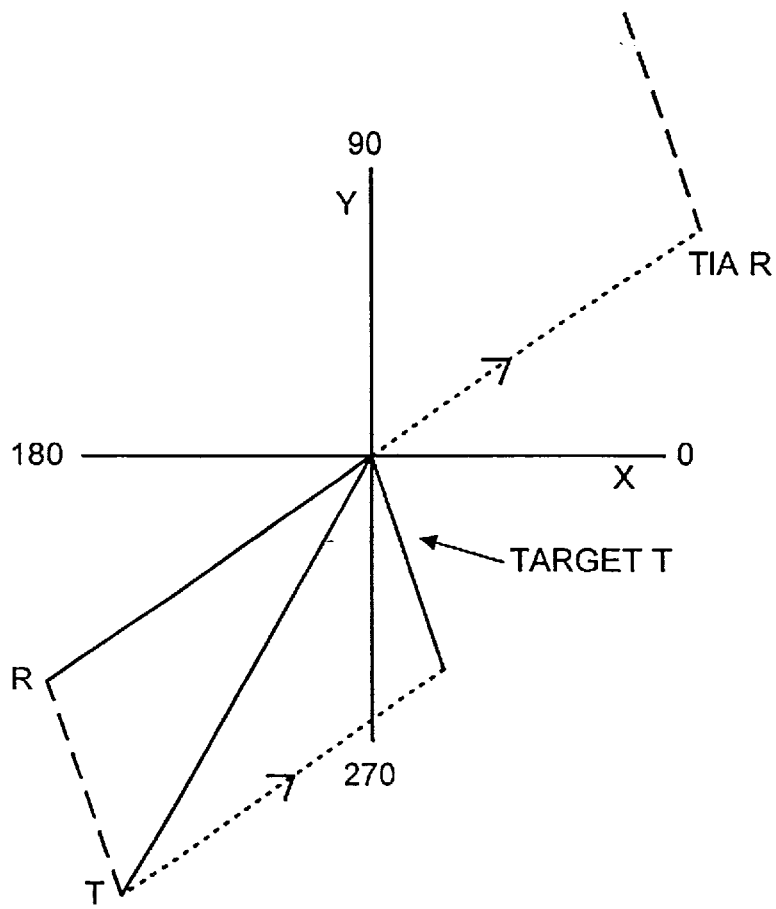
| | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | | 1.40 Ax 17 | |
| TARGET | 0.76 Ax 147 | 0.00 Ax | 0.00 Ax |
| EMPHASIS | 0% | 100% | |
FIG. 16b DOUBLE ANGLE VECTOR DIAGRAM

TREATMENT BY INTERMEDIATE TIA FOR MINIMUM TARGET ASTIGMATISM
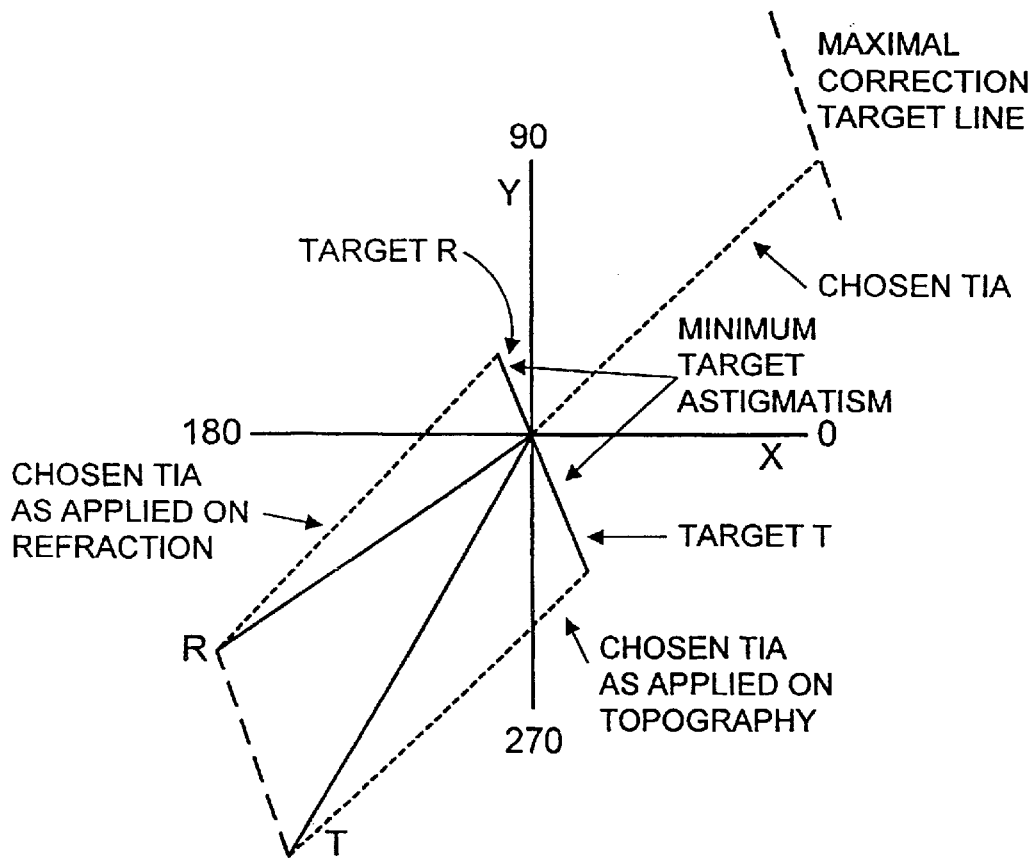
|  | TOPOGRAPHY | PLUS CYLINDER REFRACTION | MINUS CYLINDER REFRATION |
|---|---|---|---|
| PREOP | 1.70 Ax 120 | +1.40 Ax 107 | -1.40 Ax 17 |
| TIA | | 1.47 Ax 22 | |
| TARGET | 0.50 Ax 147 | +0.26 Ax 57 | -0.26 Ax 147 |
| EMPHASIS | 34% | 66% | |
FIG. 17a DOUBLE ANGLE VECTOR DIAGRAM

TREATMENT BY OPTIMAL TIA
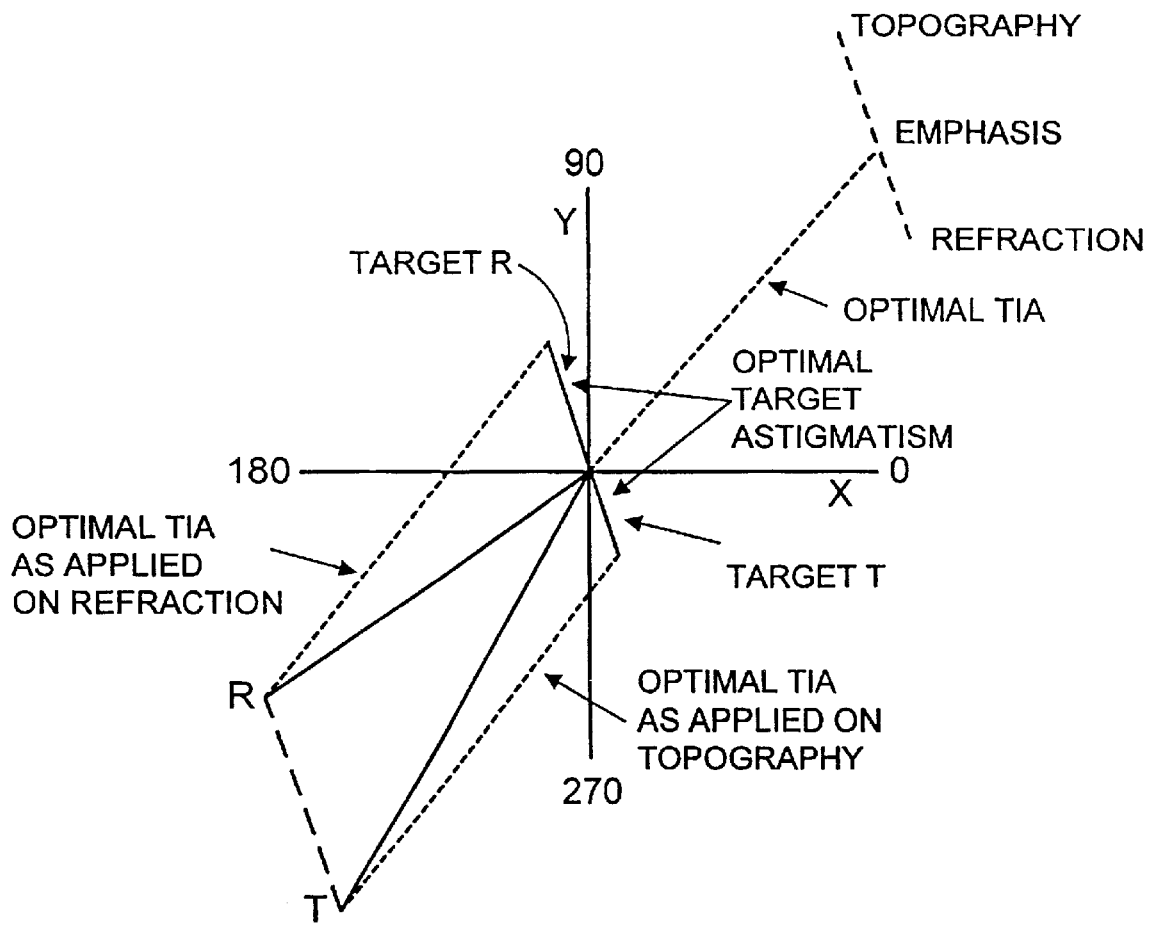
|  | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA |  | 1.56 Ax 26 | |
| TARGET | 0.28 Ax 147 | +0.48 Ax 57 | -0.48 Ax 147 |
| EMPHASIS | 63% | 37% | |
FIG. 17b  DOUBLE ANGLE VECTOR DIAGRAM TREATMENT BY TIA WITHOUT REGARD
TO MINIMUM TARGET ASTIGMATISM
eg. OVERCORRECTION
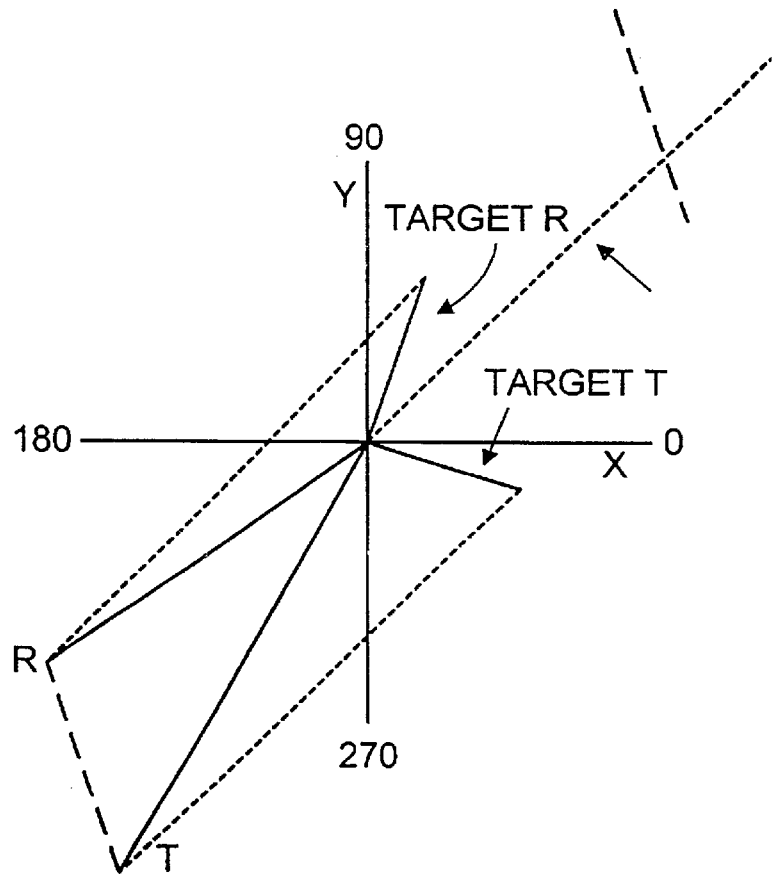
|  | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA |  | 1.90 Ax 22 |  |
| TARGET | 0.54 Ax 172 | +0.58 Ax 35 | -0.58 Ax 125 |
FIG. 18a DOUBLE ANGLE VECTOR DIAGRAM

TREATMENT BY TIA WITHOUT REGARD TO MINIMUM TARGET ASTIGMATISM
eg. UNDERCORRECTION
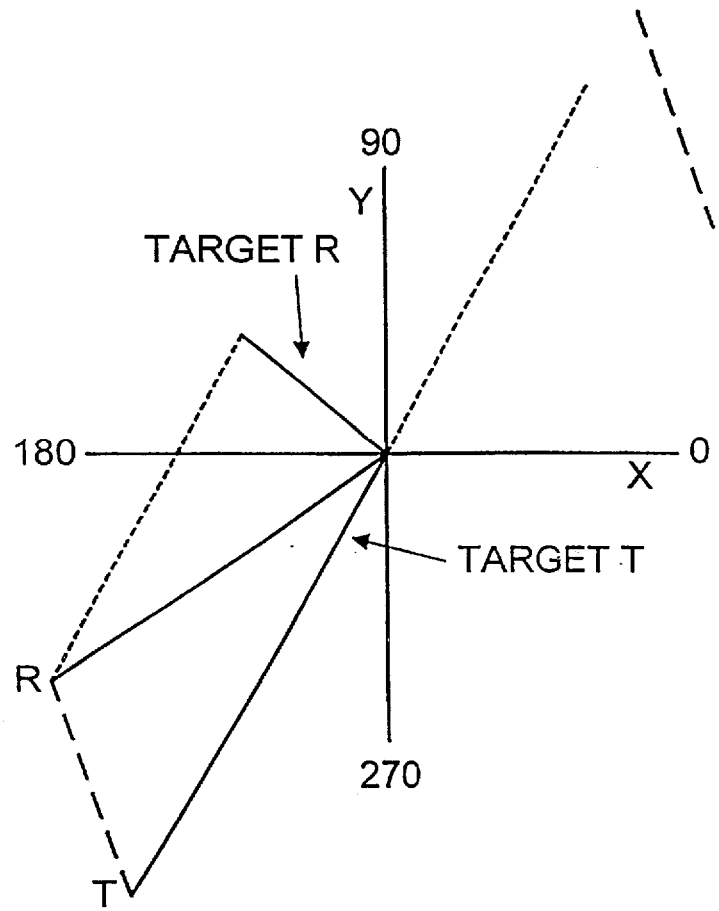
|  | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | 1.40 Ax 30 | | |
| TARGET | 0.30 Ax 120 | +0.63 Ax 69 | -0.63 Ax 159 |
FIG. 18b DOUBLE ANGLE VECTOR DIAGRAM

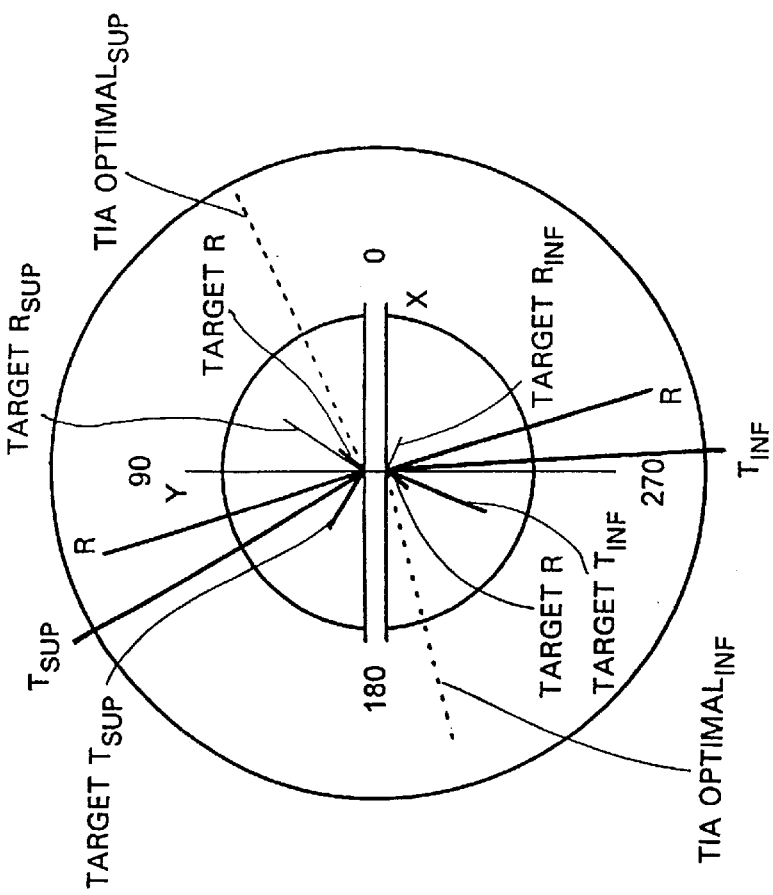

SUPERIOR

| | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | | 1.56 Ax 26 | |
| TARGET | 0.28 Ax 147 | (+0.48 Ax 57) | (-0.48 Ax 147) |
| EMPHASIS | 63% | | 37% |

RESOLVED TREATMENT VECTOR

| | PLUS CYLINDER REFRACTION | MINUS CYLINDER REFRACTION |
|---|---|---|
| PREOP | +1.40 Ax 107 | -1.40 Ax 17 |
| TIA Net | 1.47 Ax 20 | |
| TARGET | +0.16 Ax 52 | -0.16 Ax 142 |

INFERIOR

| | TOPOGRAPHY | PLUS CYLINDER REFRACTION | MINUS CYLINDER REFRACTION |
|---|---|---|---|
| PREOP | 1.70 Ax 274 | +1.40 Ax 107 | -1.40 Ax 17 |
| TIA | | 1.45 Ax 193 | |
| TARGET | 0.56 Ax 247 | (+0.20 Ax 157) | (-0.20 Ax 67) |
| EMPHASIS | 26% | | 74% |

THE TREATMENT OF IRREGULAR ASTIGMATISM BY APPLYING THE OPTIMAL TREATMENT SEPARATELY TO EACH CORNEAL HEMI-DIVISION

FIG. 20a. ASTIGMATISM AND SURGICAL VECTOR DIAGRAM

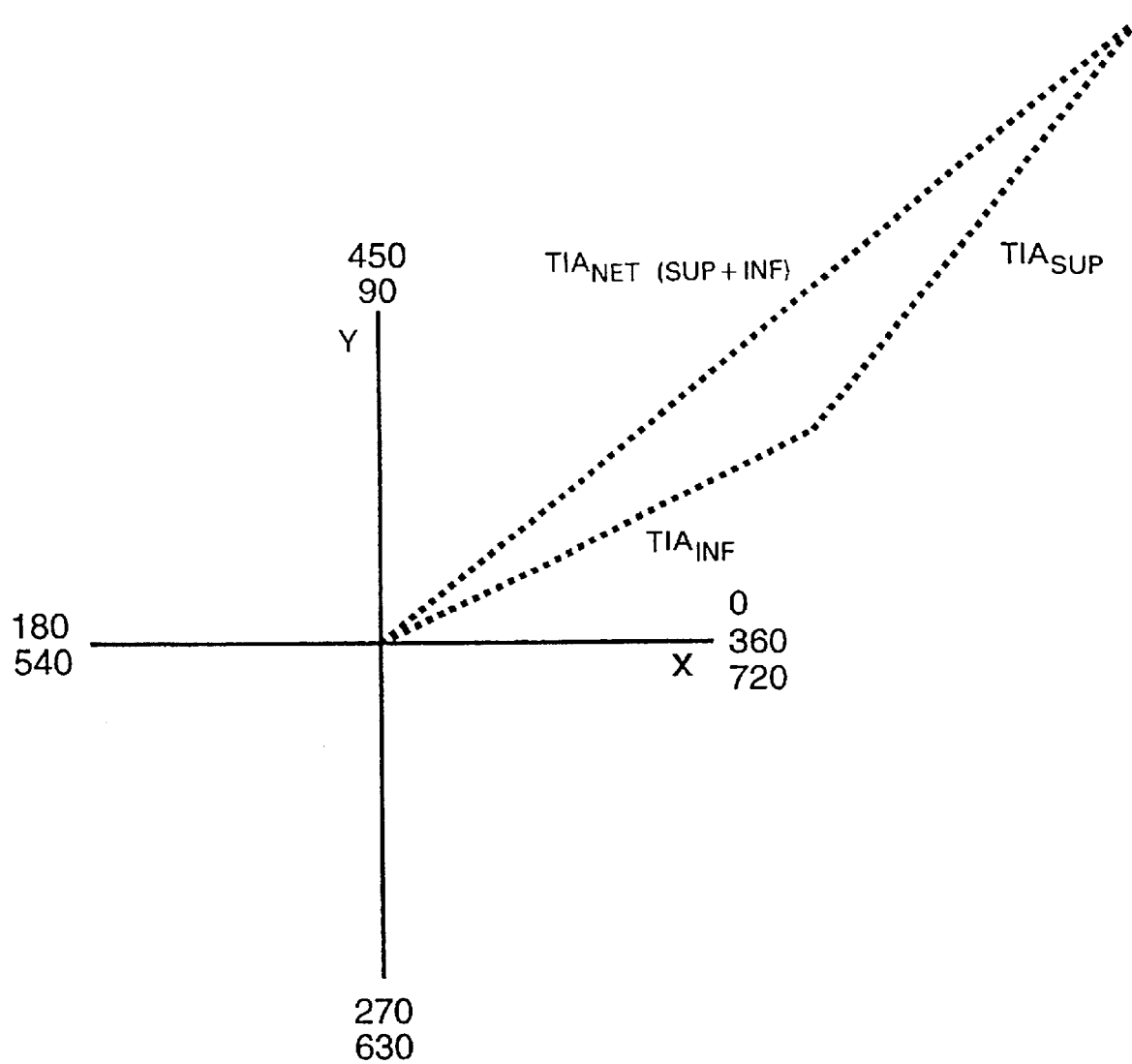
FIG. 20b DOUBLE VECTOR DIAGRAM

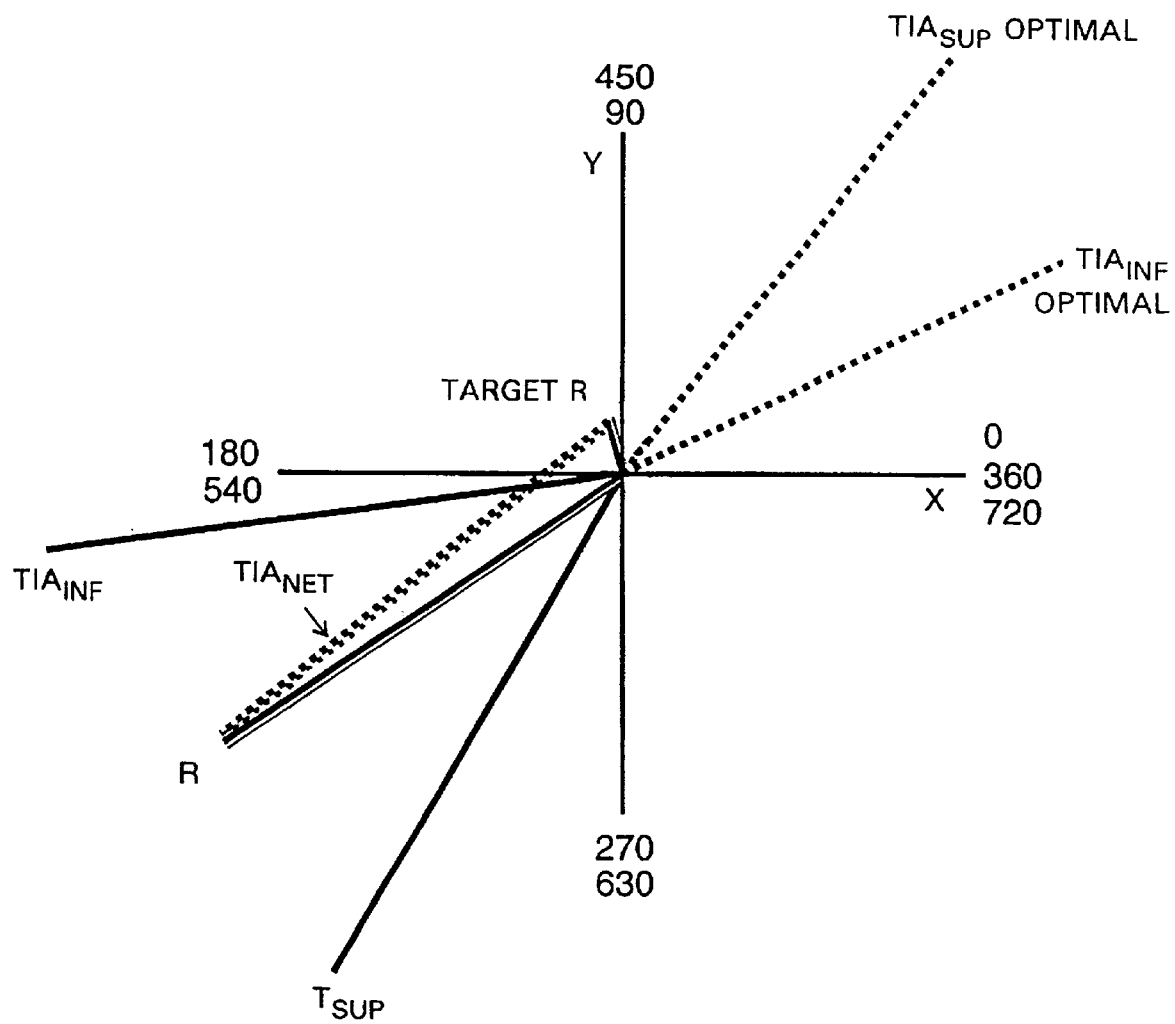
FIG. 20c DOUBLE ANGLE VECTOR DIAGRAM

ASTIGMATIC TORQUE
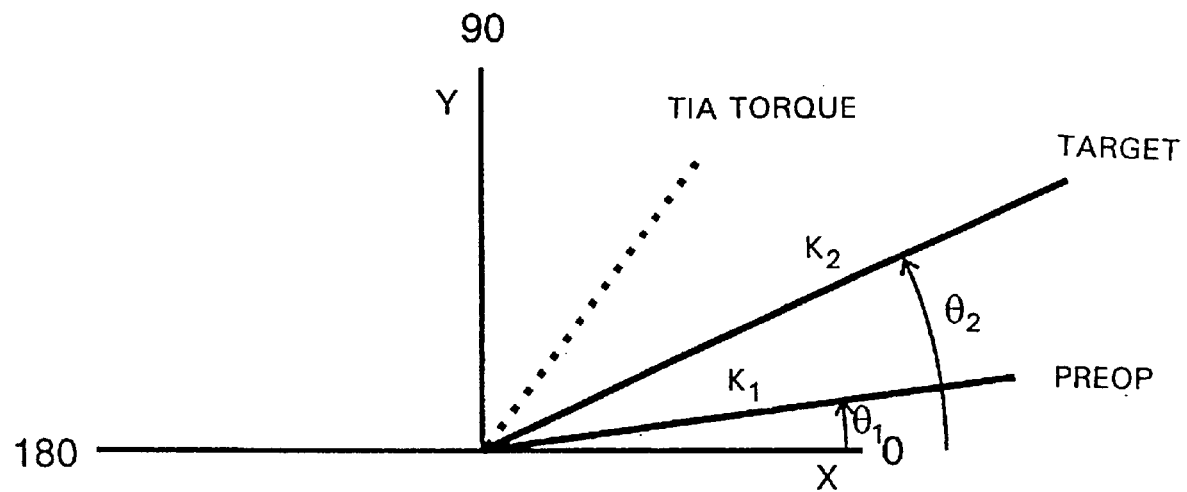
| ASTIGMATISM | |
|---|---|
| | EXAMPLE |
| PREOP | 1.40 AX 8 |
| TARGETED | 1.69 AX 25 |
FIG. 21a ASTIGMATISM AND SURGICAL VECTOR DIAGRAM

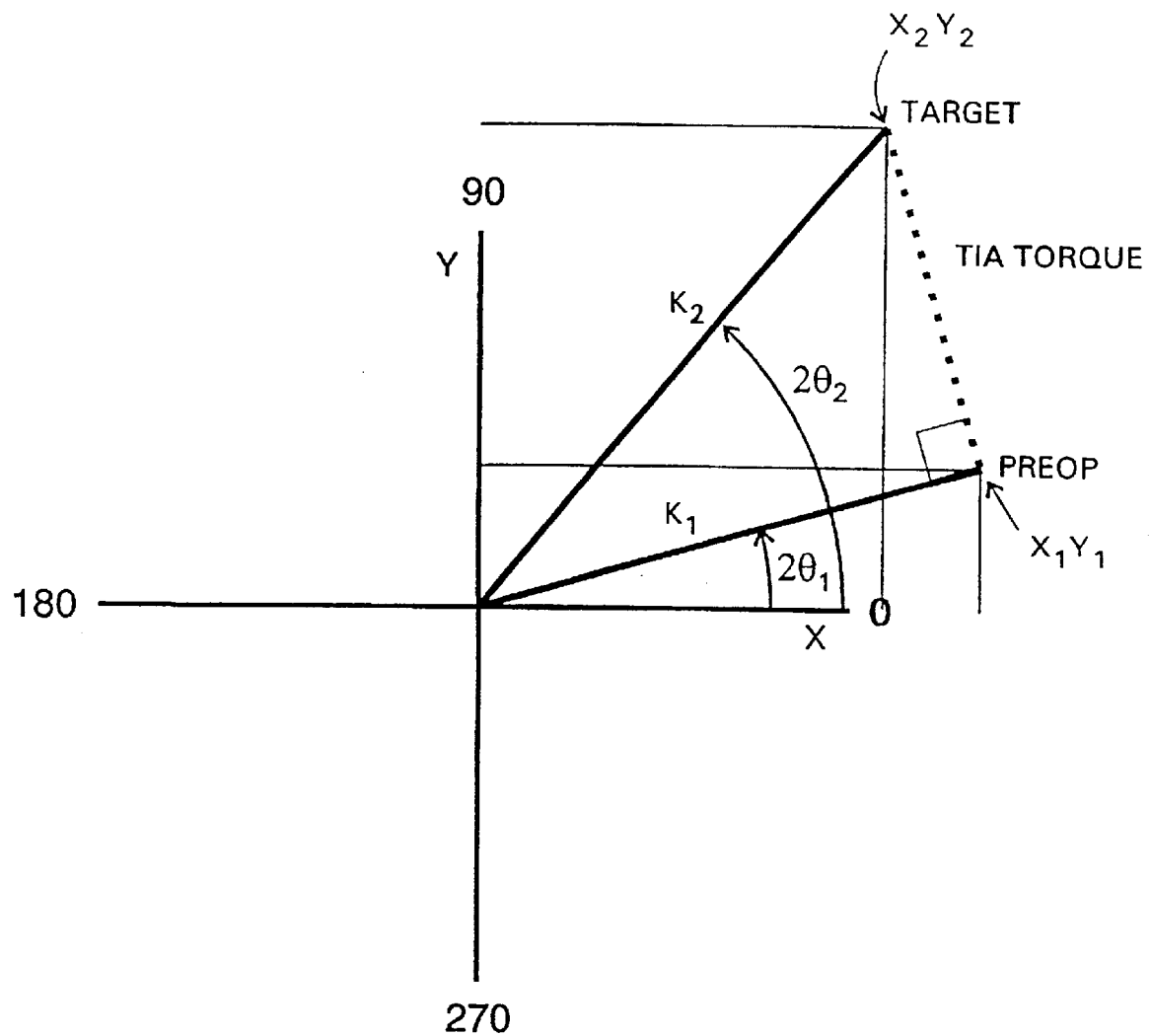
FIG. 21b DOUBLE ANGLE VECTOR DIAGRAM

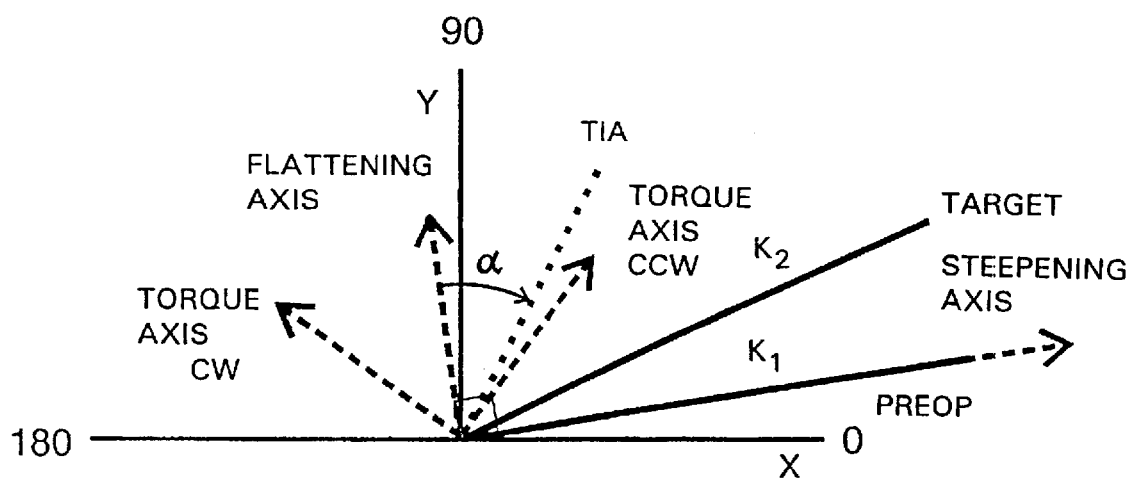
FIG. 22a ASTIGMATISM AND SURGICAL VECTOR DIAGRAM

TORQUE VS FLATTENING/STEEPENING
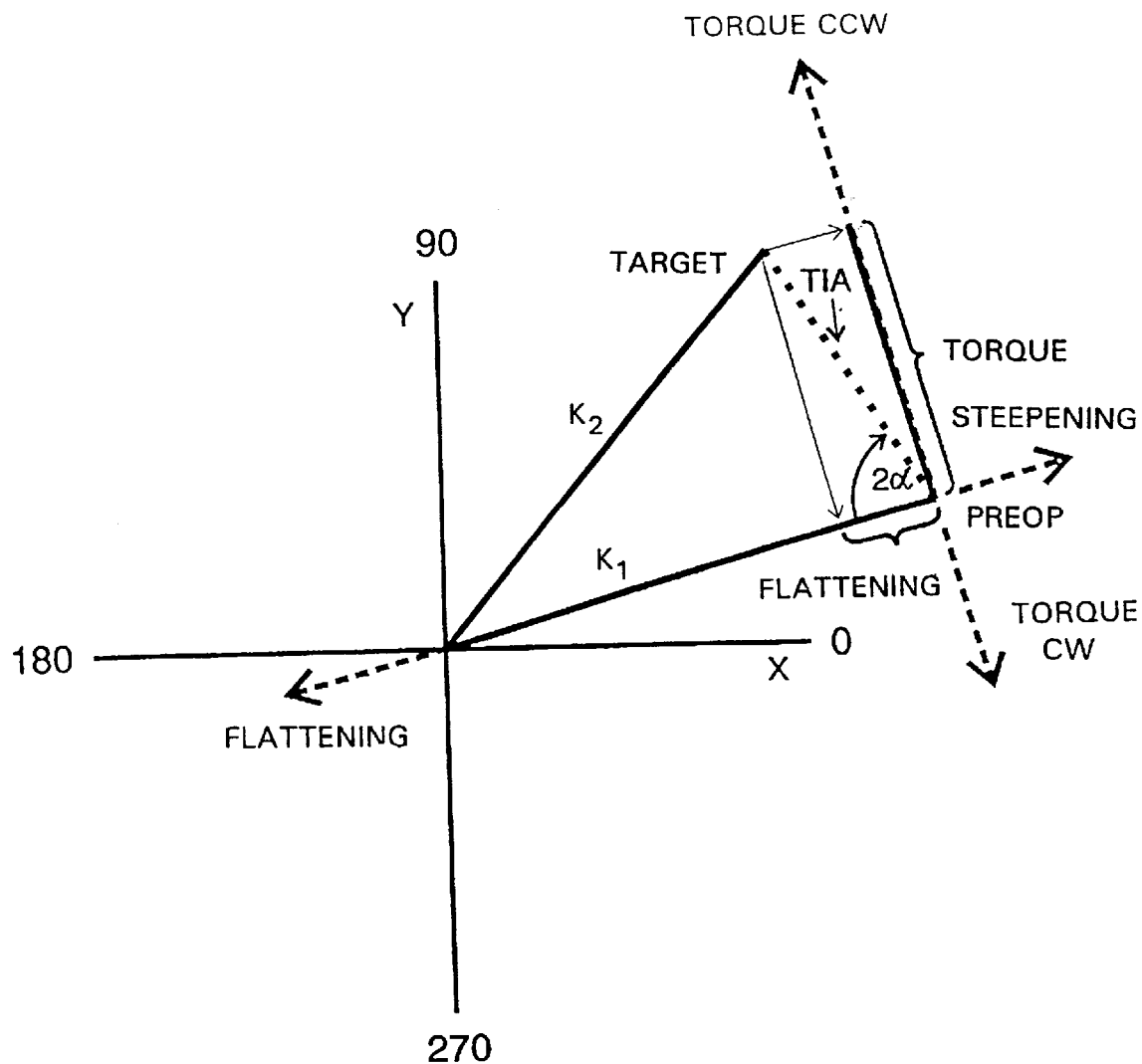
| SURGICAL VECTORS | |
|---|---|
| | EXAMPLE |
| TARGET INDUCED ASTIGMATISM (TIA) | 0.83 AX 62 |
| TORQUE | 0.79 AX 53 |
| FLATTENING | -0.26 AX 8 |
FIG. 22b DOUBLE ANGLE VECTOR DIAGRAM

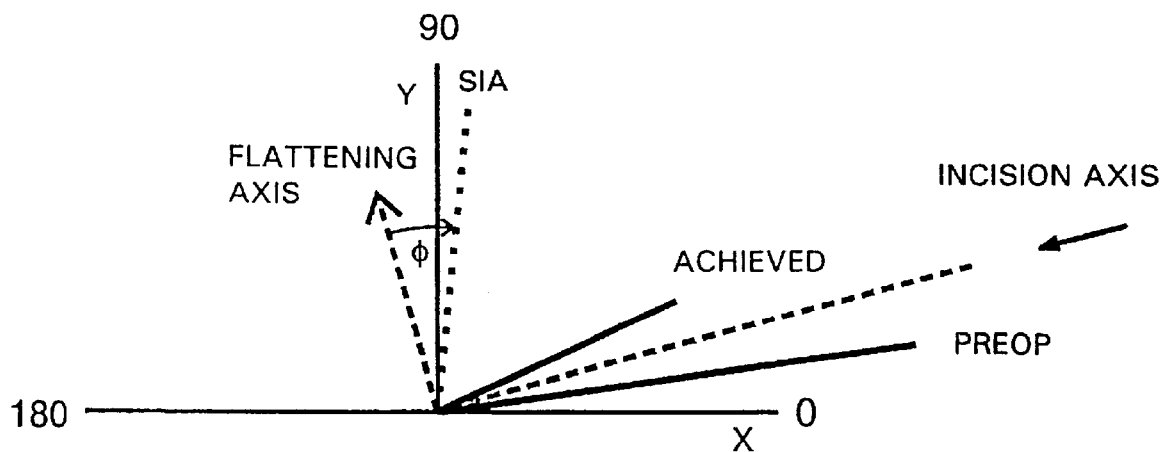
FIG. 23a ASTIGMATISM AND SURGICAL VECTOR DIAGRAM

REFRACTIVE CATARACT SURGERY
FLATTENING/STEEPENING EFFECT OF INCISION
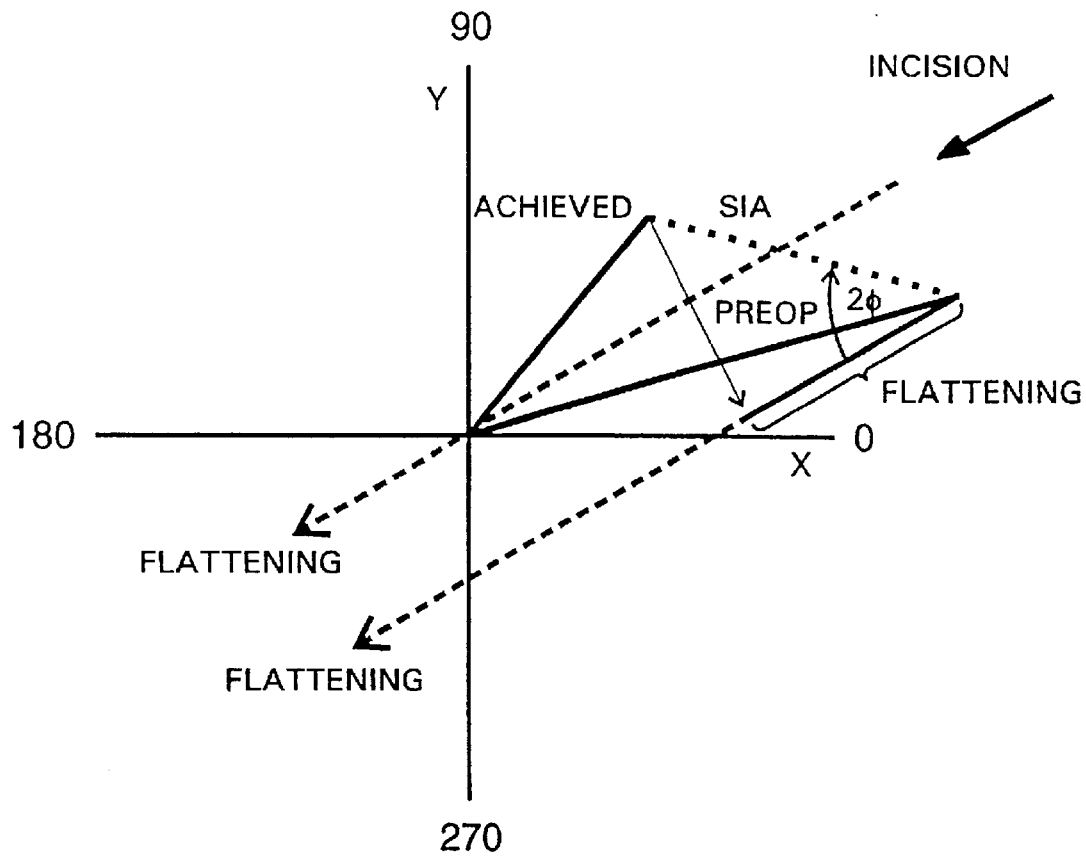
FIG. 23b DOUBLE ANGLE VECTOR DIAGRAM

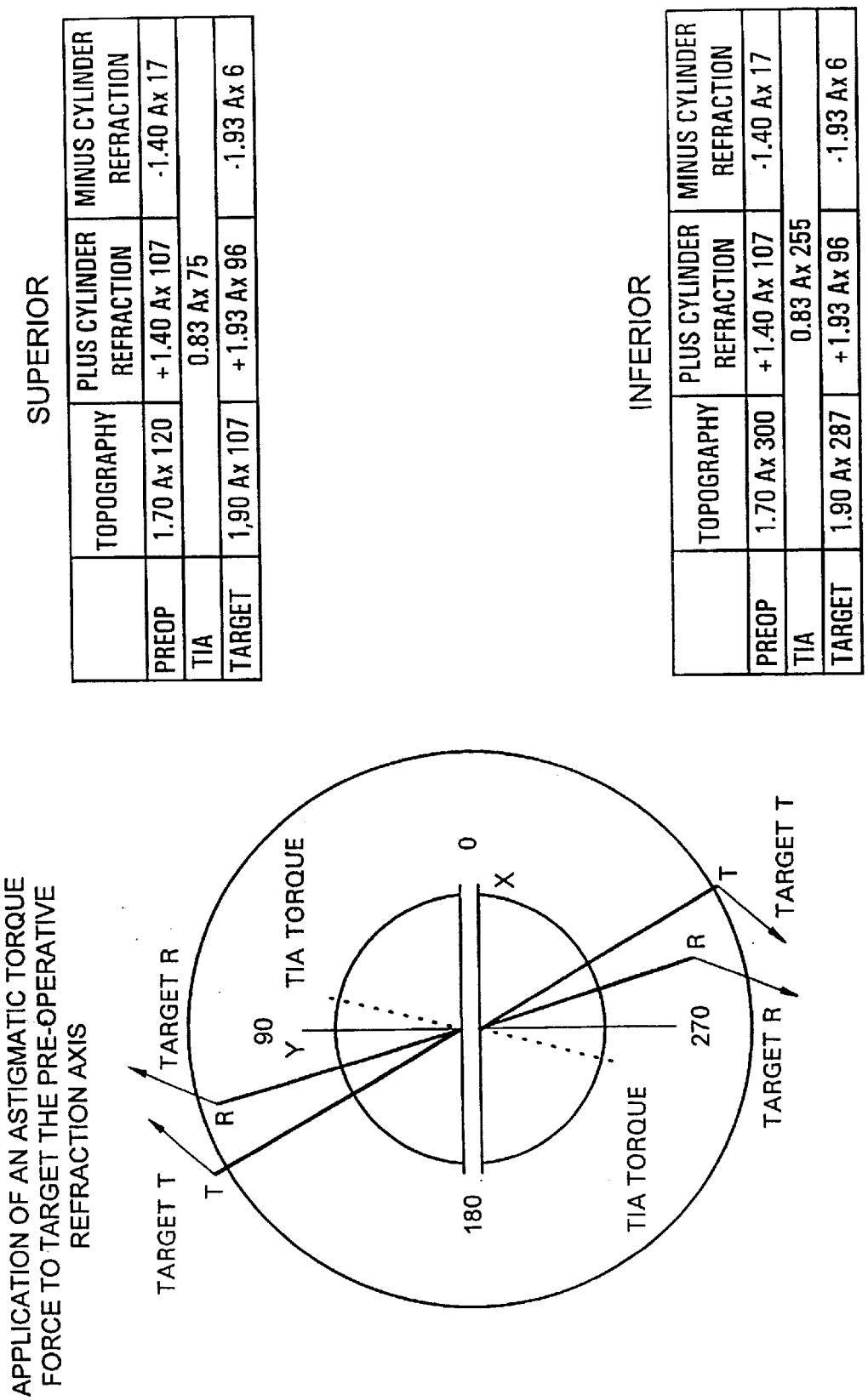
FIG. 24a. ASTIGMATISM AND SURGICAL VECTOR DIAGRAM

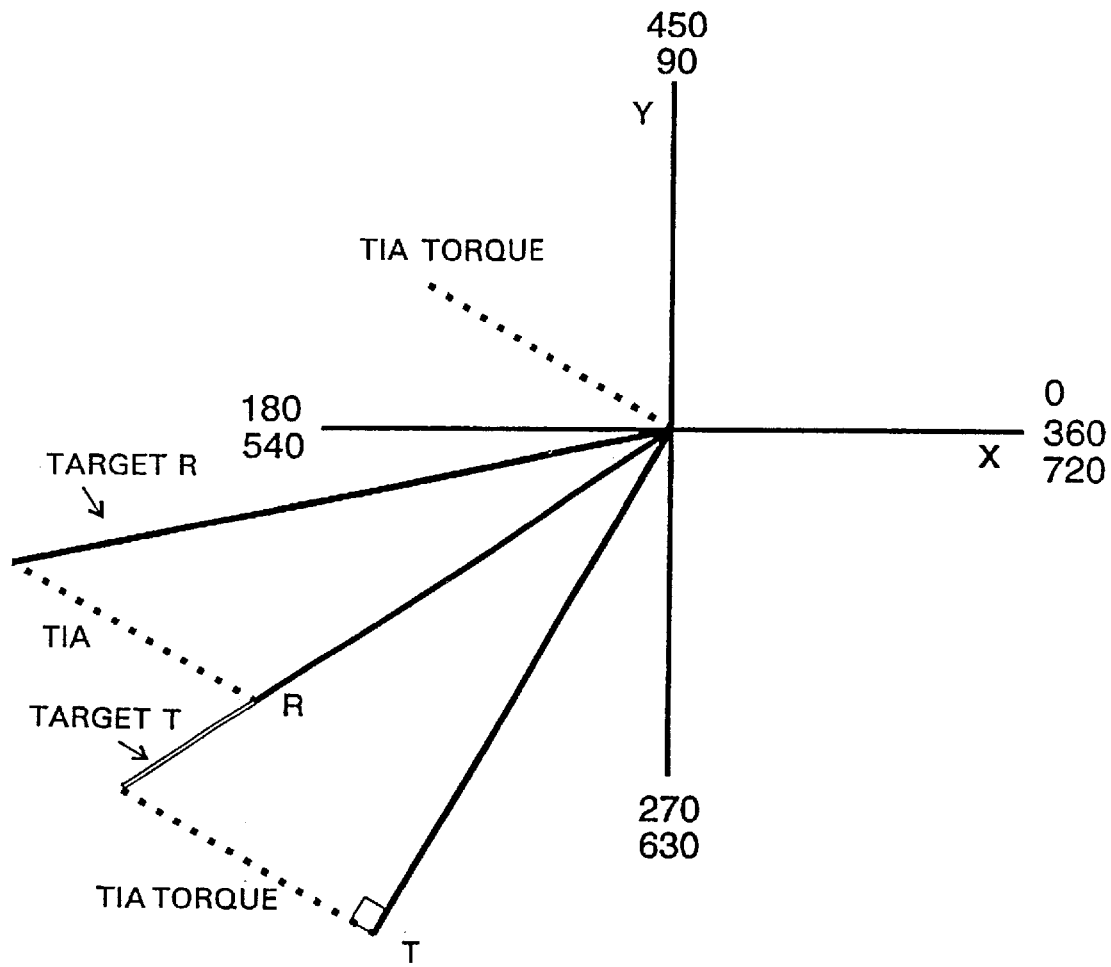
FIG. 24b DOUBLE ANGLE VECTOR DIAGRAM

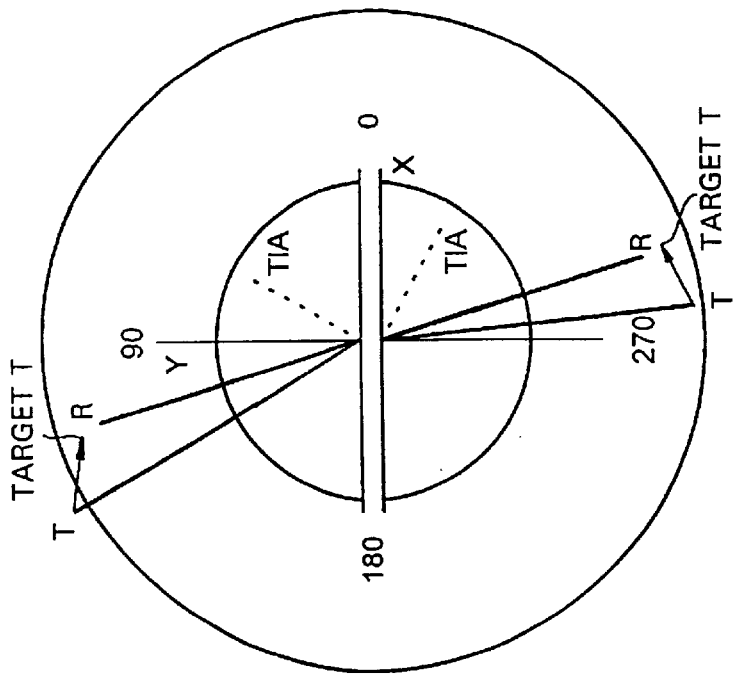

SUPERIOR

| | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | | 0.65 Ax 61 | |
| TARGET | 1.51 Ax 109 | (+1.52 Ax 94) | (-1.52 Ax 4) |

RESOLVED TREATMENT VECTOR

| | PLUS CYLINDER REFRACTION | MINUS CYLINDER REFRACTION |
|---|---|---|
| PREOP | +1.40 Ax 107 | -1.40 Ax 17 |
| TIA Net | 0.00 Ax | |
| TARGET | +1.40 Ax 107 | -1.40 Ax 17 |

INFERIOR

| | TOPOGRAPHY | PLUS CYLINDER REFRACTION | MINUS CYLINDER REFRACTION |
|---|---|---|---|
| PREOP | 1.58 Ax 277 | +1.40 Ax 107 | -1.40 Ax 17 |
| TIA | | 0.65 Ax 331 | |
| TARGET | 1.51 Ax 289 | (+1.60 Ax 119) | (-1.60 Ax 29) |

TREATMENT TO ACHIEVE ORTHOGONAL SYMMETRICAL ASTIGMATISM AND NO CHANGE IN REFRACTIVE ASTIGMATISM

FIG. 25a. ASTIGMATISM AND SURGICAL VECTOR DIAGRAM

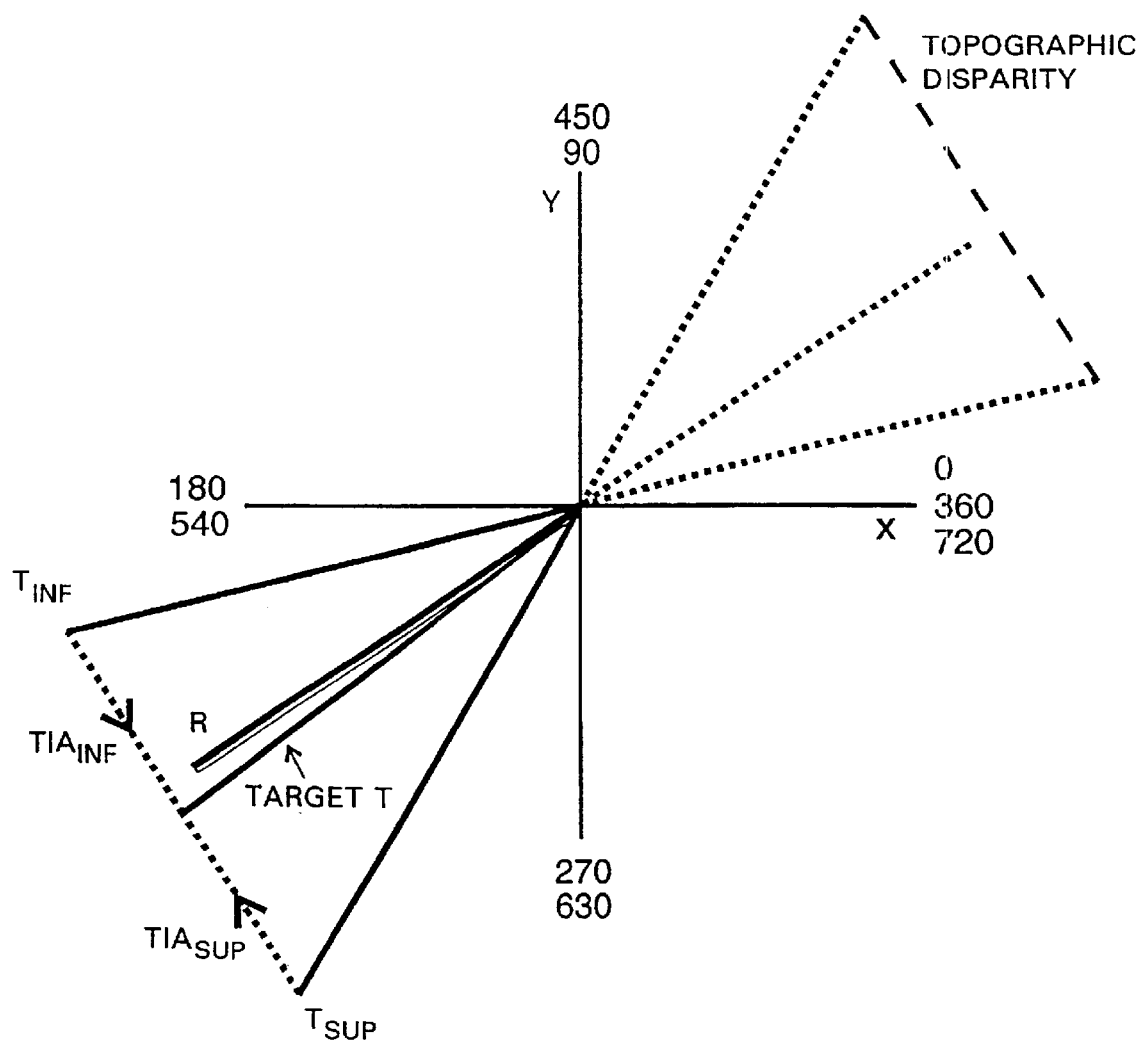
FIG. 25b DOUBLE ANGLE VECTOR DIAGRAM

RESOLUTION OF TREATMENT VECTORS
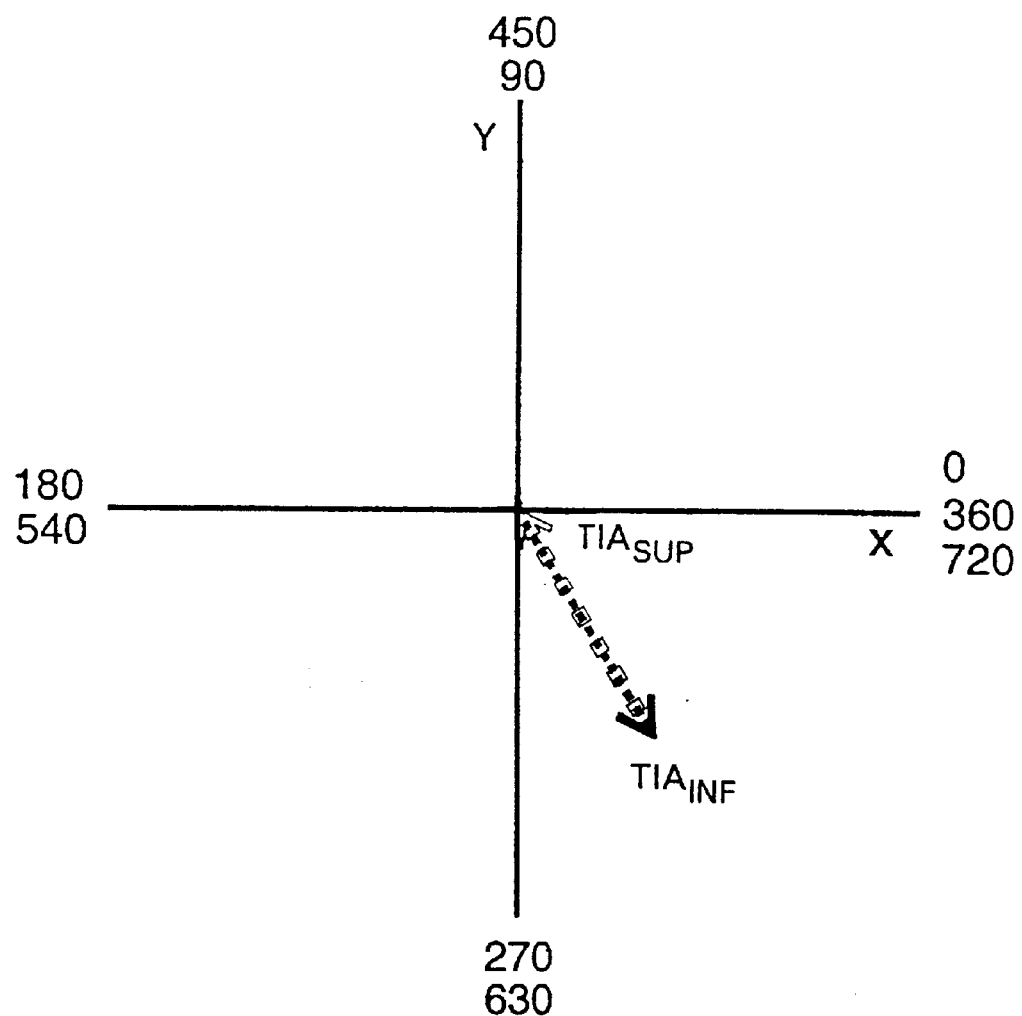
FIG. 25c DOUBLE ANGLE VECTOR DIAGRAM

SUPERIOR

| | TOPOGRAPHY | PLUS CYLINDER REFRACTION | MINUS CYLINDER REFRACTION |
|---|---|---|---|
| PREOP | 1.70 Ax 120 | +1.40 Ax 107 | -1.40 Ax 17 |
| TIA | | 1.29 Ax 61 | |
| TARGET | 1.58 Ax 97 | (+1.87 Ax 85) | (-1.87 Ax 175) |

RESOLVED TREATMENT VECTOR

| | PLUS CYLINDER REFRACTION | MINUS CYLINDER REFRACTION |
|---|---|---|
| PREOP | +1.40 Ax 107 | -1.40 Ax 17 |
| TIANet | 0.65 Ax 61 | |
| TARGET | +1.52 Ax 94 | -1.52 Ax 4 |

INFERIOR

| | TOPOGRAPHY | PLUS CYLINDER REFRACTION | MINUS CYLINDER REFRACTION |
|---|---|---|---|
| PREOP | 1.58 Ax 277 | +1.40 Ax 107 | -1.40 Ax 17 |
| TIA | | 0.00 Ax | |
| TARGET | 1.58 Ax 277 | (+1.40 Ax 107) | (-1.40 Ax 17) |

TREATMENT TO ACHIEVE ORTHOGONAL SYMMETRICAL ASTIGMATISM BY SHIFTING ONE TOPOGRAPHY HEMI-MERIDIAN TO COINCIDE WITH THE MORE FAVOURABLY PLACED ONE

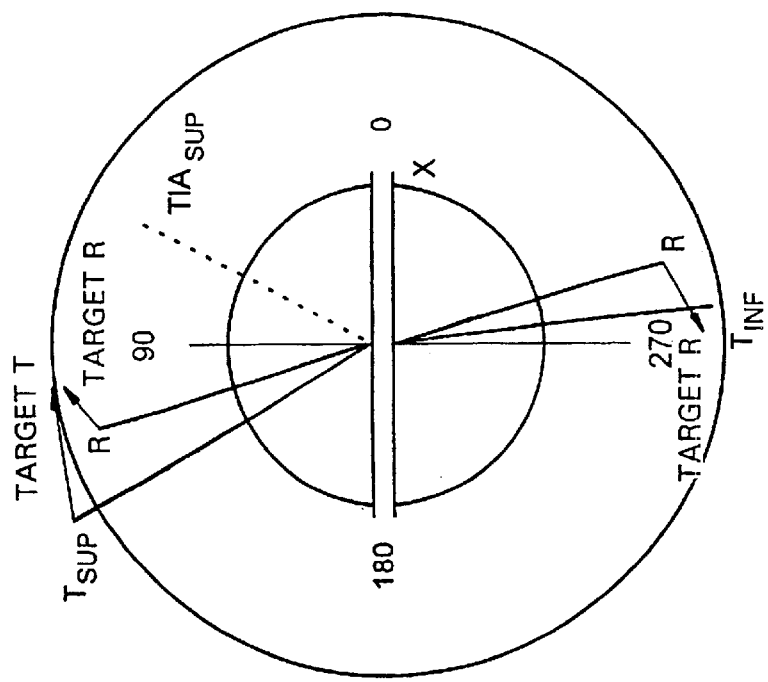

FIG. 26a. ASTIGMATISM AND SURGICAL VECTOR DIAGRAM

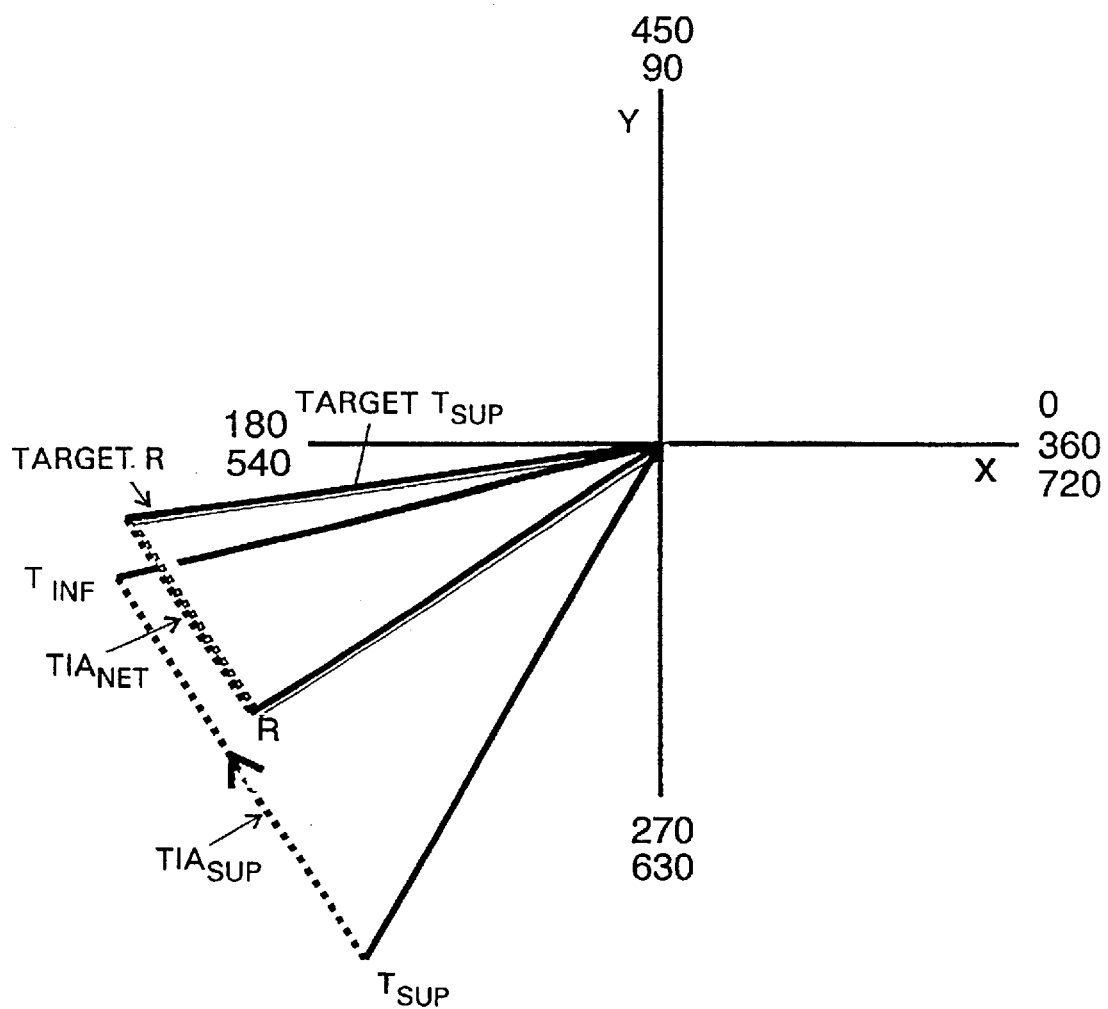
FIG. 26b DOUBLE ANGLE VECTOR DIAGRAM

RESOLUTION OF TREATMENT VECTORS
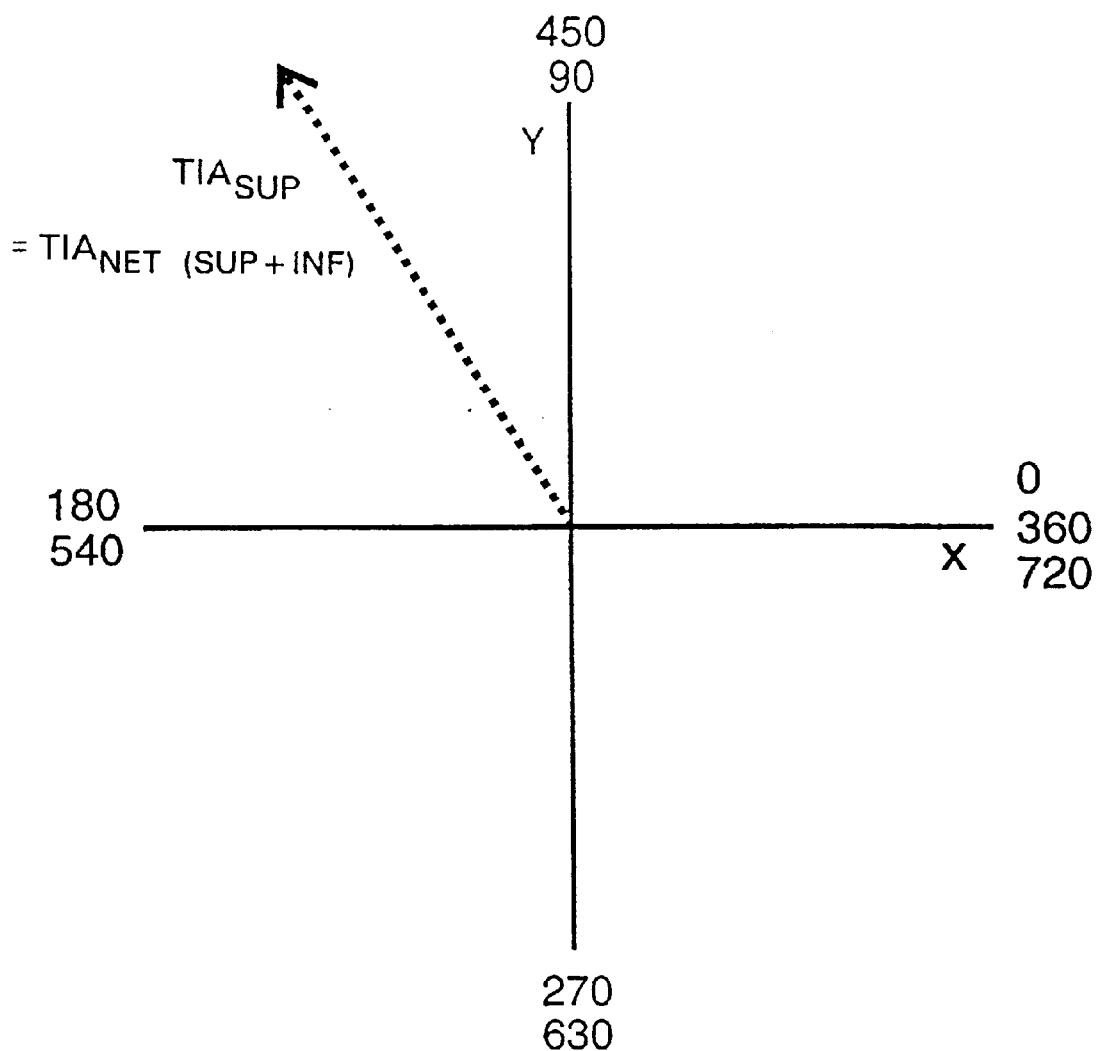
FIG. 26c DOUBLE ANGLE VECTOR DIAGRAM

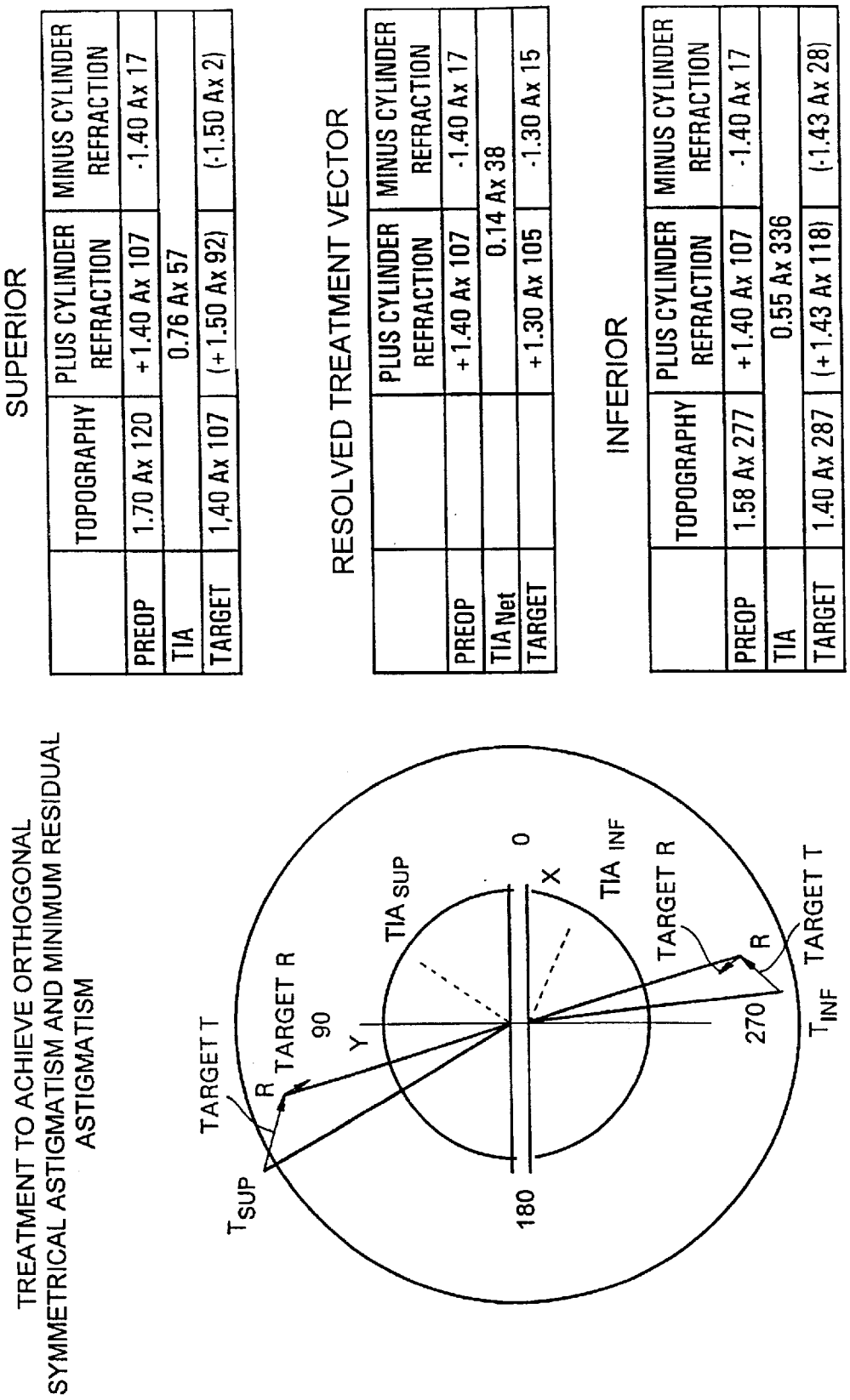
FIG. 27a. ASTIGMATISM AND SURGICAL VECTOR DIAGRAM

TREATMENT TO ACHIEVE ORTHOGONAL SYMMETRICAL ASTIGMATISM AND MINIMUM RESIDUAL ASTIGMATISM
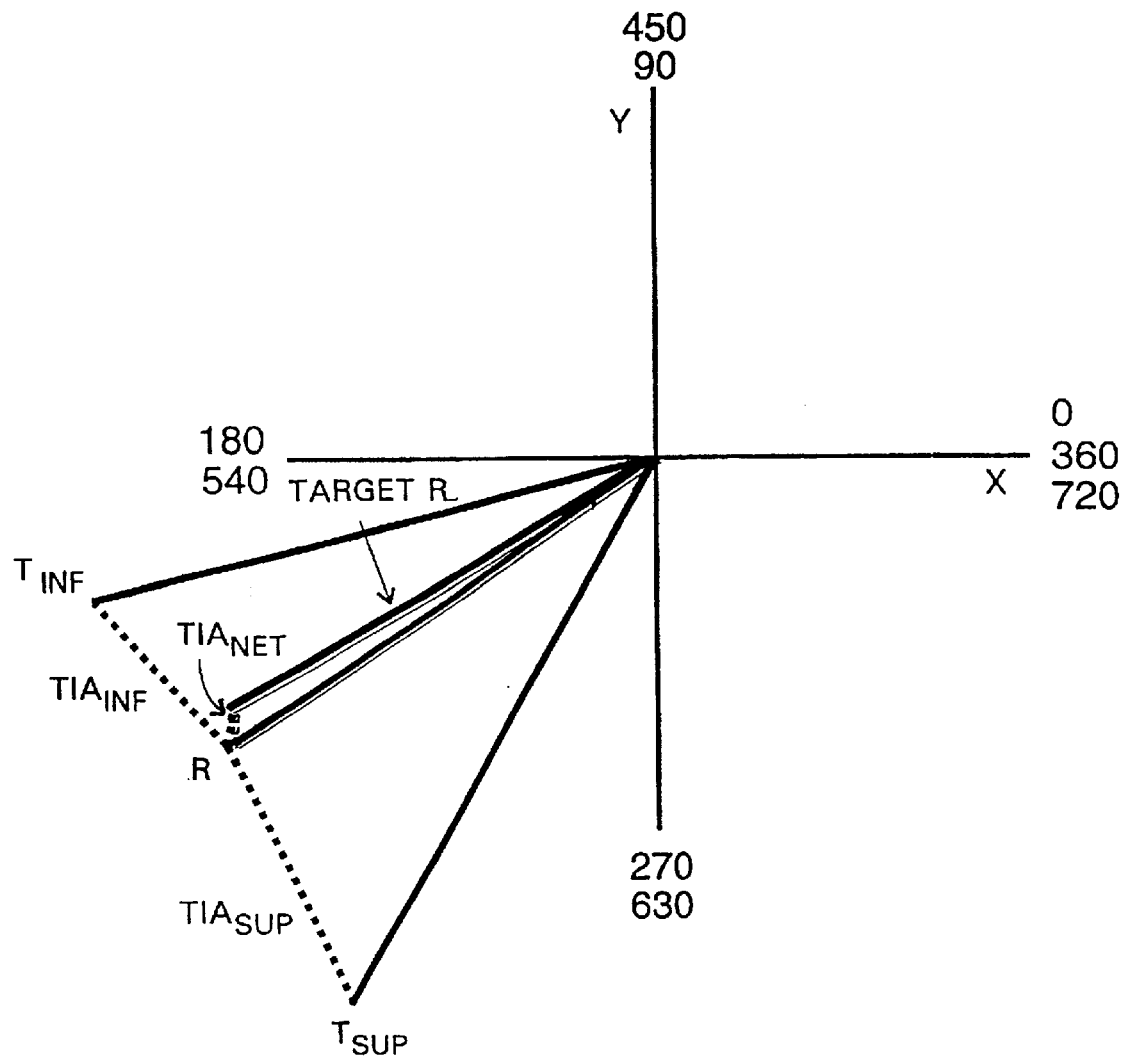
FIG. 27b DOUBLE ANGLE VECTOR DIAGRAM RESOLUTION OF TREATMENT VECTORS
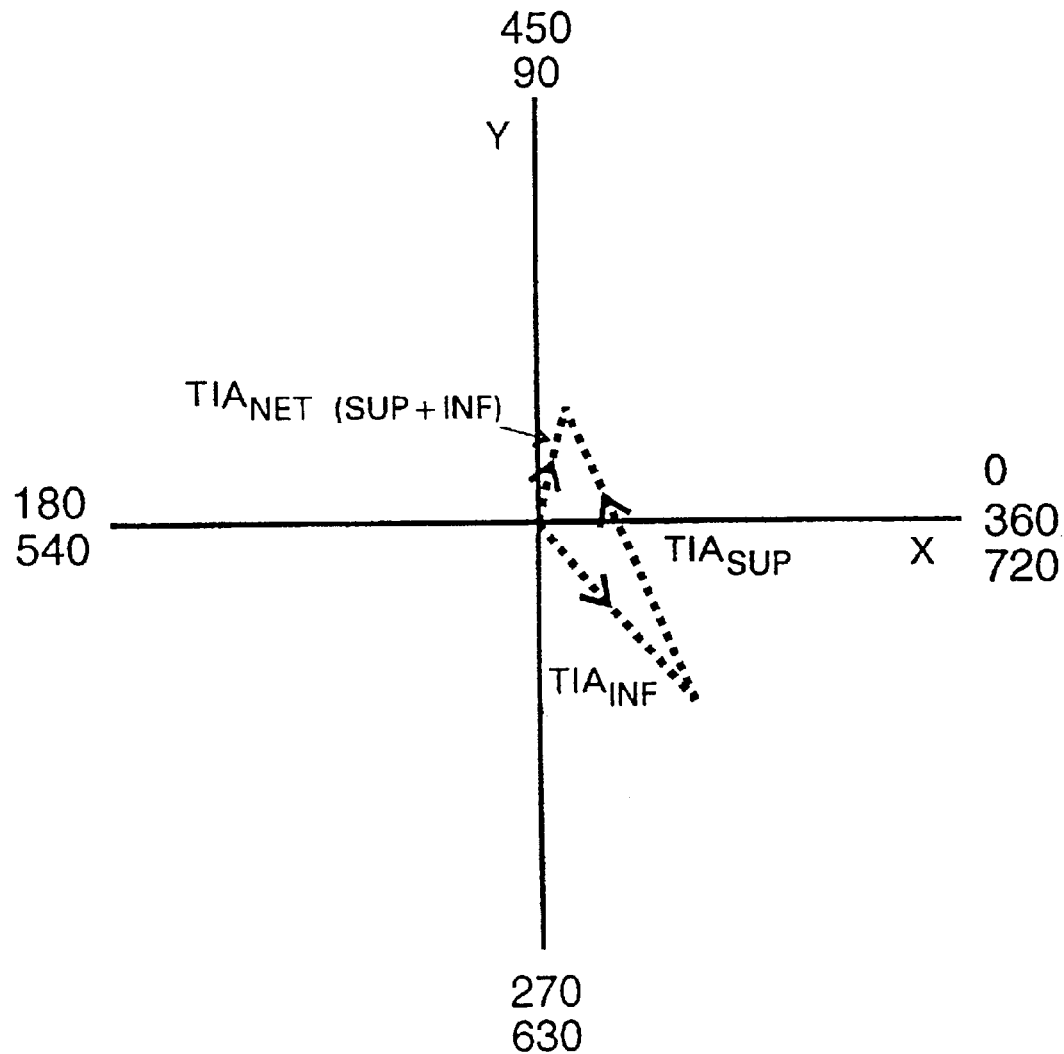
FIG. 27c DOUBLE ANGLE VECTOR DIAGRAM

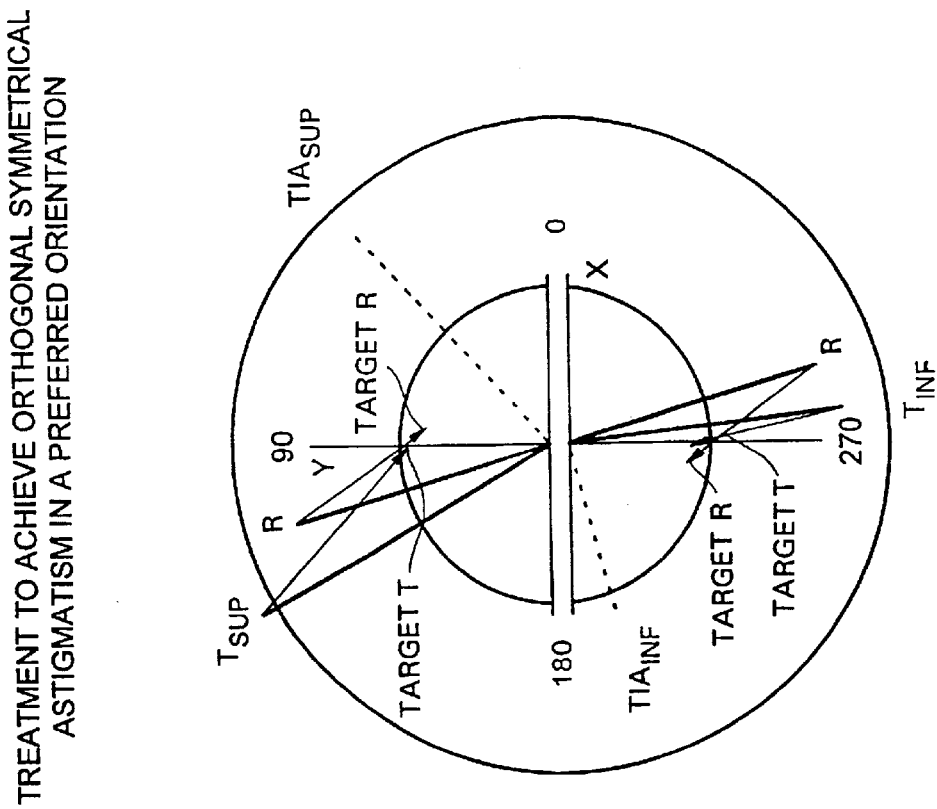
FIG. 28a. ASTIGMATISM AND SURGICAL VECTOR DIAGRAM

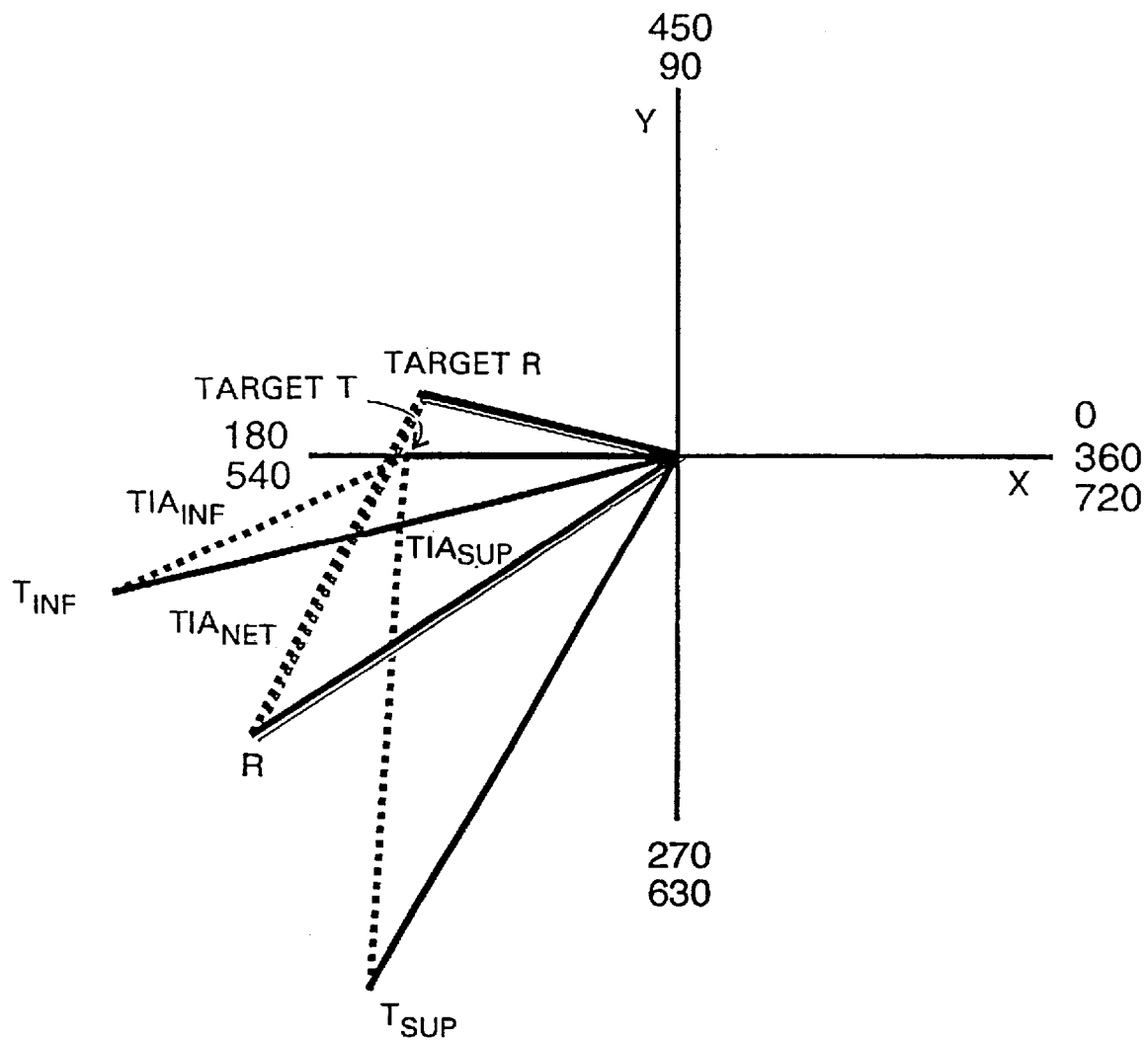
FIG. 28b DOUBLE ANGLE VECTOR DIAGRAM

RESOLUTION OF TREATMENT VECTORS
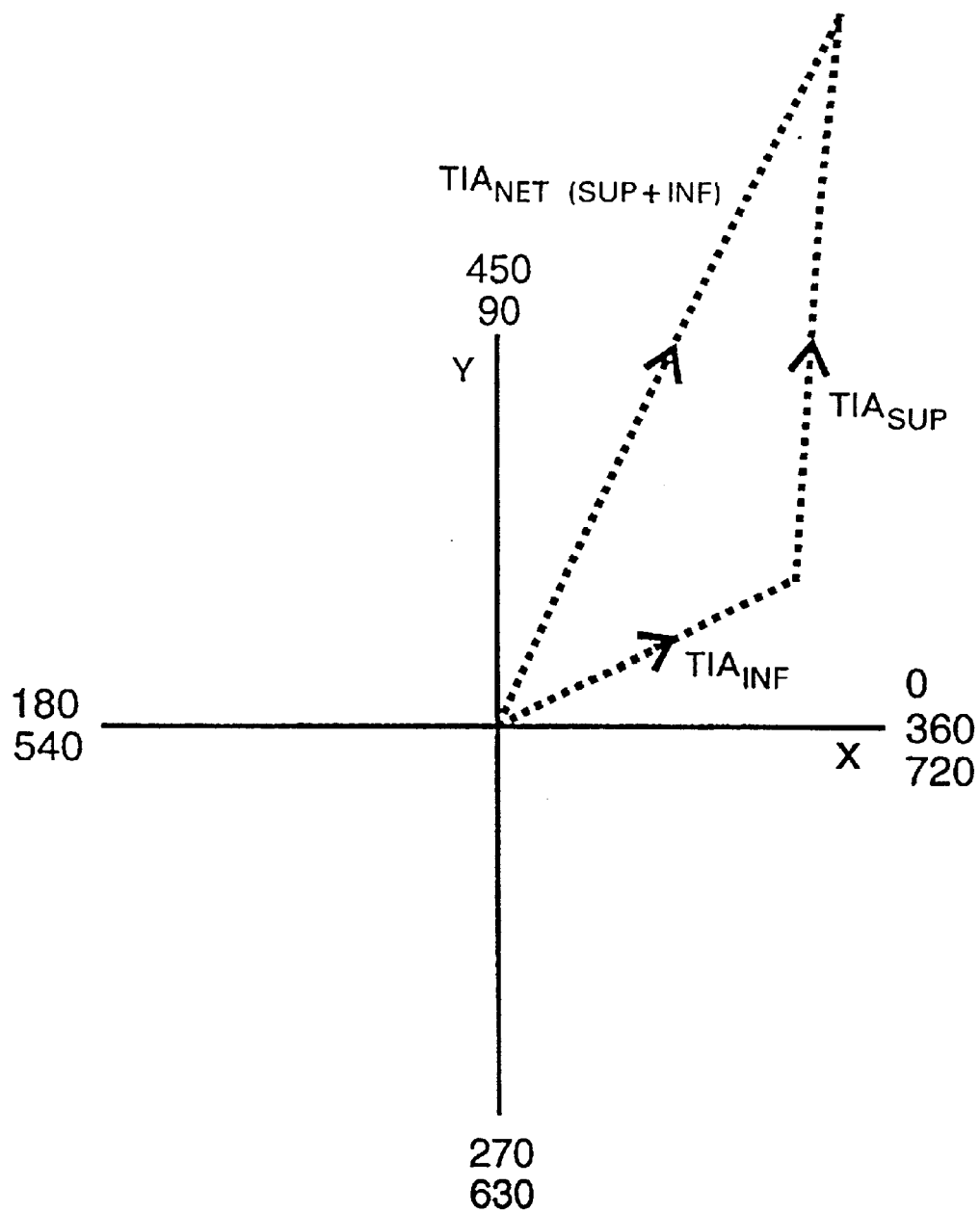
FIG. 28c DOUBLE ANGLE VECTOR DIAGRAM

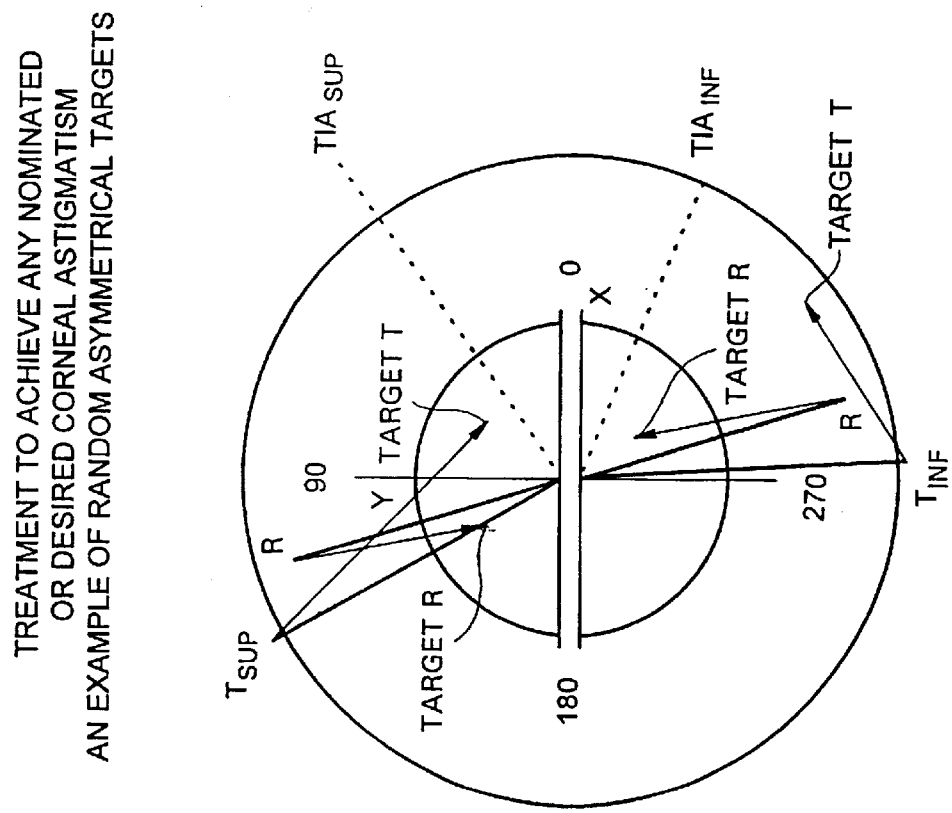
FIG. 29a. ASTIGMATISM AND SURGICAL VECTOR DIAGRAM

TREATMENT TO ACHIEVE ANY NOMINATED OR
DESIRED CORNEAL ASTIGMATISM.
AN EXAMPLE OF RANDOM ASYMMETRICAL TARGETS
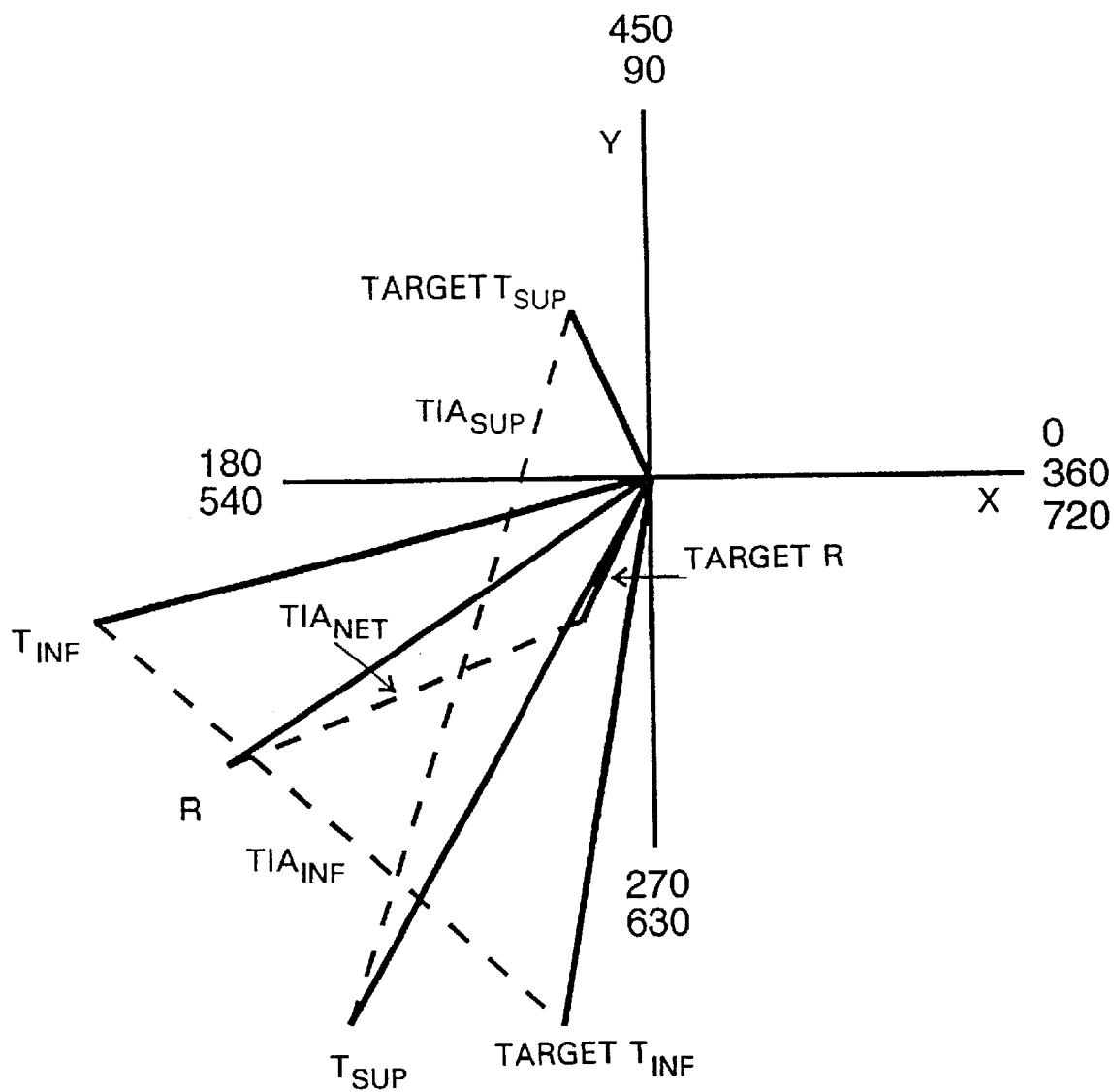
FIG. 29b DOUBLE ANGLE VECTOR DIAGRAM

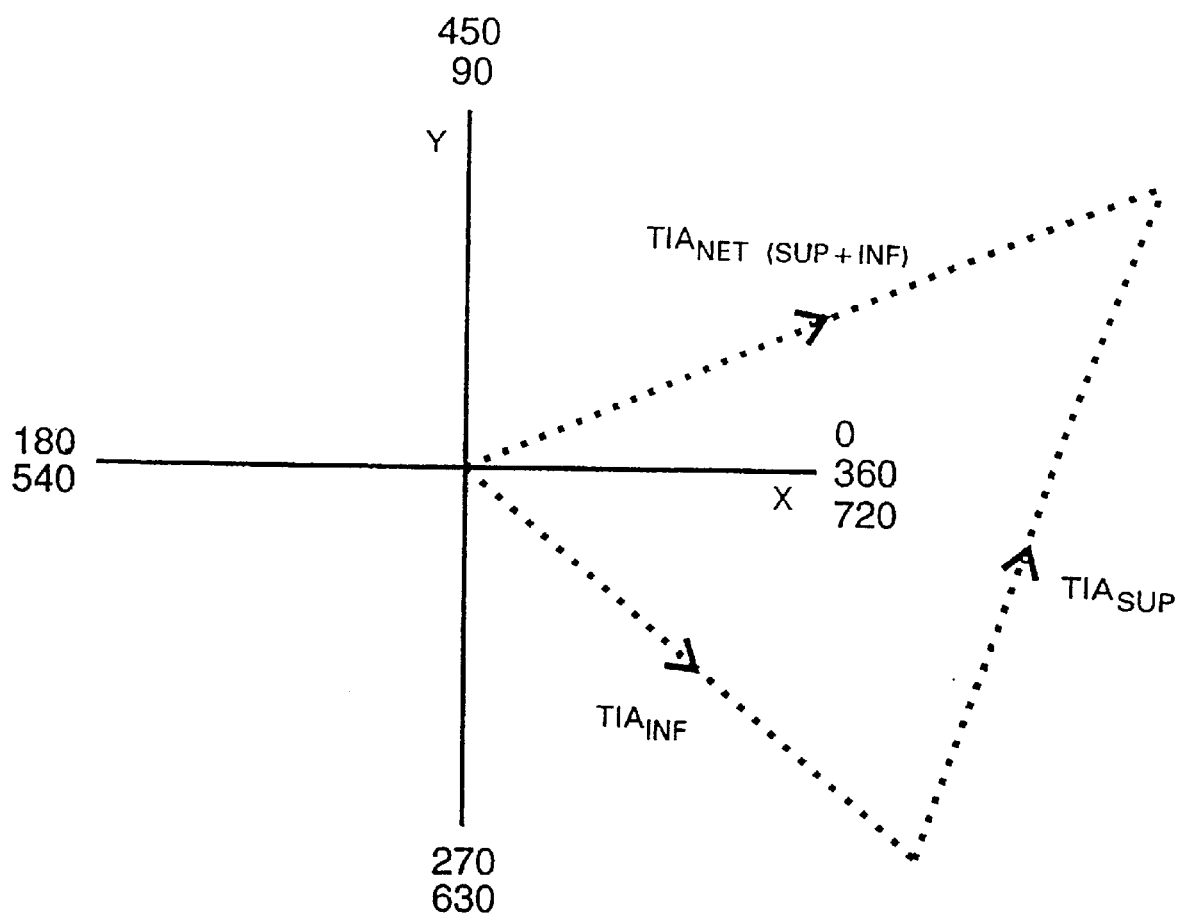
FIG. 29c DOUBLE ANGLE VECTOR DIAGRAM

METHOD FOR SURGICALLY ACHIEVING MINIMUM ASTIGMATISM MEASURED REFRACTIVELY AND TOPOGRAPHICALLY

This is a continuation of application Ser. No. 08/476,449, filed Jun. 7, 1995, now U.S. Pat. No. 5,740,815.

FIELD OF THE INVENTION

This invention relates to a method of analyzing astigmatism which can be used to provide information to enable surgeons to correct astigmatism in patients and also to provide data relating to surgical operations for correcting astigmatism which surgeons can use to improve techniques and surgical success, and also to an apparatus for performing corneal surgery.

The invention relates particularly to methods of surgically correcting astigmatism taking into account refractive and topographical measurements of the eye of the patient.

BACKGROUND

Current methods of analyzing astigmatism are confined to calculation of the vector of change surgically induced in attaining the post-operative result from the pre-operative state.

This ably allows determination of total induced astigmatism and the direction of the vector force acting in the eye. It also enables calculation of the mean total surgical astigmatism induced when a series of operations are compared and analyzed. However, the axes of surgical induced astigmatism (SIA) generally varies considerably within the 180° arc of range. This makes it extremely difficult to make meaningful comparisons of astigmatic change for a series, as one cannot obtain an average directional change of vectors, as vectors in opposing or partly opposing directions cancel each other out in varying amounts.

One practice carried out by some surgeons is to resort to the sole option of tabulating each patient's results individually, leaving it to the reader to estimate any trend. Some surgeons attempt to provide an overview of results, but lack the means to deduce a trend in induced astigmatism vectors as a group, because they have variable orientation.

Taking a mean of the angles has no validity in determining the trend for axes, nor does it address the change in axes from their pre-operative to post-operative astigmatic status. It does not assess the success or desirability of the achieved result; furthermore, it does not indicate the extent to which the surgical aim was achieved. An attempt has been made to address the complexities of correcting the magnitude for the degrees of axis change by introducing the approximation that this component varies as the cosine of the difference between the attempted and the observed (achieved) axes. This corrected value of magnitude was substituted as the amount of surgically induced astigmatism measured on a cylinder 90° to the axis of the incisions, the so-called "proper" axis. It has been proposed to program so called Naylor's equations into a computer program that requires slight modifications to resolve the ambiguity and essentially reproduce the Naylor table.

The formula for calculation of SIA is derived from the resultant of two plano-cylindrical lenses with axes at different angles; this was subsequently employed by some surgeons using graphical methods confirming the magnitude and axis of the astigmatic change. Jaffe and Clayman employ rectangular and polar co-ordinates to determine, by vector analysis, the formula for calculating SIA and its axis with the known values for pre- and post-operative corneal astigmatism. Analogous formulae were derived by Hall based on Martin and Welford's derivation of Euler's theorem of curved surfaces (investigated by Airy in 1827).

Euler's theorem, which states "that the sum of the curvatures of any two perpendicular sections of a cylindrical or toric surface has a constant value", provides the link between Jaffe's and Naeser's methods of vector analysis. Naeser's method calculates the polar values of astigmatism, arising when the axis of astigmatism does not lie on 90° or 180° meridia; its use lies primarily in interpreting results of surgery which induces polar (with-the-rule and against-the-rule) changes, such as cataract and implant surgery (with or without transverse astigmatic keratotomy).

Astigmatism is a unique refractive error that causes reduced visual acuity and produces symptoms such as glare, monocular diplopia, asthenopia and distortion. For some years now, astigmatism control and correction has been of great concern to refractive, cataract and corneal surgeons. Reduction or elimination of astigmatism, as a single or combined procedure, is only possible if one possesses an understanding of astigmatic change, in its component parts of magnitude and axis. Current analytical techniques do not allow us to compare magnitudes and axes separately for a series of paired groups of procedures or for a single procedure, yet it is only in this way that we are able to perfect techniques of astigmatism surgery. We need to be able to determine the preferable technique to employ; we also need to be able to determine whether any failure to achieve surgical goals is attributable to an individual patient factor or to machine or technique error. Modern laser technologies have empowered us with the ability to modify our procedures with degrees of sophistication not previously possible; this in turn requires analysis systems which will allow us to accurately quantify and scientifically assess the results.

SUMMARY OF THE INVENTION

An object of the present invention is to provide a method which allows more meaningful information to be obtained which can be used by surgeons to provide a greater degree of success when applied to an individual patient and also to provide statistical information which will enable techniques to be improved.

The present invention provides a method of treating astigmatism comprising the steps of:
  determining a pre-operative astigmatism;
  defining a target or aimed astigmatism;
  calculating a target induced astigmatism vector which is the difference between the target astigmatism and the pre-operative astigmatism; and
  calculating from the target induced astigmatism vector the direction and amount of relative steepening or flattening of the cornea to provide parameters of a surgical procedure in magnitude and direction.

The target induced astigmatism vector may be modified by an angle of error and a magnitude of error.

The present invention also provides another method of treating astigmatism comprising the steps of:
  determining a pre-operative astigmatism;
  defining a target or aimed astigmatism;
  determining an achieved astigmatism following a surgical procedure;
  calculating a target induced astigmatism vector which is the difference between the aimed astigmatism and the pre-operative astigmatism, calculating a target induced astigmatism vector which is the difference between the achieved astigmatism and the pre-operative astigmatism, and calculating a difference vector which is the difference between the aimed astigmatism, and the achieved astigmatism to enable magnitudes of the vectors and angles of the vectors to be obtained.

The present invention also provides another method of treating astigmatism comprising the steps of:

determining a pre-operative astigmatism including a magnitude and axis of astigmatism in a 0° to 180° range;

defining a target or aimed astigmatism including a magnitude and axis, the axis being an angle presented in a 0° to 180° range;

determining an achieved astigmatism following a surgical procedure, the achieved astigmatism having a magnitude and axis, the axis being an angle presented in a 0° to 180° range;

doubling the angles of the axes of the pre-operative astigmatism, target astigmatism and achieved astigmatism to convert the axes to a 360° range;

calculating a target induced astigmatism vector which is the difference between the target astigmatism and the pre-operative astigmatism, calculating a surgically induced astigmatism vector which is the difference between the achieved astigmatism and the pre-operative astigmatism, calculating a difference vector which is the difference between the target astigmatism and the achieved astigmatism, and halving the angle of the target induced astigmatism vector, the surgically induced astigmatism vector and the difference vector to return the angle values to a 0° to 180° range and calculating the magnitudes of the vectors to thereby provide astigmatism vector magnitude values and vector angle values.

Since the method produces astigmatism magnitude values and angle values, and in particular a target induced astigmatism vector and a difference vector, results obtained can be used to predict trends in surgery to enable techniques to be improved and also to use particular results for a particular patient in order to surgically correct a previously surgically induced astigmatism to a target induced astigmatism.

Preferably, the step of doubling the vector angles includes the step of converting from polar coordinates to rectangular coordinates.

Preferably, the step of determining preoperative astigmatism comprises making corneal measurements of a patient or, in an alternative embodiment, utilizing information relating to glasses prescription of the patient.

Preferably, the method includes a step of determining a coefficient of adjustment by dividing the target induced astigmatism vector by the surgically induced astigmatism vector.

Preferably, the method includes determining an angle or error and a magnitude of error which are respectively the angle difference and magnitude difference between the surgically induced astigmatism vector and the target induced astigmatism vector.

Preferably, the method includes determining an index of success which is the magnitude of the difference vector divided by the magnitude of the target induced astigmatism vector.

Preferably, the method includes determining an angle of correction which is the angular difference between aimed astigmatism and the achieved astigmatism.

Preferably, the method includes calculating an angle of error which is the angular difference between the surgically induced astigmatism vector and the target induced astigmatism vector.

Preferably, the method includes a step of determining the axis or angle of the difference vector and the magnitude of the difference vector.

Another object of the invention is to achieve surgical correction of astigmatism taking into account differing refractive and topographical measurements of the eye.

Another object of the invention is to achieve such surgical correction so that astigmatism in the eye following surgery when measured topographically and refractively is a minimum. In this respect, when there is a difference between refractive and topographical measurements of astigmatism, surgical intervention considering only one of the above measurements may lead to residual astigmatism following surgery which is worse when measured on the basis of the unconsidered measurement.

The invention satisfies the above object of surgically correcting astigmatism of an eye of a patient taking into account refractive and topographical measurements of the astigmatism by a method comprising:

measuring magnitude and axis of astigmatism of an eye of a patient based on topography of the cornea of the eye of the patient, measuring magnitude and axis of astigmatism of the eye of the patient based on refractive correction of said eye, determining surgical parameters based on the measurements of astigmatism both refractively and topographically, and surgically treating the eye according to said surgical parameters, said surgical parameters being determined by a) summating the values of astigmatism measured topographically on the values of astigmatism measured refractively, on the one hand, and the values of astigmatism measured refractively on the values of astigmatism measured topographically, on the other hand, to obtain respective non-zero target astigmatism values for refraction and topography, and b) establishing said surgical parameters based on both said target astigmatism values such that the sum of the target astigmatism values for refraction and topography is a minimum, whereby astigmatism in the eye following surgery will be a minimum when measured topographically and refractively.

The step of summating the astigmatism values comprises vectorially subtracting the respective astigmatism values from one another.

A further object of the invention is to provide a method by which an eye having non-symmetrical topography can be treated for astigmatism.

The above object is satisfied by a method comprising:

considering the cornea as divided into two hemi-divisions, and determining surgical parameters for each hemi-division independently of the other.

Another object of the invention is to provide a method for altering the axis of astigmatism of the eye without altering its magnitude. This is particularly effective according to the invention, to bring hemi-meridians of non-symmetrical topography of an eye into orthogonal correspondence.

The present invention also resides in an apparatus for performing corneal surgery comprising:

means for performing surgery on a patient's cornea;

control means for controlling the means for performing surgery; and processing means for receiving said target induced astigmatism vector for the patient and for outputting signals to control the control means in accordance with the target induced astigmatism vector.

Preferably, the means for performing surgery comprises a source of ultraviolet radiation and a shutter device and the control means controls the opening duration of the shutter device and the intensity of the source of ultraviolet radiation.

Preferably, the processing means includes input means for inputting data relating to pre-operative astigmatism of the patient and target or aimed astigmatism so that the processing means can calculate the target induced astigmatism vector.

BRIEF DESCRIPTION OF THE FIGURES OF THE DRAWING

Preferred embodiments of the invention will be described, by way of example, with reference to the accompanying drawings in which:

FIG. 15a is an astigmatism and surgical vector diagram;

FIG. 15b shows the vectors in FIG. 15a plotted on a double angle vector diagram with the parameters of the vectors set forth in the box adjacent to the vector diagram;

FIG. 16a is a double angle vector diagram showing treatment by topography with the parameters of the vectors set forth in the box adjacent to the vector diagram;

FIG. 16b is a double angle vector diagram showing treatment by refraction, with the parameters of the vectors set forth in the box adjacent the vector diagram;

FIG. 17a is a double angle vector diagram showing treatment with a target induced astigmatism vector to produce minimum target astigmatism with the parameters of the vectors set forth in the box adjacent to the vector diagram;

FIG. 17b is a double angle vector diagram showing treatment with an optimal target induced astigmatism vector to achieve optimal minimum target astigmatism with the parameters of the vectors set forth in the box adjacent to the vector diagram;

FIG. 18a is a double angle vector diagram showing treatment without regard to minimal target astigmatism to illustrate overcorrection, with the parameters of the vectors set forth in the box adjacent to the vector diagram;

FIG. 18b is a double angle vector diagram showing treatment without regard to minimal target astigmatism to illustrate undercorrection, with the parameters of the vectors set forth in the box adjacent to the vector diagram;

FIG. 20a graphically illustrates in superimposition on an eye vector diagrams for superior and inferior hemi-divisions of the eye, with the parameters of the vectors set forth in the box adjacent to the vector diagram;

FIG. 20b graphically illustrates a double angle vector diagram showing resolution of the treatment vectors of FIG. 20a;

FIG. 20c graphically illustrates a double angle vector diagram showing optimal treatment for hemi-divisions of the eye of FIG. 20a;

FIG. 21a graphically illustrates astigmatism and surgical vectors to produce astigmatic torque on the eye, with the parameters of the vectors set forth in the box adjacent to the vector diagram;

FIG. 21b graphically illustrates the parameters of FIG. 21a on a double angle vector diagram, with the parameters of the vectors set forth in the box adjacent to the vector diagram;

FIG. 22a graphically illustrates astigmatism and surgical vectors similar to FIG. 21a, but with corneal flattening, with the parameters of the vectors set forth in the box adjacent to the vector diagram;

FIG. 22b illustrates the vectors of FIG. 22a on a double angle vector diagram, with the parameters of the vectors set forth in the box adjacent to the vector diagram;

FIG. 23a is a vector diagram illustrating the effect of flattening or steepening on astigmatism following surgery, with the parameters of the vectors set forth in the box adjacent to the vector diagram;

FIG. 23b illustrates the vectors of FIG. 23a on a double angle vector diagram, with the parameters of the vectors set forth in the box adjacent to the vector diagram;

FIG. 24a graphically illustrates in superimposition on an eye, vector diagrams for superior and inferior hemi-divisions of the eye for achieving astigmatic torque, with the parameters of the vectors set forth in the box adjacent to the vector diagram;

FIG. 24b shows the vectors of FIG. 24a on a double angle vector diagram;

FIG. 25a is similar to FIG. 24a for treatment to achieve orthogonal symmetrical astigmatism without change in refractive astigmatism, with the parameters of the vectors set forth in the box adjacent to the vector diagram;

FIG. 25b shows the vectors of FIG. 25a on a double angle vector diagram;

FIG. 25c shows the resolution of treatment vectors from FIG. 25b;

FIG. 26a is similar to FIG. 25a for treatment to achieve orthogonal symmetrical astigmatism with orientation shifted towards favorable "with the rule" orientation, with the parameters of the vectors set forth in the box adjacent to the vector diagram;

FIG. 26b shows the vectors of FIG. 26a on a double angle vector diagram;

FIG. 26c shows the resolution of treatment vectors from FIG. 26b;

FIG. 27a is similar to FIG. 26a for treatment to achieve orthogonal symmetrical astigmatism with minimum residual astigmatism, with the parameters of the vectors set forth in the box adjacent to the vector diagram;

FIG. 27b shows the vectors of FIG. 27a on a double angle vector diagram;

FIG. 27c shows the resolution of treatment vectors from FIG. 27b;

FIG. 28a is similar to FIG. 27a for treatment to achieve orthogonal symmetrical astigmatism in a preferred orientation, with the parameters of the vectors set forth in the box adjacent to the vector diagram;

FIG. 28b shows the vectors of FIG. 28a on a double angle vector diagram;

FIG. 28c shows the resolution of treatment vectors from FIG. 28b;

FIG. 29a is similar to FIG. 28a for treatment to achieve any nominal desired corneal astigmatism;

FIG. 29b shows the vectors of FIG. 29a on a double angle vector diagram; and

FIG. 29c shows the resolution of treatment vectors from FIG. 29b.

DETAILED DESCRIPTION

Figure 1:
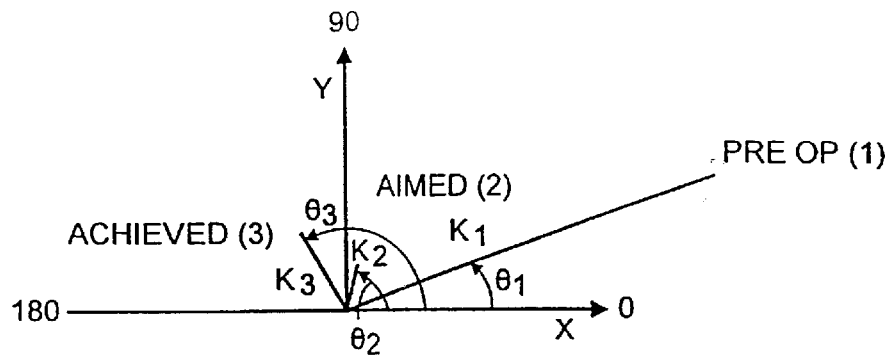
FIG. 1 is a graph showing typical pre-operative, aimed and achieved astigmatism values for a patient.

The astigmatism values used to assess results are shown in FIG. 1 for a typical patient and are:

(1) Pre-operative astigmatism, magnitude $K_1$ diopters at steepest axis $\theta_1$ (2) Targeted or aimed astigmatism, magnitude $K_2$ diopters at steepest axis $\theta_2$ (3) Achieved astigmatism, magnitude $K_3$ diopters at steepest axis $\theta_3$ where $K_1$, $K_2$ and $K_3$ are the dioptric differences between the steepest and flattest curvatures of the cornea, at the steepest axes $\theta_1$, $\theta_2$ and $\theta_3$ For example the pre-operative astigmatism is 4.00 diopters at 20°, the targeted or aimed astigmatism is 0.75 diopters at 70° and the achieved astigmatism is 1.25 diopters at 125°.

Astigmatism is normally represented in a 0° to 180° sense. This representation complicates interpretation of results in that a change in astigmatism from, say, a pre-operative value of 5° to a post-operative value of 175° appears both visually, on a graph, and numerically to be a 170° change whereas it is in fact only a 10° change.

Figure 2:
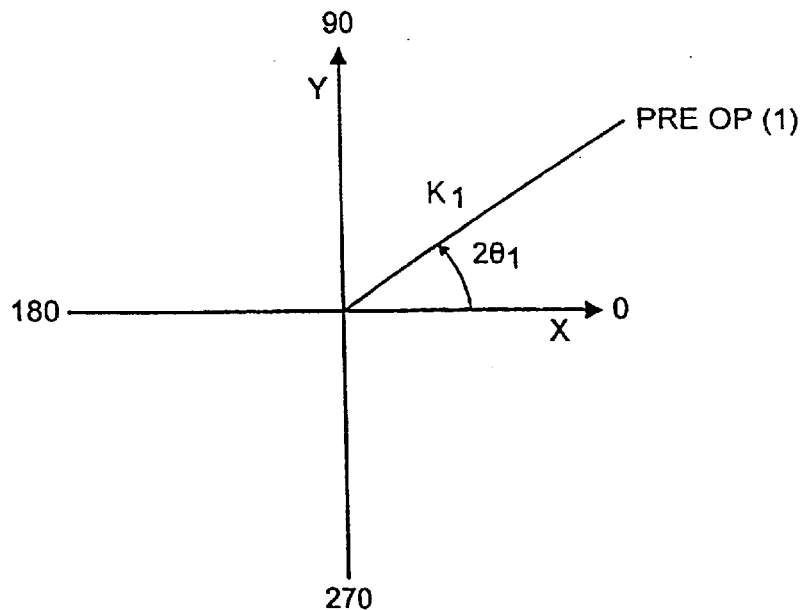
FIGS. 2, 3 and 4 are double angle vector diagrams for the astigmatism values shown in FIG. 1.
Figure 3:
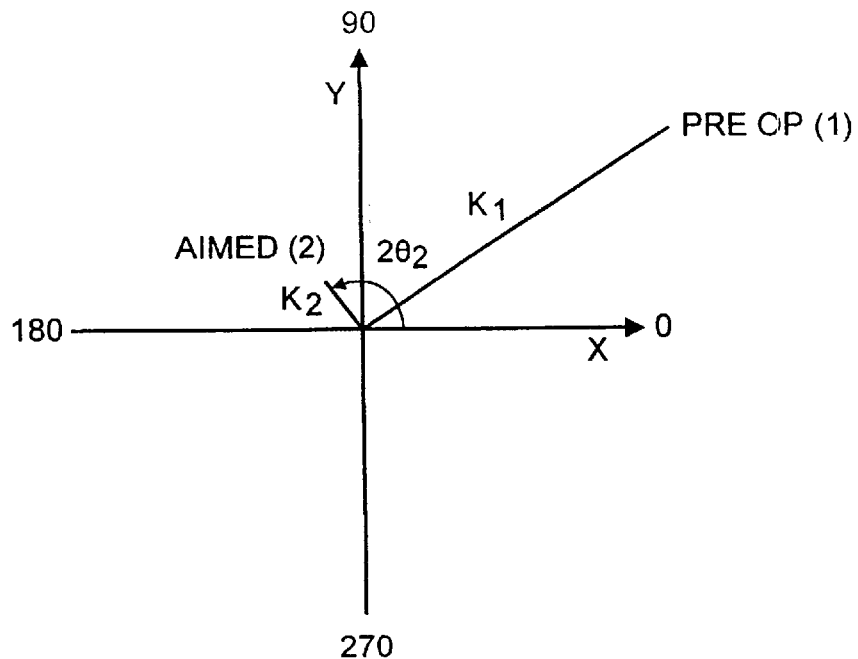
Figure 4:
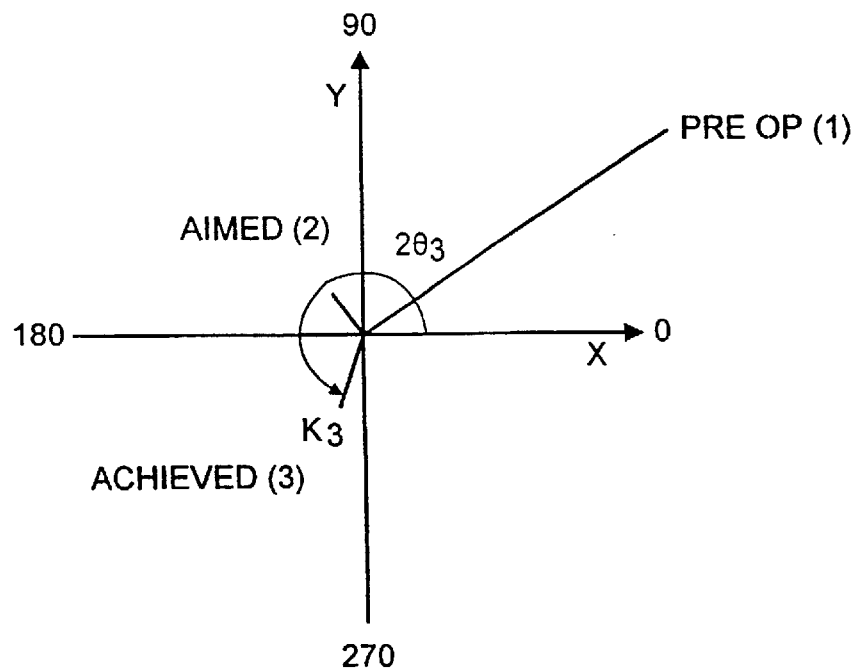

Doubling the angles ensures that results are examined in a 360° sense, so that rectangular coordinates may be used. Doubling the angles simplifies interpretation of differences between pre-operative, targeted or aimed and achieved astigmatic values, and is necessary in order to determine the magnitude and direction of the surgical vectors. FIGS. 2 to 4 show a double angle vector diagram in which the angles shown in FIG. 1 have been doubled.

In order to calculate angles and magnitudes, polar coordinates are first converted to rectangular coordinates as follows:

$X_1 = K_1 \cosine(2\theta_1)$ $Y_1 = K_1 \sine(2\theta_1)$ $X_2 = K_2 \cosine(2\theta_2)$ $Y_2 = K_2 \sine(2\theta_2)$ $X_3 = K_3 \cosine(2\theta_3)$ $Y_3 = K_3 \sine(2\theta_3)$ where: $X_1$, $X_2$ and $X_3$ are the X axis coordinates on a 360° vector diagram and $Y_1$, $Y_2$ and $Y_3$ are the Y axis coordinates.

Figure 5:
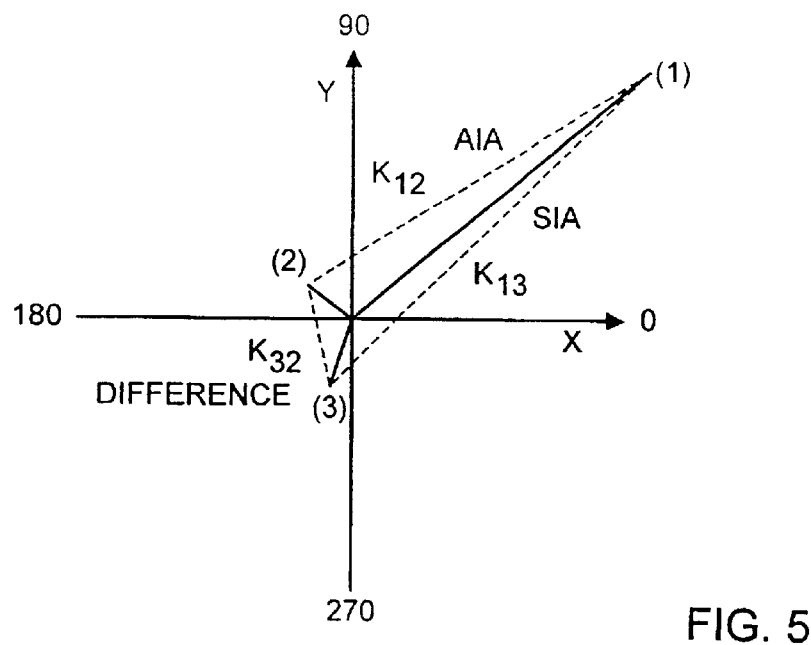
FIG. 5 is a diagram showing double angle vector diagrams and in particular showing a target astigmatism value, a target induced astigmatism vector and a difference vector.

FIG. 5 shows the Aimed or Target Induced Astigmatism (TIA) vector, the surgical Induced Astigmatism (SIA) vector and the Difference Vector.

The differences between the X and Y axis coordinates of the pre-operative (1), target (2) and achieved (3) astigmatisms are therefore:

$X_{12} = X_2 - X_1$ $Y_{12} = Y_2 - Y_1$ $X_{13} = X_3 - X_1$ $Y_{13} = Y_3 - Y_1$ $X_{32} = X_2 - X_3$ $Y_{32} = Y_2 - Y_3$

Double-angle values of the astigmatism vectors are calculated using the X and Y axis differences:

$$\Theta_{12d} = \arctan\frac{(Y_{12})}{(X_{12})}$$

$$\Theta_{13d} = \arctan\frac{(Y_{13})}{(X_{13})}$$

$$\Theta_{32d} = \arctan\frac{(Y_{32})}{(X_{32})}$$

The subscript d refers to double angle.

The arctangent calculation returns a value within the first and fourth quadrants. That is, it does not distinguish whether the angle is in a "to-from" or "from-to" sense. A 180° correction is required when the magnitude (see below) is calculated to be a negative value, as the required angle actually lies in the second and third quadrants.

The magnitude of the astigmatism vectors $K_{12}$ (TIA Target Induced Astigmatism), $K_{13}$ (SIA Surgically Induced Astigmatism) and $K_{32}$ (Difference Vector) can now be calculated:

$$K_{12} = \frac{Y_{12}}{\sine(\Theta_{12d})}$$

$$K_{13} = \frac{Y_{13}}{\sine(\Theta_{13d})}$$

$$K_{32} = \frac{Y_{32}}{\sine(\Theta_{32d})}$$

Both positive and negative values for $K_{12}$, $K_{13}$ and $K_{32}$ are possible. Negative values indicate, that the values of $\theta_{12d}$ and $\theta_{13d}$ need to be adjusted by 180°. Once such corrections to the angles are made, the absolute values of the magnitudes are used.

The above method of calculation differs from the method adopted by Jaffe and Clayman who used the Law of Cosines to determine the magnitude of the SIA as below (conformed for FIG. 5):

$K_{13} = (K_1^2 + K_3^2 - 2K_1K_3 \cosine 2 (\theta_1 - \theta_3))^{1/2}$

The problem with using the Law of Cosines is that the sign of the value calculated is not determinable and by convention is taken as being positive (i.e. the square root of the square of −4 is evaluated as +4).

The alternative method of calculation used here to determine $K_{12}$, $K_{13}$ and $K_{32}$ returns the same absolute value as that obtained via the Law of Cosines, but with either a positive or negative sign. A positive value indicates that the value calculated for $\theta_{12d}$, $\theta_{13d}$ or $\theta_{32d}$ does not require adjustment. A negative value means that the required angle is 180° different from that calculated, i.e. it lies in the second and third quadrants.

If the Law of Cosines is used, additional calculations and tests are required to determine when a 180° correction must be made to the double-angle value of $\theta_{12d}$, $\theta_{13d}$ or $\theta_{32d}$.

The calculated values for the vector angles $\theta_{12d}$, $\theta_{13d}$ or $\theta_{32d}$ are derived via the double-angle vector diagram. The actual vector angles are of half the size:

$$\Theta_{12} = \frac{\Theta_{12d}}{2}$$

$$\Theta_{13} = \frac{\Theta_{13d}}{2}$$

$$\Theta_{32} = \frac{\Theta_{32d}}{2}$$

Figure 7:
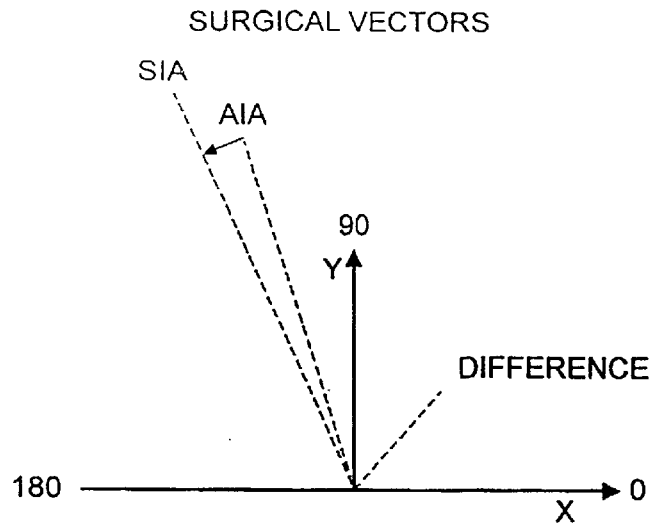
FIG. 7 shows a diagram in which the surgical vectors of FIG. 6 are analyzed.

The angle of error is expressed as being positive when the SIA vector lies further anti-clockwise than the TIA vector, and as negative if the change is further clockwise (see FIG. 7). The magnitude of error is expressed as a positive value if the SIA vector is larger than the TIA vector and as negative if smaller than the TIA vector.

The angle of error is most readily calculated from the double-angle values of the TIA vector and the SIA vector (FIG. 5). On the 0° to 180° single-angle vector diagram (FIG. 7), the angle appears as the angle between the vectors. However, if the absolute value of the $\theta_{error}$ is greater than 90 degrees, the angle is adjusted to bring it into the 0 to 90 degree range, by adding the smaller angle to 180° minus the larger angle.

The angle of error is calculated as:

$$\Theta_{error} = \frac{(\Theta_{13d} - \Theta_{12d})}{2}$$

The magnitude of the error is calculated as:

$$K_{error} = K_{13} - K_{12}$$

The difference vector represents the amount of astigmatic correction still to be induced to reach the targeted or aimed result from the achieved result; its corresponding orientation of action is from point 3 to point 2 (FIG. 5).

The angle of the difference vector is:

$$\Theta_{diff} = \frac{\Theta_{32}}{2}$$

The magnitude of the difference vector is:

$$K_{dLff} = K_{32}$$

Whereas the angle of error relates to the TIA vector and SIA vector, the angle of correction deals with the targeted or aimed and achieved astigmatism. The difference between the targeted or aimed and achieved astigmatism angles is defined as the angle of correction.

The angle of correction is:

$$\theta_3 - \theta_2$$

A positive value indicates that the result is counter-clockwise of the aim and a negative value means that it is further clockwise. The value is independent of the preoperative astigmatism.

Whilst the angle of correction is a measure of the final astigmatic result, it is not as useful as the angle and magnitude of error values in determining and comparing the success of astigmatic surgery.

The Coefficient of Adjustment adapts future astigmatism values to take account of a past trend of variance between the targeted or aimed and achieved astigmatism vectors. The coefficient of adjustment is:

$$\frac{K_{12}}{K_{13}}$$

The index of success relates to the magnitude of the differences vector and to the magnitude of the TIA vector.

Index of success:

$$\frac{K_{32}}{K_{12}}$$

The index of success can only be used if an attempt has been made to induce an astigmatic change in the eye.

Unlike astigmatism, vectors cannot be measured; they can only be calculated. Vectors are like surgical navigation aids. They indicate both the direction of future surgery and the success of past surgeries.

The difference vector is specific to the one eye in which it is calculated; however, utilizing the magnitude of this vector alone does provide a measure of the success of surgery, and can provide a useful basis for statistical analysis between multiple operations when axis direction is ignored. (This is similar to the current method of averaging SIA (Jaffe method) to determine mean total induced astigmatism for a series of eyes). It specifically represents the magnitude and axis of the difference in achieved. The angle is half that subtended on the double angle vector diagram; by placing its magnitude on a 180° chart, it would describe in a practical sense, the dioptric correction (the amount of steepening and its axis) required for a "top-up" operation to achieve the aimed result for that eye.

The magnitude in diopters gives a measure of the total vector distance between the aimed and the achieved results on the vector diagram.

Magnitude and angle of error are both standardized parameters that are measurable for, and directly comparable between, a series of multiple refractive surgery procedures and can determine the trend of a particular procedure. Mean and standard deviation values can be derived, providing statistical analysis. This method separates the components of the operative error, namely magnitude and axis, and indicates modifications to the original surgical plan required to achieve the aimed result, thereby enabling improved technique for subsequent surgery.

The success of a series of operations can be assessed by determining how close the mean magnitude and axis of error are to zero.

Methods of surgical technique currently employed to make separate alterations to magnitude and axis include:

For Magnitude changing the number of T-(tangential) cuts;

increasing or decreasing the optical zone size;

changing the length or depth of T-cuts;

altering the dimensions of the major or minor axes thickness of the ablatable mask in the excimer lasers employing these respective techniques.

For Axis
- changing the steepest axis by 90° by correcting astigmatism in excess of the preoperative magnitude;
- offsetting T-cuts from the steepest axis.

The potential exists for future excimer laser techniques, utilizing the TIA vector, to rotate the ellipse or the ablatable mask by a calculated amount from the steepest meridian of the corneal to achieve a nominated refractive and astigmatic aim.

a) Magnitude of Error

This is the difference in length or magnitude between the SIA (surgically induced astigmatism) vector and the TIA (aimed or target induced astigmatism) vector (FIG. 7). An over-correction has occurred if the SIA vector is longer than the TIA vector; an under-correction if it is shorter.

b) Angle of Error

This is half the angle substended on the vector diagram (FIG. 5) by the TIA and SIA vectors at the point (1) of the pre-operative astigmatism value. It can determine, in a series of eyes, for example if there is an error bias occurring towards a consistent axis, which is indicative of technique or machine error. Randomly spread error both positive and negative signs would suggest patient factors are more likely to be at play.

The sign of the angle indicates the direction in which the angle is in error; future corrective surgical action can then be adjusted accordingly.

Figure 6:
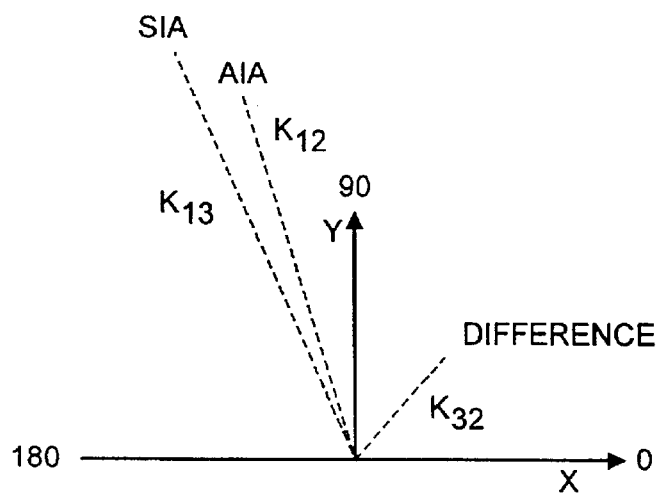
FIG. 6 is a view showing half angle surgical vectors.

The TIA vector and the SIA vector can be represented on a 180° diagram (FIGS. 6 & 7) by halving their respective angles; this determines the angle of error and its orientation. Here, the separation between the two vectors is the angle of error, and the correction of surgical axis direction required is from the induced towards the aimed.

The angle of correction is simply the angle between aimed and achieved astigmatism.

The angle of correction is zero if the aimed and achieved astigmatism axes coincide; the same can be said on the vector diagrams if the axes coincide on the same side of the zero co-ordinates. If the achieved and the aimed astigmatism differ in magnitude but coincide in axis there is a residual difference vector, angle of error and magnitude of error.

However, distinguishing between under and over correction according to the relative proximity of aimed or achieved astigmatism to pre-operative astigmatism would not appear to provide information of practical value.

A coefficient measuring the adjustment required to improve future surgeries can be derived from past surgical data, by dividing the TIA vector by the SIA vector. This coefficient can be averaged for a series of eyes. If it varies significantly from unity, a trend is apparent. If warranted, the magnitude of astigmatism to be corrected in future surgeries can be adjusted accordingly, to take account of the discernible trend. By multiplying the magnitude of the pre-operative astigmatism by the coefficient of adjustment, a magnitude parameter can be obtained, indicating treatment required to obtain the optimal surgical result.

A coefficient value of one indicates that there is no magnitude of error, and that there is no need to make this adjustment to future treatment. A value greater than one indicates that magnitude has been under-corrected; if the value is less than one, over-correction has occurred.

The index of success is a useful measure of the success of the surgery. It is proportional directly to the difference vector and inversely to the TIA vector. The ratio is independent of the size of pre-operative astigmatism. A value of zero on the index of success indicates complete success in achieving the surgical aim; and axiomatically the difference vector magnitude would also be zero. If only one of the angle of error or magnitude or error is zero, the index of success figure will be a number greater than zero. If the index might lie between 0 and one; for example, a value of 0.2 would indicate 80% success has been achieved in attaining the surgical goal. If the index of success is one, then surgery has resulted in achieved astigmatism being equally far away from the aimed as pre-operative astigmatism was. There may or may not have been an astigmatic change; either way the situation has been made worse because the eye has undergone surgery without improvement in its astigmatic state. The index of success can exceed one, indicating a result worse than the pre-operative state.

The index can only be used if the surgeon has attempted to change the astigmatic state of the eye. For example, in an eye that has a small amount of astigmatism associated with myopia, the surgeon may choose only to induce a spherical correction to correct the refractive error. In such as case, the index of success cannot be used.

Figure 8:
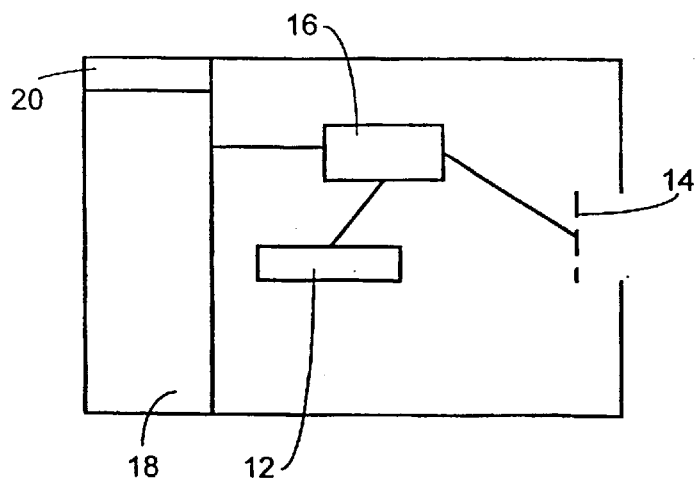
FIG. 8 is a schematic diagram of an apparatus for performing corneal surgery.

With reference to FIG. 8 an apparatus for performing corneal surgery is shown in schematic form. Such apparatus are generally well known and therefore the apparatus is not shown in full detail. The apparatus comprises a source of ultraviolet radiation 12 for producing a beam of ultraviolet radiation (193 nm) which will perform one or more cuts or contouring of a patient's cornea to change the astigmatic state of the patient's eye. A shutter 14 is provided for selectively allowing or shutting off the beam of radiation from the source 12. A control mechanism 16 is provided to control the intensity of the source 12 and also the opening time duration and the speed of opening or closing of the shutter 14 so that a beam of particular intensity for a particular time period can be provided. A microprocessor 18 is coupled to the control mechanism 16 and includes an input keyboard 20 for inputting data into the microprocessor. Data relating to the pre-operative astigmatism of the patient and the aimed astigmatism of the patient is fed into the keyboard 20 and the microprocessor 18 calculates a target induced astigmatism vector which is the difference between the targeted or aimed astigmatism and the pre-operative astigmatism and used as that vector to produce output commands to the control mechanism 16 for controlling the source 12 and shutter 14.

The microprocessor may also be programmed in accordance with the method hereinbefore disclosed to calculate the other parameters in accordance with the method of this invention for use in analysis and/or further surgery.

The astigmatic module for elliptical treatment patterns recently introduced for the Excimer laser has enabled the corneal shape to be changed in a precise and graduated manner to match the astigmatic refractive error. Current accepted practice is to treat the spectacle refraction adjusted for effectivity at the corneal plane, with secondary regard to the corneal shape. There is frequently a significant variance between spectacle and corneal astigmatism, and this becomes perplexing when one considers that differing readings are obtained with various types of keratometers according to the optical zone measured. The recent introduction of corneal topography technology has made this inconsistency more prevalent. Clearly, to obtain meaningful data, the same type of instrument should be used for all sequential readings: corneal topography, where available, is likely to become the preferred mode.

If the eye is treated using refraction as the treatment parameter, and there is a variance between corneal and refractive astigmatism, it is axiomatic that unavoidable non-zero corneal astigmatism will result. With astigmatic keratotomy, it is accepted practice to apply the tangential incisions at the steepest axis, with secondary regard to refraction: the same unavoidable consequence of non-zero astigmatism is conversely destined for refraction. After astigmatic keratotomy, it is not an infrequent occurrence to be satisfied with our surgical endeavors, using the keratometry reading as a criteria of success, and yet be disappointed that the patient may complain of symptoms such as monocular diplopia and oblique contours, or may still require astigmatic correction in their spectacles.

The cornea is a convex surface and is steeper in its vertical meridian when with-the-rule astigmatism is present—the axis of the convex cylinder lying at 180°. The clearest retinal image to this eye lies in the vertical meridian. Eggers has shown that this provides an advantage to visual acuity as measured by Snellen's type, as vertical strokes predominate in the English alphabet characters. Testing by a mathematical model confirmed that, for cases of mild myopia, viewing test objects from 0.5–6.0 meters, 0.50 D–0.75 D of with-the-rule astigmatism is optimal; resulting in the least amount of summated blur. The nasotemporal overlap of ganglion cells which supply both optic tracts are bilaterally cortically represented. They lie on the vertical midline raphe of retinal receptors and neuronal fibres, centered on the fovea, with a width extending greater than one degree of arc. This provides the mechanism to explain a much lower stereoscopic threshold for vertical objects than those orientated in any other meridian. Monocular clues for determining distance are obtained by utilizing parallax error between two objects, and this is achieved most frequently with vertical contour clues, such as light poles. In addition, the cyclodisparity range for fusion is greater for vertical than horizontal line segments.

We should state and write down our goals for astigmatism surgery, just as we do for many other tasks, to enable us to assess our success or shortcomings in achieving our initial aims. By stating our astigmatic goal, we are able to determine how the SIA Vector differs from the TIA Vector. Comparative analyses of surgery, utilizing this concept of vector analysis is then made possible, because we can determine differences and errors, and thereby ascertain the correction required for future surgeries. The more accurate and predictable the surgery; the narrower will be the spread of the results.

The concept of the TIA Vector is the key to future astigmatism surgery, utilizing techniques such as the Excimer laser. As mentioned earlier, the tendency of past and present techniques of astigmatism surgery is to aim to achieve zero astigmatism, by effectively utilizing a TIA Vector force equal in magnitude to the pre-operative astigmatism and at 90° to the axis of the astigmatism. The cornea is flattened in the meridian of the astigmatism, with a net steepening in the direction of the TIA Vector.

It is likely that zero astigmatism will continue to be the astigmatic goal, but aiming for zero astigmatism is a self-imposed limitation that may no longer be necessary or reasonable because of the subtleties afforded us by new technology. Any desired post-operative astigmatism may be sought, such as, for example, 0.5 D–0.75 D with-the-rule for the reasons given above. By utilizing the TIA Vector calculated, the required surgery can be keyed in to the appropriate software program of the Excimer laser to achieve the intended corneal toroidal shape.

Non-zero astigmatism is an ineluctable consequence of the conflict between a variance of refractive and corneal astigmatism. A dilemma exists as to whether the corneal shape or the refraction should be the primary determinative factor addressed in any mode of astigmatism surgery. The method addresses how this dilemma can best be resolved by pre-operatively assessing the least unfavorable result for the secondary surface, to which unavoidable astigmatism will be directed. This can be done by analyzing what the astigmatism consequence would be for each surface if a TIA Vector were applied to achieve zero astigmatism at the other surface. The surgeon can then select the preferable TIA Vector to be applied (or a suitable compromise between the two calculated), so that the refractive surface(s) destined to receive non-zero astigmatism is (or are) altered in the most optically and physiologically favorable orientation. The surgeon may choose to preoperatively select the primary treatment that directs the secondary result closest to with-the-rule astigmatism, with the steepest refracting axis closest to the 90° meridian. Without calculating and specifying a non-zero goal(s), we are unable to determine how successful our astigmatism surgery has been.

The ability to calculate the angle of error accurately now exposes the weakest link in our refractive surgery armamentarium—our inability to identify the steepest corneal meridian precisely by real-time topography through the operating microscope during surgery. Achieving this would enable accuracy in applying treatment to approach the accuracy we possess in measuring and calculating the treatment parameters.

The method described herein provides the astigmatism surgeon with additional information not previously available, enabling a mathematically precise evaluation of surgery, using parameters which will allow comparison both between different eyes and different techniques. These parameters also enable the surgeon to ascertain the means of attaining any desired level of post-operative astigmatism. It is only by meaningfully and critically analyzing our astigmatism surgery that we will be able to improve it. Now that we can determine specific errors, we are provided with the means of correcting each component of our error separately. By being able to make better use of current technologies we will achieve better control and ultimately, more accurate surgery.

Hereafter, the resolution of the problems in correcting astigmatism taking into account measurements made topographically and refractively will be explained in detail.

In a randomly chosen population of 100 patients who underwent PARK surgery, the patients were screened prior to surgery and their pre-operative parameters were determined.

The refractive astigmatism (R) at the corneal plane is determined by manifest refraction with Jackson cross-cylinder confirmation performed in a standard refracting lane, with the appropriate correction for back vertex distance and the associated myopia. This was found to be a mean 1.69 D, SD 1.03 D, range 0.39 D to 5.15 D. The topographic astigmatism (T), as determined by the Simulated Keratometry value utilizing the TMS Topographic Modelling System (Computed Anatomy, Inc., New York, N.Y.), showed a mean 1.83 D, SD 0.96 D, range 0.2 D to 5.5 D. The mean absolute difference between T and R values of pre-operative magnitude was mean 0.58 D, SD 0.46 D, range 0.00 D to 2.30 D and the axis was 11.93°, 12.03 SD, range 0 to 78°. The magnitude of astigmatism measured topographically exceeded the magnitude of astigmatism measured refractively in 59 patients, and the magnitude of refractive astigmatism exceeded the magnitude of astigmatism measured topographically in 41 patients.

Figure 9:
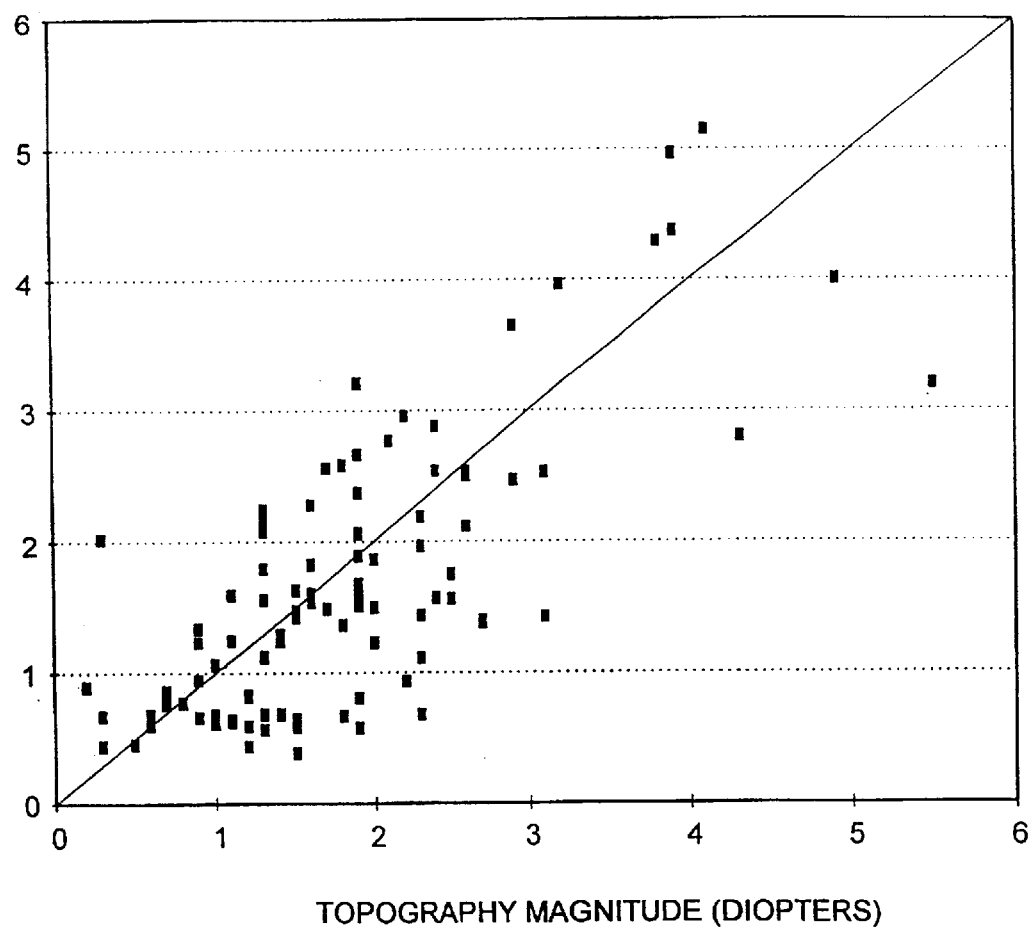
FIG. 9 is a graphical illustration showing magnitude of astigmatism measured refractively and topographically for 100 random study patients.
Figure 10:
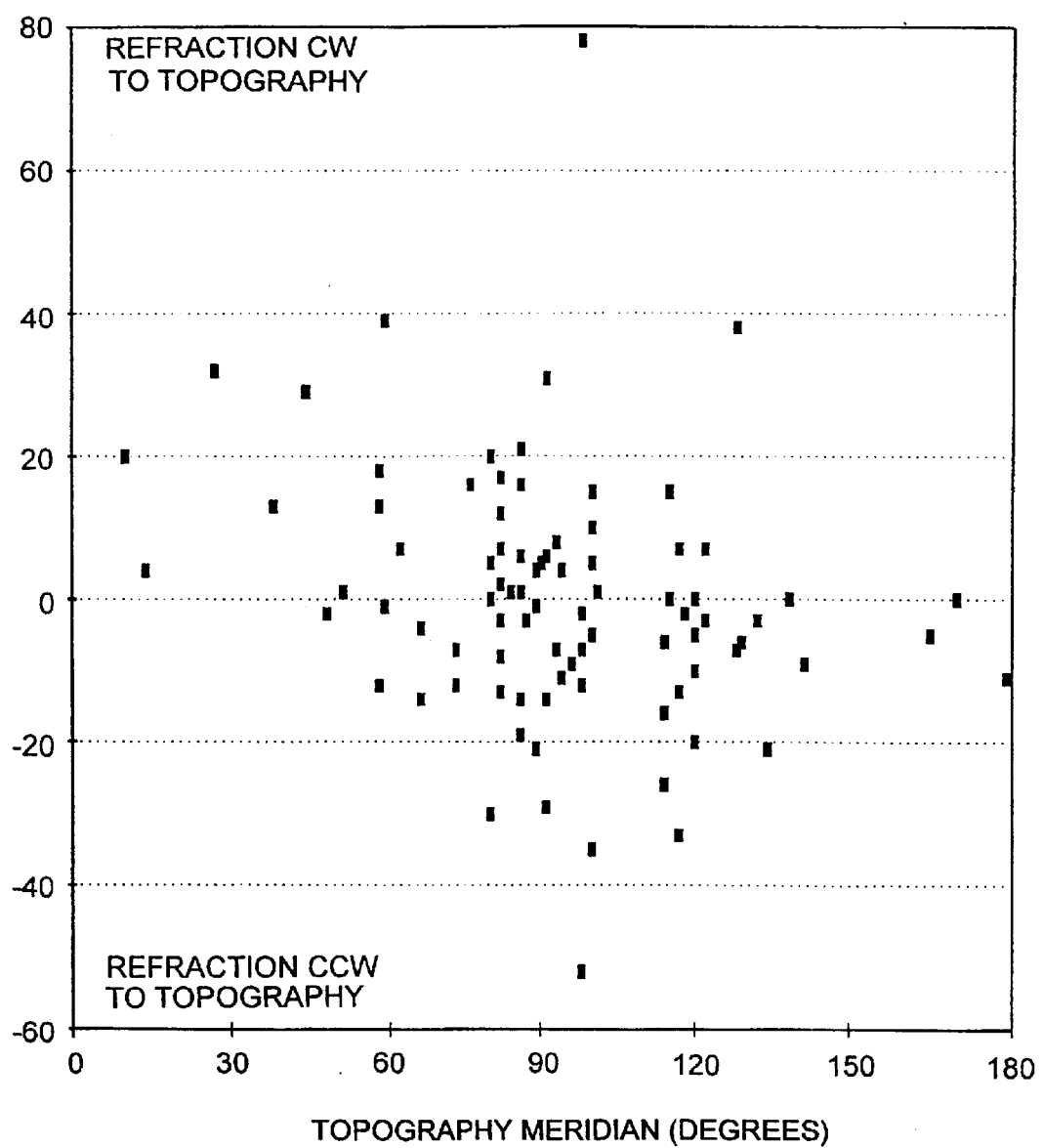
FIG. 10 graphically illustrates axis variance relative to topography meridian for the patients.
Figure 11:
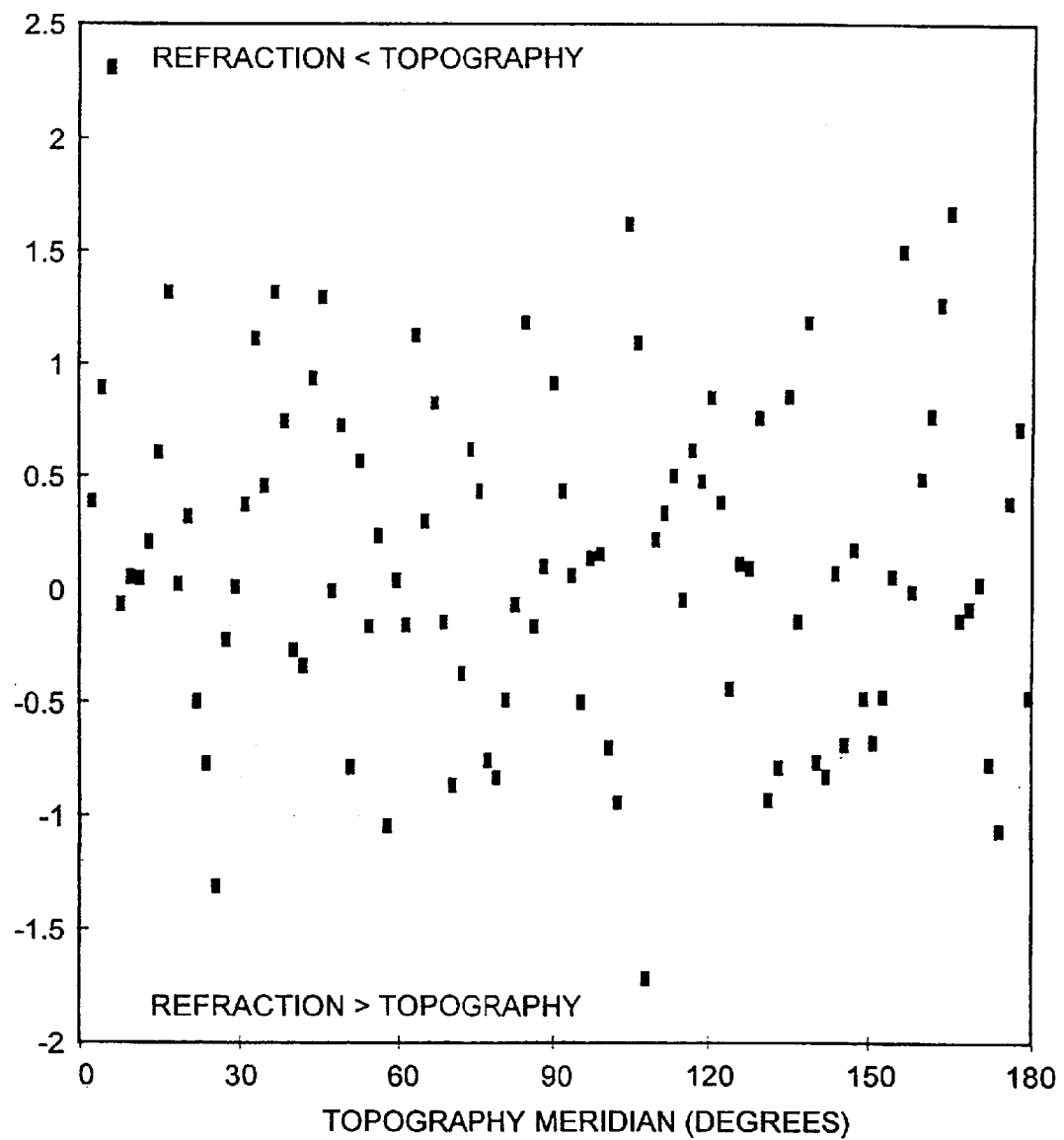
FIG. 11 graphically illustrates magnitude variance relative to topography meridian for the patients.

Scatterplots of the refractive versus topographic astigmatism magnitude values are shown in FIG. 9 and indicate the trend for topography to exceed refraction (corneal plane) values. The axis variance between topography and refraction values shows no clockwise or counter-clockwise trend (mean +0.57°; SD 16.97°; range −78° to +52°. A scatterplot shown in FIG. 10 displays this variance in relation to topographic axis; positive values indicate refraction to be clockwise to topography and negative values counter-clockwise. The magnitude variance between topography or refraction is displayed on the scatterplot in FIG. 11 compared to topographic axis.

Figure 12:
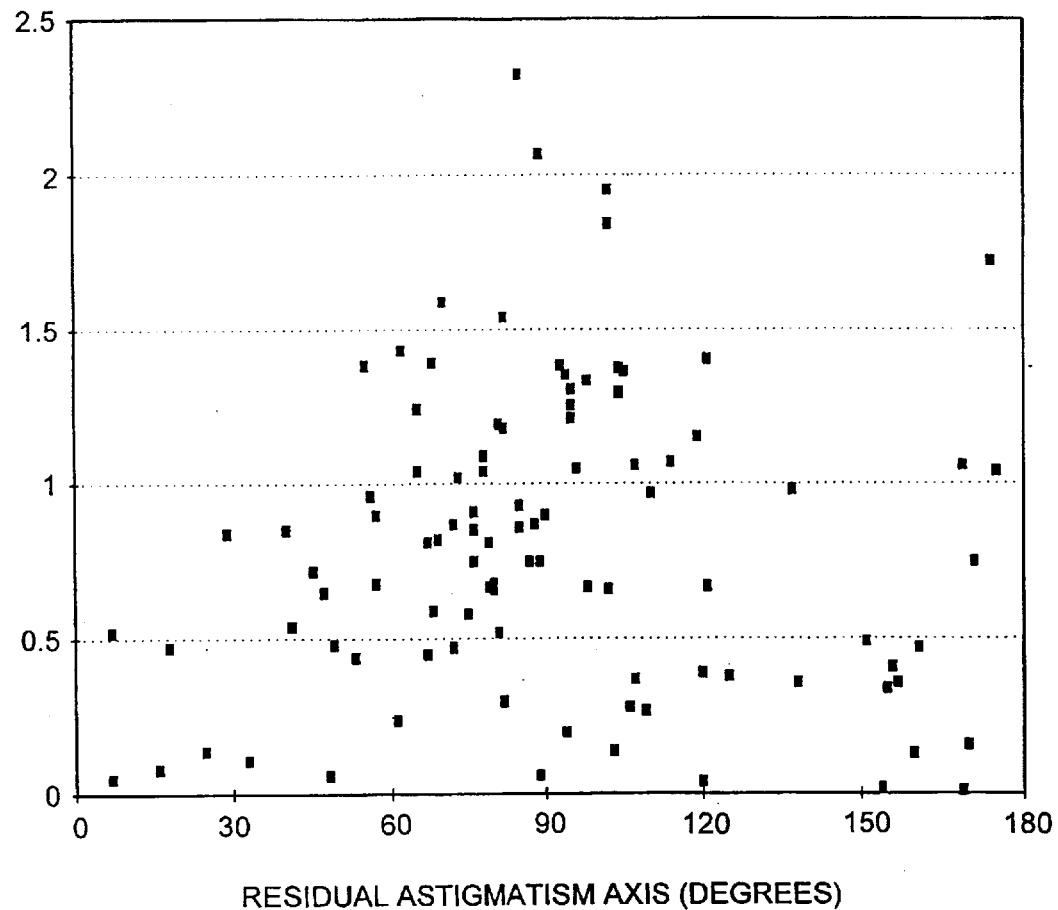
FIG. 12 graphically illustrates residual astigmatism for the patients.
Figure 13:
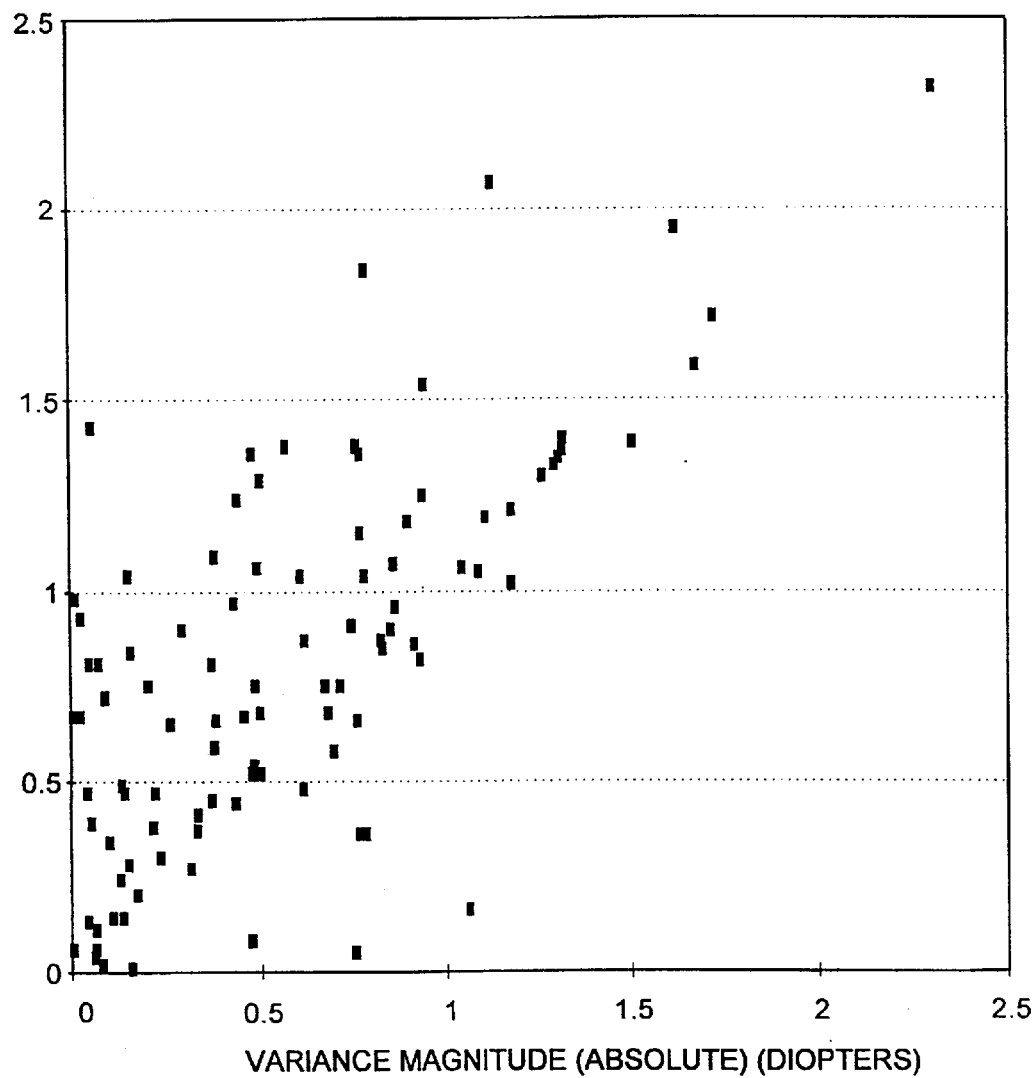
FIG. 13 graphically illustrates magnitude of residual astigmatism vs. magnitude variance for the patients.
Figure 14:
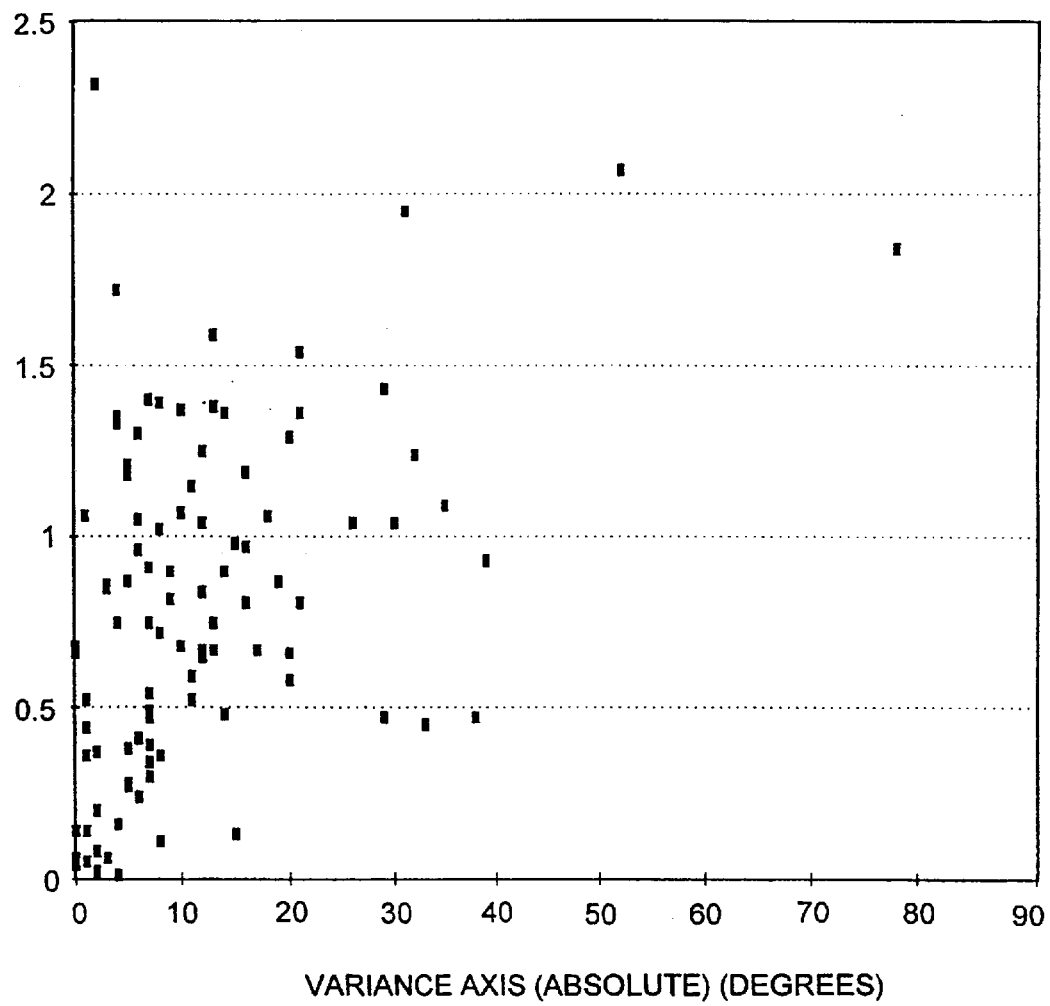
FIG. 14 graphically illustrates the magnitude of residual astigmatism vs. axis variance for the patients.

The residual astigmatism is a combined measure of axis and magnitude variance between the refractive and corneal astigmatism. The magnitude and orientation values are illustrated in FIG. 12, with a trend to greater frequency and magnitude in the 60°–120° range. A scatterplot of the residual astigmatism magnitudes versus the magnitude variances as shown FIG. 13 and the axis variances as shown in FIG. 14 of each patient shows a trend of linearity in their relationships. The residual astigmatism R for the group as determined by vector analysis has a mean 0.81 D, SD 0.49 D, range 0.01 D 2.32 D. The residual astigmatism exceeded 1.00 D in 34 patients, and 7 of these exceeded the pre-operative magnitude of topographic astigmatism. When surgically treating by refractive astigmatism parameters alone, this astigmatism would be targeted onto the cornea, which in the latter group would be targeting an increase in the existing corneal astigmatism. Hence, if zero residual astigmatism is targeted based on topography or refractive measurements alone, the achieved astigmatism following surgery on the basis of the selected class of measurement may approach zero, but the astigmatism measured by the other class can remain high and even exceed the originally measured astigmatism. The invention seeks to provide a surgical treatment method which takes into account both refractive and topographic astigmatism measurements.

An example is given hereafter to assist in gaining the required understanding of the method of the invention in which vectors are analyzed for the planning of astigmatism surgery. An apportionment of total target astigmatism into its topographic and refractive components, and the methodology for choosing the targeted induced astigmatism (TIA) in order to achieve a minimum target astigmatism measured refractively and topographically, is described and illustrated. Various modes of optimal and asymmetrical treatment are proposed.

FIG. 15a illustrates an example of a cornea with differing values of magnitude and orientation of refractive (corneal plane) and topographic astigmatism R and T respectively. The orientation of the refractive astigmatism R is graphically illustrated at the power meridian of the negative cylinder (or the cylinder axis of the positive cylinder), to facilitate refraction and shape comparisons. All examples containing refractive astigmatism values are calculated using both "plus" and "minus" cylinder notation. Each of the steepening forces required to correct astigmatisms T and R respectively, are the target induced astigmatism (TIA) which are equal in magnitude and orientated at 90° to each respective astigmatism T or R. Thus, as shown in the box in FIG. 15b, the astigmatism T measured topographically is 1.70 D at axis 120 and the TIA is 1.70 D at axis 30 to produce a target residual value of zero (considering topography alone) whereas the astigmatism R measured refractively is 1.40 D at axis 107 (for plus cylinder refraction) and the TIA is 1.40 D at axis 17 to produce a target residual value of zero (considering refraction alone).

Each of the two astigmatisms T and R are displayed as vectors on the double-angle vector diagram of FIG. 15b and each TIA is now opposite, i.e. orientated at 180°, to the respective astigmatism, T and R. The vectors TIA for measurements by topography (TIA T) and for orientation (TIA R) show the force and its orientation necessary to sphericize the cornea topographically or refractively. The residual astigmatism ($^K$TR) is the vectorial difference between the total astigmatism as measured by refraction at the corneal plane, and the corneal astigmatism as measured by topography values:

$^K$TR=$^K$R. $^K$T

The value of $K_R$−$K_T$ $^K$TR in the example is 0.76 D Ax 147°.

The refractive effect of choosing a TIA to sphericize the cornea (TIA T) can be ascertained by vectorially adding that TIA to the pre-operative refraction to determine the target refraction R as shown in FIG. 16a. The target refraction R has the same magnitude as the residual astigmatism and lies parallel to the line displaying it. Similarly, the topographical target astigmatism can be determined by vectorially adding the vector TIA R to the topographically measured astigmatism T to achieve a summating or combining of the spherical refraction and the pre-operative topography. The arrows in FIGS. 15b, 16a, 16b indicate the direction of the vectors.

The residual astigmatism is equivalent in length and orientation to the maximal correction target line in FIG. 17a. The magnitudes of the residual astigmatism in FIG. 15, the target refraction, FIG. 16a and the target topography FIG. 16b, minimum target astigmatism FIG. 17a and maximal correction target line in FIG. 17a are all equal, and all lines representing these values are parallel to each other, as evidenced by the parallelograms formed by joining the vectorial combinations.

In other words, when the target induced astigmatism determined topographically (TIA T) is vectorially added to the vector R of astigmatism values measured refractively to obtain the residual astigmatism shown in FIG. 16a, this residual astigmatism is equal to the residual astigmatism in FIG. 16b which is the vector sum of the astigmatism values T measured topographically and the target induced astigmatism determined refractively (TIA R). Moreover, the residual astigmatism values determined in FIGS. 16a and 16b, which are equal to one another, are also equal to the maximum correction target line in FIG. 17a where the chosen TIA is intermediate TIA T and TIA R. In accordance with the invention, by observing the above conditions, the total residual astigmatisms T and R measured topographically and refractively following surgery will be a minimum. Essentially, when the TIA is between TIA R and TIA T its magnitude is established by the vector having one end at the origin and whose other end is on the maximal correction target line.

The intermediate TIA in FIG. 17a can be chosen between the boundaries of the TIA T and TIA R and its vector length terminates on the maximal correction target line. The relative proximity of the intermediate TIA to topography astigmatism values T and refraction astigmatism values R determines the emphasis of treatment shown in FIG. 17b. Any TIA utilized which achieves the minimum target astigmatism for the prevailing topographic and refractive parameters must terminate on this line. Any chosen TIA can then be applied to both refraction and topography (as in FIG. 17a) to leave the minimum target astigmatism, which is apportioned between topography and refraction according to the chosen emphasis. The target refraction and topography are orientated at 180° to each other on the double angle vector diagram; that is, they form a straight line, and hence their total magnitudes are a minimum for the optical system of that eye. In FIGS. 17a and 17b, the total astigmatism values of T and R are 0.76 (0.50+0.26 in FIG. 17a and 0.28 and 0.48 in FIG. 17b).

Figure 19:
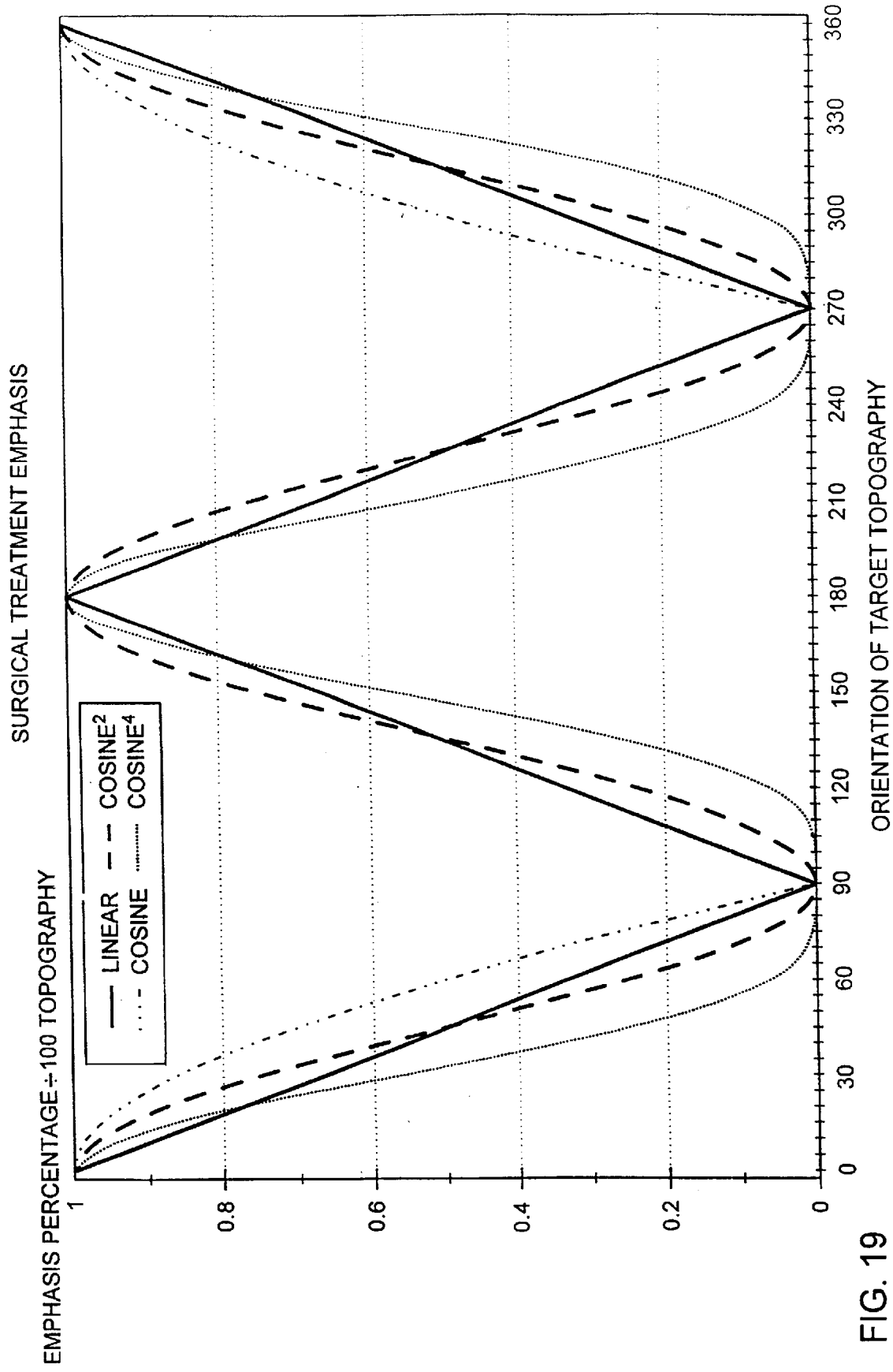
FIG. 19 graphically illustrates variation of surgical treatment emphasis for different paradigms.

The parameter that best determines the optimal point of termination of the TIA with the emphasis line (where it intersects the maximal correction target line) is the orientation of the target corneal astigmatism. In this example, the meridian or target topography is 147°. As this lies 57° from a with-the-rule orientation of 90°, the surgeon may decide to use a linear relationship as illustrated in FIG. 19 and apportion 57/90 or 63.3% emphasis to a-topography-based treatment goal. Consequently, the TIA (FIG. 17b) will be positioned in relative proximity to the TIA T vector (FIG. 16a) compared to the TIA R vector (FIG. 16b). In the box associated with FIG. 17b, the emphasis is 63% topographically and 37° refractively. This determines the parameters for TIA and the target astigmatism values for R and T.

If a TIA is chosen without regard to the maximal correction target line this will result in a total target astigmatism (T plus R) greater than the minimum. When the TIA is longer than if it terminated at the maximal correction target line "overcorrection" will be obtained as illustrated in FIG. 18a. The two values of target astigmatism T and R are determined by applying the TIA to the pre-operative topography and refraction values and when the two target values T and R are added together, the result is 0.54+0.58=1.12 which is greater than the minimum target astigmatism of 0.76, and when compared to each other a linear (180°) relationship is not present. Thus, as seen in FIG. 18a, the angle between T and R is not 180° (86°), whereas in FIGS. 17a and 17b the angle is 180° and T and R lie on a straight line.

Similarly, if a TIA is chosen that is shorter than that required to reach the maximal correction target line (FIG. 18b) the sum of T and R will be 0.30+0.63=0.93 which greater than the minimum value of 0.76. This may, for example, be the case where the refractive magnitude is chosen with the topographic meridian, to "under-correct" the astigmatism. The resultant target astigmatism (T & R) is again greater than the minimum achievable as the angle between T and R is not 180° (51°). A full correction of astigmatism is only achieved when the TIA employed targets the minimum astigmatism that is equal to the residual astigmatism (as in FIGS. 17a and 17b). The target astigmatism in excess of the minimum increases hyperbolically as a function of increase of the distance of the end of the line representing the chosen TIA from the maximal correction target line.

Note that in this context as illustrated in FIGS. 18a and 18b "over" and "under" corrections do not refer to the relative relationship between SIA and TIA, but a comparison between the targeted change and what might be a preferable choice. It is also to be noted that when the astigmatism values T and R measured topographically and refractively are different in magnitude and/or axis, the refractive and topographic target astigmatism values T and R are non-zero and the sum of their vectors is equal and parallel to the vectorial difference between astigmatism values T and R and respective TIA R and TIA T values as shown in FIGS. 17a and 17b. This is referred to as "summating" the astigmatism values T and R measured topographically and refractively.

The emphasis of treatment is the relative position between any targeted topographic and refractive goals, expressed as a percentage. When these goals are both zero, the maximal correction of astigmatism is possible as the emphasis line coincides with the maximal correction target line. The treatment emphasis can only be apportioned when the TIA terminates at its point of intersection with the emphasis line.

The emphasis paradigm chosen in FIGS. 17a and 17b follows linearity as represented graphically in FIG. 19. For the refractive surgeon, a decision is to be made in the choice of emphasis of treatment. The majority of current astigmatism surgery using incisional or non-incisionally techniques is performed with the chosen TIA at either end of the emphasis line. Preferably, a choice should be made as to how much emphasis is given to topography or refraction in the surgical plan, according to the orientation of the target astigmatism. The surgeon may choose an emphasis that adheres to linearity, to the square of the cosine of the target astigmatism, or to another function of cosine. The lower the line on the graph in FIG. 19, the more the emphasis given to refraction. Alternatively, the surgeon may choose to vary the treatment emphasis according to prevailing knowledge or understanding of how much degradation is imposed upon the visual image according to the orientation of the existing corneal astigmatism. The effect on the quality of this perceived image is also likely to vary according to the associated spherical equivalent. In the example given for FIG. 17b, the selected paradigm is a "with the rule" orientation for the residual astigmatism. The axis of 147° for target astigmatism (topographically) is taken on the abscissa in FIG. 19 and this intersects the linear emphasis line at an emphasis of 63%. This value of 63% is selected for topography and 37% for refraction. The resultant TIA is plotted in FIG. 17b and its parameters are given in the appended box.

Hereafter the invention will be described with reference to eyes having a non-symmetrical topography wherein analysis and treatment will be made on respective superior and inferior hemi-divisions of the eye.

Referring to FIG. 20a, therein it is seen that the eye is divided into superior and inferior hemi-divisions, each having respective topographical astigmatism values which differ from one another. The refractive astigmatism values are measured for the entire eye and accordingly are the same for the two hemi-divisions.

The optimal treatment described with reference to FIGS. 15a, 15b and 17b is shown on the superior hemi-division of the cornea in FIG. 20a. Note that this is a single angle astigmatism and surgical vector diagram, illustrating the parameters as they would appear schematically on an eye, as in FIG. 15a. Employing polar co-ordinates does not allow for vectorial comparisons of astigmatism provided by the double angle vector diagrams as in FIGS. 15b, 18a, 18b. In the two examples in FIG. 20a, the emphasis in the surgical plan given to topography follows the linear relationship in FIG. 19. The closer the target astigmatism approaches against-the-rule, the more the emphasis is given to topography in the surgical plan to achieve a spherical cornea, thus targeting less unfavorable corneal astigmatism.

Where treatment differs between the two hemi-divisions of the cornea, a separate evaluation is required to determine the effect on refractive astigmatism of the two differing TIAs applied to the corneal shape. Resolution of the treatment vectors (FIG. 20b) is required when performing hemi-meridian treatment of astigmatism, so that the change in refractive astigmatism is the vector sum of the two treatment components of the superior and inferior hemi-divisions. One half of the vector sum of the TIA topography parameters of the superior and inferior halves is vectorially applied to the refractive astigmatism value in both hemi-divisions as shown in FIG. 20c.

The values in the parentheses in the boxes in FIG. 20a for target refractive astigmatism in the superior and inferior divisions are each determined for the case where a single topography value exists, either superior or inferior values for both divisions of the cornea, as if the cornea were symmetrical. In this example, it can be seen that the orientation of these two refractive values, being separated by close to 90°, results in the single target value calculated from the resolved treatment vector being smaller than each individual target value.

Hence, according to the invention a TIA net value is obtained by vectorially averaging the TIA values obtained from the superior and inferior hemi-divisions, said TIA values being based on the pre-operative astigmatisms T and R respectively, and the emphasis in each hemi-division. The TIA net is then taken globally with the pre-operative astigmatism R measured refractively to obtain the non-zero-target astigmatism measured refractively.

The invention will next be described with reference to treatment in which the axis of astigmatism is shifted without changing the magnitude of the astigmatism. This treatment is in the nature of application of an "astigmatic torque" to the eye.

A force applied to the eye, having existing corneal astigmatism, at an oblique angle of 45° to the astigmatism axis will exert a purely torque effect and have no steepening or flattening effect on the original astigmatism axis. The effect of this force on astigmatism can readily be appreciated on the double angle vector diagram as shown in FIG. 21b, where the target astigmatism increases in magnitude as the tangential force applied increases. As torque force exerted increases, so does the pre-operative axis shift, up to a limit of 45°, which is in the direction of the torque force. Referring to FIGS. 21b the following relationships are seen.

$$X1 = K_1 \text{ cosine } (2\theta_1)$$

$$Y1 = K_1 \text{ sine } (2\theta_1)$$

$$X2 = K_2 \text{ cosine } (2\theta_2)$$

$$Y2 = K_2 \text{ sine } (2\theta_2)$$

The axis and magnitude of the astigmatism vector on the double angle vector diagram are determined from the relation:

$$\text{TIA axis} = \arctan \frac{Y_2 - Y_1}{X_2 - X_1}$$

$$\text{TIA magnitude} = \arctan \frac{Y_2 - Y_1}{\text{sine (TIA) axis}}$$

The magnitude of the astigmatism torque force (TIA torque):

$${}^K\text{TORQUE} = K_2 \text{ sine } (2\theta_2 - 2\theta_1)$$

If the result is positive the force is in a counter-clockwise (CCW) direction and if negative it is clockwise (CW).

The amount of flattening/steepening that has occurred with respect to the pre-operative astigmatism axis is expressed as follows:

$$^K\text{FLATTENNING/STEEPENING} = K_2 \text{ cosine } (2\theta_2 - 2\theta_1) - K_1$$

In this example the value of $^K$FLATTENNING/STEEPENING is taken as zero if there is no flattening/steepening effect to be obtained. If the value was positive then steepening has occurred, and if negative flattening has occurred.

Where only a change in meridian is desired and no change in magnitude of the astigmatism is targeted, any change in the orientation of astigmatism requires an amount of flattening in combination with the TIA torque. The greater the change in orientation, the greater the proportion of flattening force and the less the torque. At the limit of change of axis, which is 180°, the force required is wholly a flattening one, and the torque component becomes zero.

It is useful to divide the change into its two component parts one being either flattening or steepening, and the other torque. This is an essential consideration when differences exist between topography and refraction, as for example, a refractive cataract surgery incision placed "on axis" for flattening of one modality will be "off axis" for the other, and will have a torque as well as a flattening effect on its magnitude. When performing non-incisional refractive surgery, a treatment will have a flattening/steepening and torque effect on one or both modalities, as it may not be aligned with either T or R axis.

The effect of flattening and steepening on torque and the compensating effect to achieve astigmatic torque without flattening and steepening will be described with reference to FIGS. 22a, 22b, 23a and 23b.

Referring to FIGS. 22a and 22b =the amount the TIA is "off-axis" from the steepening force required to reduce the existing astigmatism:

$$^K\text{TORQUE} = TIA \text{ sine } 2$$

In FIGS. 21a, 21b, 22a, 22b the effect of steepening or flattening produced by applying a torque force at 45° to the astigmatism axis (90° in the double angle vector diagram) is compensated by angularly shifting the TIA by an angle 90-2 (FIG. 22b), to obtain torsional rotation without change in magnitude. In the numerical example, the astigmatism has a magnitude of 1.40 D and the axis is shifted from 8 to 25° and to achieve this the TIA has a magnitude of 0.83 and an axis of 62°. The effect of steepening, flattening, CW torque and CCW torque applied to the pre-operative astigmatism by the TIA force at the respective orientations is illustrated in the Figures.

When examining the change that has occurred at the intended axis of the astigmatism surgery, the flattening/steepening effects of surgery can be determined by the relationship illustrated in FIGS. 23a and 23b. The angle φ is subtended between the SIA (surgically induced astigmatism) axis, and the TIA axis 90° to the axis of the incision.

$$^K\text{FLATTENING/STEEPENING} = SIA \text{ cosine } 2\phi$$

The method can be applied to determine the astigmatic effect of a cataract surgery incision (SIA) at its meridian of placement. The flattening/steepening component of the SIA determined by this means utilizing surgical vectors, provides an alternative formula to achieve the same magnitude value as that calculated by the formulas for the meridional power of cylindrical lenses and surfaces employed by Holladay and Naeser. The above formula is directly linked to the SIA and the angular deviation from its intended meridian of placement, the angle of error. This eliminates the requirement when determining meridional power, of calculating the contribution of the pre- and post-operative astigmatism on the surgical meridian and at 90° to it, followed by subtracting one net value from the other to determine the change at that incision's axis.

The description of this change by either of the terms flattening or steepening, according to the corneal change at the surgical meridian, may provide some advantages of simplicity to the descriptive terms "with and against-the-wound", and "with and against-the-power". However, the terms "with-the-rule" and "against-the-rule" refer to polarity at the specific meridia at 90° and 180°, and are in common accepted usage.

In the example in FIGS. 24a and 24b, a torque force is applied to the entire cornea with orthogonal symmetrical astigmatism, to target the refractive cylinder axis. Any induced change of the corneal shape would target an equivalent vectorial change on the refractive modality, and one would expect the refractive cylinder to have rotated by the appropriate amount of the corneal change induced by that force. When treatment is symmetrical no resolution of treatment vectors is necessary.

Next will be explained the treatment of irregular astigmatism referring to FIGS. 25a and 25b.

Irregular astigmatism is present where topographic values of the two hemi-divisions of the cornea do not coincide either in magnitude (asymmetry) or meridian (non-orthogonal) or both. Existing differences of some order between the two halves of the cornea are widely prevalent. The topographical disparity is a measure of astigmatism irregularity in diopters, by vectorially comparing the topographic values of magnitude and axis between the two corneal hemi-divisions. For this example the topographic disparity is 1.29 D.

In the presence of either non-orthogonal or asymmetrical astigmatism or both, there may be a desire to regularize the corneal shape to provide the opportunity for improved unaided or best-corrected vision. It may be advantageous to have the ability to perform this task without any net change in refractive astigmatism or spectacle correction. By treating the cornea in two independent halves, the appropriate amount of astigmatic change can be applied at the appropriate meridia for the desired change in topographic astigmatism, in opposite cyclical directions. The existing topographical astigmatism can be targeted to coincide in both magnitude and meridian (actually 360° apart) on the double angle vector diagram, to create the orthogonal state (180° apart) on an astigmatism diagram of the eye. Resolution of the two treatment vectors shows that the two TIAS, when applied in equal magnitudes and at 90° to each other, negate each other's effect and cancel any net effect on refractive astigmatism.

Reduced vision due to apparent amblyopia or other causes of sub-optimal vision associated with irregular astigmatism may benefit from improved unaided and best corrected vision by regularizing the cornea. It is possible that lower grades of keratoconus may also benefit from differential flattening and steepening on the opposite hemi-meridian to reduce or eliminate the existing asymmetry of the condition.

This method of changing the topography of the eye without any net effect on the refractive astigmatism can also be employed with purely flattening and steepening or torque effects.

The correction of irregular astigmatism to an orthogonal symmetrical state may be achieved in other ways. This may be achieved by the application of treatment to a single hemi-division of the cornea, as in FIGS. 26a and 26b (The TIA for the inferior hemi-division is zero). In this example, by moving the less favorable astigmatism to coincide with the more favorably placed hemi-meridian closer to a with-the-rule orientation (180°/540° on the double angle vector diagram, the result is an improvement in the orientation of both the shifted superior hemi-meridian of the corneal astigmatism and the refractive astigmatism with the least change to achieve regularity. One half of the net TIA effect is applied to each half of the refractive astigmatism. No change of the inferior topographic hemi-meridian is targeted.

The topographic astigmatism of the eye can be improved by rendering it orthogonal and symmetrical in another manner as shown in FIGS. 27a, 27b and 27c. By targeting the refractive magnitude and axis for the topography in both hemi-divisions of the cornea, a net reduction in the amount of residual astigmatism will result from a decrease in the amount of disparity between topography and refraction in each corneal half. There may be a shift of the refractive astigmatism that is induced by the net TIA determined by resolving the superior and inferior treatment vectors. The resultant residual astigmatism of both hemi-divisions will be equal and at minimal levels.

Referring to FIGS. 28a, 28b and 28c, these show that the TIA can be determined to change the prevailing refractive or topographic astigmatism to any desired target. The topographic change can be symmetrical or asymmetrical. In this example, both hemi-meridia of the cornea are targeted at 0.75 in a with-the-rule orientation (90° & 270°) to render the cornea symmetrical. After resolution of the treatment vectors, it can be seen that there is a net favorable shift in the refractive astigmatism, with a reduction in its magnitude and the amount of residual astigmatism.

FIGS. 29a, 29b, 29c show a treatment to achieve any desired nominal corneal astigmatism where there is no apparent relation between the corneal shape in the hemi-divisions. Thus, the target astigmatism of both hemi-divisions represent two randomly chosen targets. The TIA vectors are separately calculated for each of the chosen targets. The net TIA is obtained by vectorially adding the TIA values in the hemi-divisions. This could have benefits not immediately predictable at the present but which could have future benefits in different surgical techniques and to achieve different optical effects based on retinal and optic nerve investigations.

The separation of the differing forces of flattening/steepening and torque, and the treatment of the cornea as the two significantly differing halves (as it frequently is), provides the ability to change the relative shape of the cornea in various ways. The ability to achieve orthogonal and symmetrical topographic astigmatism, either affecting the refractive astigmatism in a favorable way, or not necessarily changing it at all, enables a potential and significant expansion in the means to produce astigmatic enhancement and improved visual performance.

Hereafter, the invention will be discussed further with reference to a series of topical headings as follows:

1. A concept for undertaking astigmatism analysis.
2. The optical correction of astigmatism.
3. Objective and Subjective analyses.
4. Adjustments and Nomograms.
5. A computer Assisted Video Keratotomy (CAVK)
6. Keratoconus.
7. Vector Analysis Vector.
8. Common principle—Target T and R.
9. Optical treatment of astigmatism.
10. Emphasis.
11. Complexities and Considerations of Corneal Shape.
12. Astigmatic torque.
13. Quantitative Surgical Planning.
14. Vector Change Maps.
15. Conclusion.

1. A Concept for Understanding Astigmatism Analysis

Any new concept that expands existing understanding of a subject requires many qualities to gain general acceptance.

First and most importantly, the underlying concept should be simple to understand. Any inadequacy in past understanding of a subject should readily become apparent. New information provided by the introduction of a concept should be useful and easy to apply. The acceptance of a new analysis technique will be enhanced if its application assists in the decision-making process for future endeavors as well as discerning success of past efforts.

Stroking a golf ball into the hole on a flat putting green is a simple process to understand, but not always easy to accomplish. Golf putting shares common concepts with the treatment and analysis of astigmatism. When one is unsuccessful in hitting a ball along a chosen path into a hole, one of two events has happened: the force with which it was struck was either firm or too soft, or the direction in which it was propelled was either clockwise or counter-clockwise from that desired. A combination of these two is most common. The single most reliable parameter of the overall success of a putt is the length required for a second putt to place the ball in the hole.

The principle underlying the planning and analysis of astigmatism surgery is no more complicated than this. The intended path of the astigmatism surgery—that is, the required force and its direction, is the TIA (targeted induced astigmatism vector). The actual path taken by the astigmatism surgery is the SIA (surgically induced astigmatism vector) and the Difference Vector (DV) measures the force and its orientation still required to achieve the initial goal—effectively the second putt, using the above analogy. It is the various relationships between the SIA and TIA that tell us whether the treatment was on axis or off axis, or whether too much or too little force has been applied, and how to adjust for it. It is the magnitude of the DV, and its relationship with the TIA, that gauges the absolute and relative success of our surgery.

The Correction Index determined by the ratio of the SIA to the TIA is a measure of the amount of correction, and is optimally unity. It is greater than one if an over-correction has occurred and less than one if there has been an under-correction. The Coefficient of Adjustment is simply the inverse of the Correction Index, and quantifies the modification required to the initial surgery treatment plan to have achieved a Correction Index of one the desired correction.

The measures of success obtained utilizing this method of astigmatism analysis are both absolute and relative. The magnitude of the DV provides an absolute measure of the success achieved in astigmatism surgery, and is a measure of the second surgery; that is, the amount of steepening and its orientation, required to achieve the goal of the initial surgery. Using the golf analogy, the DV is represented by the second putt.

This vectorial comparison can be determined for all measurement modalities (R, K and T), and the DV's mean for a series of surgeries usefully compares astigmatism surgery techniques. The orientation of its DVs does not seem to provide useful information for the determination of success. The planning required for re-operation is best performed by freshly addressing the optimal refractive and topographic goals.

The relationship of the DV to the TIA is the Index of Success (IOS), which provides a relative measure of surgical success. The greater the targeted change in astigmatism, the smaller the IOS value would be for any constant value of the DV, hence the more successful was the surgery. Employing the golfing analogy, to determine which of two putts that finished equidistant from the hole was more effective, the answer is clearly the one that resulted from a longer first putt.

Where the achieved astigmatism coincides with the target, no astigmatism induction is required to achieve the initial goal. Just as one may one-putt a green, so in this case the DV is zero and so the Index of Success value is also zero.

Where smaller values of pre-operative astigmatism exist with consequently smaller targeted changes in astigmatism, less reliance can be placed on the measures that involve a ratio as the sole determinant in judging the success of surgery (IOS, Coefficient of Adjustment and Correction Index), because larger swings in values can be induced by smaller variations in the components of a fraction. Reference to means of absolute values such as the DV is necessary for comprehensive interpretation of results.

The TIA is the key enabling an analysis to be performed both at the corneal and spectacle plane. It has in effect removed the barrier that has until now prevented astigmatism surgeons who operated by refraction from appreciating the effect of surgery on the corneal shape and vice versa, by converting an intervening mirror barrier into a pane of glass; now each can see the effect of their surgery at the other's reference plane.

While current astigmatism analysis is adequate for determining what has happened (SIA), whether or not a change in the astigmatism was intended, until now analysis systems have not compared how what has happened differs from what was intended to happen. Comparing pre-operative and post-operative astigmatism values ignores any change in the astigmatism's axis and consequently is misleading, because it inevitably renders all imperfect corrections to be "under-corrections". It does not identify the separate errors of magnitude and axis.

For example, when analyzing the Angle of Error, a consistent error of 5° in a clockwise direction in all eyes may indicate a system error, such as beam rotation when performing excimer laser surgery. However, this 5° may be consistently clockwise in right eyes and counter-clockwise in left eyes, indicating the likely cause to be extortion of the eyes when lying supine.

2. The Optical Correction of Astigmatism

Refractive, Topographic and Residual Astigmatism

The optical correction of astigmatism measured refractively can be performed with spectacles, contact lenses or by surgery. Where the correction of astigmatism is performed by spectacles, then the subjective astigmatism is determined by manifest testing at the spectacle plane. This refractive astigmatism value provides a measure of the total net astigmatism of all the refracting surfaces of the eye. That is, the net astigmatic effect encountered by light during its passage through the optical system of the eye via the front and back surfaces of the cornea and lens, and the vitreal body. The subjective test will also be influenced by any tilt of the retina, and the conscious perception of this retinal image by the visual cortex of the occipital lobe.

The anterior surface of the cornea is the major refracting surface of the optical system of the eye. The variations between the values of the corneal astigmatism and the refractive astigmatism at the corneal plane is responsible for the residual astigmatism that cannot be eliminated from the optical system of the eye and its refractive correction. Until recently, these differences have been disregarded in the treatment of astigmatism; the consequence of this has significant implications for resultant corneal astigmatism.

The variance that occurs between topographic and refractive astigmatism cannot be dismissed, nor can residual astigmatism be loosely termed as "lenticular astigmatism". If this term were an adequate description for these differences, then one would expect corneal and refractive astigmatism to coincide both in magnitude and axis after cataract extraction and spheric lens implantation; however, this is not the case. The existence of two modalities for measuring astigmatism, subjective and objective, together with multiple measuring devices within each group, will ensure the perpetuation of these differences and the need to address them in the treatment.

Where refractive error is corrected by a soft contact lens, which provides only a spherical correction, then, in a theoretical model, a topographical image obtained from the front surface of the contact lens in place on the cornea would be equivalent to that image obtained of the cornea without the contact lens, and would provide a measure of topographical astigmatism. A manifest refraction, performed with or without this lens in place, provides a measure of refractive astigmatism at the spectacle plane.

Toric soft contact lenses are prescribed with the refractive astigmatism corrected for back vertex distance, at the appropriate axis. Where this contact lens is of the same refractive index as the cornea, and accurately situated on the cornea at the prescribed meridian, the CAVK (Computer Assisted Video Keratography) image obtained from the front surface of that lens as it lies on the cornea would, in a theoretical model, provide an image of the magnitude and axis of residual astigmatism of the eye. A manifest over-refraction should not detect any refractive astigmatic error.

A hard contact lens with spherical surfaces when in place on the cornea effectively sphericises the anterior refractive surface of the eye, so that the manifest over-refraction provides a measure of the amount of residual (not refractive) astigmatism. This over-refraction magnitude corrected to the cornea plane theoretically should be equal to the value obtained by CAVK on the surface of the in-situ toric soft contact lens, but the orientation of its refractive axis would be 90° to the orientation of the residual astigmatism.

3. Objective & Subjective Analysis

Corneal topography displayed by CAVK provides the treatment and analysis of astigmatism with objective and reproducible images. Analyzing an astigmatism result by topography as well as refraction will become an essential step in monitoring the changes at the surface where they are effected—on the cornea. CAVK provides us with an objective measure; however, some limitations are caused by the reduced definition of dioptric contour separation, present after non-incisional refractive surgery.

Manifest refraction is a subjective test that depends on observer and patient responses, which may vary according to testing conditions in a refracting lane such as lighting, chart distance and illumination inconsistencies. The inadequacy of refraction as the sole measurement parameter for astigmatism is accentuated by the large changes in spherical equivalents induced by refractive surgery, which may cause less attention than warranted to be paid to residual astigmatic refractive errors. The trends discernible by the objective measurements determined by corneal topography, or conventional keratometry, provide a balance for the subjective trends in the analyses. This additional information gives the required assurance necessary to determine the success of astigmatism surgery, the errors occurring and what adjustments are required to improve results.

Utilizing the TIA, the topographical and refractive targets are now determinable. The TIA provides the linkage to enable an analysis by refraction, topography or other device that measures astigmatism. The trend now emerging when performing laser astigmatism surgery is that significant differences exist in the results when comparing those achieved by refraction with those occurring on the cornea.

These differing trends in analyses may be attributable in part to undue emphasis on refraction as the sole treatment parameter.

4. Adjustments and Nomograms

The targeted change in corneal astigmatism (TIA) attempts to alter the pre-operative state to achieve the desired astigmatism goal as determined by all modalities; refraction, topography and keratometry. Nomograms are utilized for incisional astigmatism surgery (astigmatic keratotomy) to allow for the biological variance caused by such factors as age, ocular tension and corneal diameter. To achieve the targeted correction more consistently, adjustment factors can be determined to modify these incisional nomograms further or to fine-tune the performance of laser machines performing non-incisional surgery.

Analysis of PARK surgeries performed with the VisX twenty/twenty laser prior to February 1993, revealed a general trend of under-correction of astigmatism magnitude. Insufficient "force" was being applied, the average amounts of surgically induced astigmatism (SIA) being less than the average TIA intended, in a proportion of around 10 to 12. Subsequent results for magnitude achieved after April 1993, after applying an adjustment factor of 1.2 to the astigmatism requiring treatment, have shown that the SIA by refraction and topography subsequently more closely approximates the targeted change, achieving a correction index closer to one.

5. Computer-Assisted Video Keratography (CAVK)

The devices currently available for examining and measuring corneal contour fall broadly into two groups. The dioptric plots derive their data from reflective placido disc technology. The illuminated placido disc may be composed of either alternating black and white rings or a colored sequence of rings. The true elevation maps are derived from images generated by non-reflective images, either from scanning slits or the viewing of a projected grid by stereophotogrammetry. The latter technology enables non-axial viewing of non-reflective surfaces and the potential for providing a real-time image to be viewed on the operating table for intra-operative use.

The point of steepest curvature depicted at the highest peak of the bowtie on a dioptric plot-requires the least amount of tissue ablation to sphericize the cornea. The point of highest altitude depicted on a true elevation topography map requires the greatest amount of tissue ablation utilizing the excimer laser to sphericize the cornea. This corresponds to the meridian of flattest curvature and is aligned with the orientation of the steepening vector (the TIA). Tissue addition procedures such as astigmatic keratotomy act maximally, perpendicular to the axis of the TIA.

6. Keratoconus

Corneal astigmatism varies in the amount of asymmetry and non-orthogonal orientation. The spectrum of these physiological aberrations of corneal shape stretches from high amounts of astigmatism to the grosser amounts of asymmetry that appears as "forme fruste" and "early" or "subclinical" levels of keratoconus now more frequently identified with the aid of CAVK technology. The fine line that divides what lies within and outside the physiological spectrum may well be determined by clinical signs such as excessive corneal steepening, apical thinning or scarring. The differing patterns found in keratoconus may represent a continuum of different stages in the progression of the topographical alterations that occur over time in keratoconus. However, on careful examination of the topographical maps in eyes with the cornea showing keratoconus change, there commonly exists a vestigial remnant of one half of the bowtie, indicating the presence of both hemi-meridians of the astigmatism, even when in a grossly asymmetrical state.

7. Vector Analysis Value

Current methods of measurement of visual perception, such as visual acuity or contrast sensitivity, do not have the sensitivity required to demonstrate differing performance for alternative methods of astigmatism treatment. For example, heretofore, one was unable to demonstrate any discernible difference between the elliptical shaped ablation created by the opening of parallel blades limiting the beam aperture on two sides and the concurrent closing of a round diaphragm aperture, and sequential technique using the plano-cylindrical mode methods of treatment of astigmatism, when utilizing the VisX twenty/twenty excimer laser. This difference in performance was detectable when astigmatism change is separated from co-existing spherical changes by utilizing vector analysis.

8. Common Principle-Target T & R

There is an existing conflict in the two contrasting treatment paradigms that employ one of the two pre-operative astigmatism values, topography or refraction, as the determinant for their differing surgical treatment. This variance can be resolved by utilizing the orientation of the target corneal astigmatism as the guiding surgical paradigm, rather than either of the two pre-operative astigmatisms. In this way, all astigmatism surgeons, whether they use blade or laser technology, will be operating under the same guiding principle.

All forms of refractive surgery would then come under the one common principle of treatment; that is, to assess the effect of the proposed change in astigmatism on both refraction and corneal shape, in order to determine the optimal procedure for each individual eye. Current practice follows no common or consistent theme, totally emphasizing pre-operative corneal shape for cataract and penetrating keratoplasty, either shape or refraction for astigmatic keratotomy and refraction for excimer laser PARK surgery; each adopts only one or other extreme of the treatment spectrum.

It is only by determining the refractive and topographic targets prior to surgery that one can perform two essential tasks in the astigmatism surgery; firstly, to optimize the treatment according to prevailing parameters, and secondly, to enable a valid analysis by knowing where the targets lie. The process of setting precise goals enables measurement of success, determination of errors and making the various adjustments necessary to improve future procedures.

When performing excimer laser surgery for myopia and astigmatism, one may ask—if the goal is to eliminate the need for glasses, why would we not use the refraction as the only treatment parameter for both cylinder as well as the sphere? The answer lies in the targeting of a zero spherical equivalent for the correction of myopia, which takes care of the goal of eliminating spectacles. However, the penalty for sculpting the spectacle astigmatism onto the cornea is the maximizing of the resultant corneal astigmatism, and this is contrary to established and conventional principles of corneal surgery requiring that corneal shape be considered in surgical planning. The optical system of the eye that is independent of spectacle correction will continue to depend upon optimal regularity of the shape of the anterior cornea surface.

9. Optimal Treatment of Astigmatism

When differences prevail between topography and refraction, residual astigmatism unavoidably remains in the optical system of the eye, either in topography or refraction, or shared between the two leaving non-zero targets at both surfaces. The consequence of excluding topography from the surgical plan, as is widely practiced with Excimer laser surgery, is the inevitable destination of the residual astigmatism onto the cornea, the maximizing of the resultant corneal astigmatism and the potential for increased spherical aberration and resultant degradation of the perceived image.

The optimal treatment of astigmatism according to the invention is achieved when the sum of the targeted non-zero values of topographic and refractive astigmatism equals the minimum target value achievable for that optical system, and is appropriately apportioned to topography and refraction according to the orientation of the target astigmatism.

The orientation of the targeted corneal astigmatism optimally determines the amount of emphasis apportioned to topography and refraction in the surgical treatment plan. However, this apportionment may be directed according to how the cortical perception of the image degrades according to its orientation. If the image suffers maximal degradation, then in this case the goal of a spherical cornea would be preferable and the residual astigmatism would be directed to the refraction. Should the targeted astigmatism fall in the orientation where the image is minimally degraded, then any residual astigmatism optimally remains on the cornea, and no astigmatic correction remains in the refraction.

It may be demonstrable in a laboratory or clinical setting that oblique astigmatism may in fact be the least favorable option; if so, the treatment emphasis could be apportioned accordingly. The spherical equivalent of the eye that co-exists with the corneal astigmatism influences the clarity of the image according to the meridian at which it lies.

10. Emphasis

The emphasis is a measure, expressed as a percentage, of the relative position between the topographic and refractive goals when the treatment vector i.e. the TIA, terminates on a line in the double angle vector diagram connecting these two goals. Where the treatment emphasis line connects the two goals of zero topographic and refractive astigmatism, then the emphasis line coincides with the maximal correction target line, making possible the achievement of minimum target astigmatism by the maximal correction of existing astigmatism.

The greater the targeted corneal astigmatism is closer to 90° (WTR), the less the emphasis will be towards a zero topography goal as the sole treatment parameter.

However, the relative emphasis given to topography and refraction in the surgical plan may not bear a direct linear relationship according to the orientation of the target astigmatism (FIG. 19). Instead the surgeon must decide on the relative emphasis to be given to topography and refraction in the surgical plan, based on knowledge of the relative degradation of the visual image according to the orientation of the existing corneal astigmatism when the targeted spherical equivalent is zero. Current knowledge would suggest a WTR orientation to be the most favorable.

11. Complexities and Considerations of Corneal Shape

Traditionally, the primary concern of the cornea surgeon is the cornea shape; that is, the amount of astigmatism and its orientation. The optimal treatment of astigmatism would seek to achieve less corneal astigmatism, with an attempt to influence its orientation in a favorable orientation. Zero astigmatism by all measurement modalities is likely to continue to be the ultimate goal of the refractive surgeon.

Until now, conventional methods of astigmatism treatment have maintained zero astigmatism, when achievable, to be the surgical goal, whether the surgical method employed was based on shape or refractive astigmatism. The invention recognizes the inability to avoid non-zero goals imposed by prevailing differences that exist between refraction and topography. The introduction of the TIA enables any refractive or topographical goal to be reached in one surgical procedure, without requiring the intermediate step of attaining zero astigmatism. This is analogous to a flight to a destination not requiring a stop at the hub airport.

The expansion of the treatment parameters now possible, according to the invention, opens the way for determining new forms of astigmatism treatment not previously considered.

While in the past refraction has been the primary determinant of treatment, the introduction of topography into consideration has advantages; however, it also introduces complexities. The advantages gained are the reduction of targeted corneal astigmatism by the inclusion of shape parameters into the surgical plan, and the ability to use objective measurements for vectorial analysis of surgical results.

However, significant complexities are introduced by the inclusion of topography, which must be addressed. One complexity already discussed is the differences existing between the refraction, and the topography represented by the simulated K. The simulated K, better termed the "T", provided by CAVK is only a best-fit compromise, and is derived in different ways by different devices. In general, it is a mean value achieved over a number of measured constant reference points on both hemi-divisions of the cornea.

The existing differences in the dioptric magnitude of the astigmatism on the two hemi-meridians of the cornea are as prevalent as differences that exist between R and T values. The asymmetry of these hemi-meridian T values are further complicated by the non-orthogonal relationship of the two hemi-meridians of the astigmatism; that is, very frequently their axes are not aligned in a 180° orientation to each other. Current topography technologies occasionally vary in their determination of the orientation of the simulated K readings in the case of non-orthogonal astigmatism, by selecting at various readings on the same cornea one of three axes—either one of the two non-orthogonal values, or an orientation intersecting the two.

The differences between refraction and topography values cannot be dismissed as inconsequential. Nor should it be suggested that an accurate and methodical refraction can resolve these differences, as there is no mechanism to reconcile which hemi-meridian of the cornea topography has been resolved with the manifest refractive astigmatism value.

As stated above, examination of the corneal topography usually shows some amount of asymmetry in the two hemi-meridia of the cornea. This asymmetry may lie either in the magnitude or the non-orthogonal orientation of the two halves of the bow-tie. To accomplish the optimal treatment of the cornea, two resolutions of the common refractive and differing topographic magnitude and axis are required. One can determine a differing target corneal astigmatism from each half of the cornea, and from each of these can be determined an optimal TIA. This hemi-meridian solution for treatment is relevant to whatever incisional or non-incisional techniques are employed.

The refractive astigmatism frequently intersects the meridia of opposite non orthogonal topographic axes. Employing the optimal treatment for each hemi-division of the cornea can result in an enhanced synergistic effect in reducing targeted refractive astigmatism, yet attaining an overall more regular and closer to spherical cornea. Hence, treating each hemi-division more closely aligned to each topographic steep axis by recognizing the inevitable differences between the two topographic corneal halves, as well as each of their differences from the refractive astigmatic astigmatism, the optimal treatment according to the individual conditions prevailing for that patient can then be determined.

The regularizing of non-orthogonal and asymmetrical elements of corneal astigmatism, with or without a change in refractive astigmatism, could potentially improve the best-corrected as well as unaided visual acuity of an eye. This treatment could be applied by ablative or intrastromal lasers, incisional keratotomy or combinations of these technologies to improve the visual function of an eye without any change in its refractive status. It may be useful for the treatment of amblyopia ex anopsia in children, or in adult eyes that are functioning suboptimally with irregular astigmatism.

The treatment of irregular astigmatism to achieve an orthogonal symmetrical state can be achieved in a number of differing ways, depending on the goal of surgery. The achievement of regular orthogonal astigmatism can be performed without any change in refraction (FIGS. 25a–25c). The rotation of the less favorable cornea hemi-meridian towards the other more favorably placed half will achieve a concurrent favorable rotation of the refractive astigmatism (FIGS. 26a–26c). The disparity between topography and refraction can be reduced on one or both hemi-meridia by targeting in each the pre-operative refractive astigmatism. In this way, the net change in refractive astigmatism will equal the residual astigmatism of both topographical hemi-meridia (FIGS. 27a–27c).

The treatment of astigmatism may be directed at correcting existing aberrations of symmetry of corneal shape. In this manner, the clarity of the retinal image that has been degraded by the prevailing corneal irregularities could potentially be improved. One might anticipate that a significant proportion of eyes suffering visual obscuration may be likely to coexist with either non-orthogonal or asymmetrical astigmatism, or both. The correction of this aberrant state at any age by treatment of the cornea as two dissimilar halves could potentially improve the quality and quantity of vision perceived by that eye.

12. Astigmatic Torque

Where astigmatic torque is exerted on the pre-operative existing astigmatic state of the cornea, the force applied is at 45° to the existing astigmatism. A purely tangential (in double angle terms) uni-directional force applied to the steepest corneal axis will result in a target astigmatism that is greater in magnitude than the pre-operative value, with an orientation that has moved in the direction of the rotational force (FIGS. 21a, 21b).

The effect of applying this TIA force to change the corneal astigmatism will affect the refractive astigmatism. One would anticipate any change in the axis of the pre-existing corneal astigmatism would change the refractive astigmatism in the same clockwise or counter-clockwise orientation by the same TIA vector amount. This change in the amount or orientation of the refractive astigmatism (FIGS. 24a, 24b) may be favorable or unfavorable.

The division of treatment of the astigmatism of the eye into hemi-divisions would enable a change on the orientation of the two hemi-meridian corneal astigmatism, while reducing or eliminating any effect on refractive astigmatism. Two opposing steepening forces can be applied in opposite cyclical directions, negating each other's effect on refractive astigmatism. In this way, the use of opposing torsional forces can realign non-orthogonal asymmetrical hemi-meridians to achieve a coincident and therefore regular relationship (FIGS. 25a–25c). By changing the orientation of each in opposite directions, that is, clockwise and counter-clockwise, the net effect on refractive astigmatism can be reduced or eliminated. A closer relationship between the realigned topography and the refractive astigmatism would be anticipated.

The separation of flattening/steepening effects and clockwise or counter-clockwise torsional effects give control of the corneal shape by separating the changes into their component parts. If necessary, the linkage between refractive and topographic changes can in this way be simplified for analysis and therapy purposes.

However, applying the TIA to exert some proportion of astigmatic torque on the cornea without necessarily reducing the magnitude of the targeted corneal astigmatism achieves neither the maximal nor the optimal treatment of astigmatism of the eye. The maximal treatment of astigmatism occurs where the target astigmatism (topographic plus refractive) at its minimum value, equals the residual astigmatism of the eye. The treatment is optimal where this target astigmatism is distributed proportionately between topography and refraction, according to its orientation.

13. Qualitative Surgical Planning

The invention has stressed the importance of the quantitative information derived from CAVK, but necessarily recognizes the value of further qualitative information that can be derived by this quantitative planning and analysis technique. The method can be applied in a predictive manner, by applying the targeted change in astigmatism— either symmetrical or hemi-divisional, to the pre-operative astigmatism state, as displayed on the topographical map. The multiple individual measurements points, either singly or in groups, can have that treatment applied during the planning process to enable the viewing of the expected topographical picture that would be generated from that proposed treatment. A value for the target refractive astigmatism can also be determined in accordance with the resolution of the proposed treatment vectors.

The surgical planning can be fine-tuned according to the appearance of the topography as estimated by the calculated targeted change. Small changes in emphasis on either of the upper or lower treatment vectors (TIA) can modify the target appearance to that which is deemed most desirable according to the surgeon's qualitative criteria of a favorable result. These changes in emphasis of one or both TIAs will concurrently alter the target refractive astigmatism. It is worth noting that zero or close-to-zero refractive astigmatism can be achieved with asymmetric treatment vectors without necessarily either of these individually targeting zero refraction, while enabling some emphasis be given to both topography hemi-meridia to target less overall topographical astigmatism.

Further alternatives to fine-tuning the treatment by change in emphasis can be achieved by modifying the flattening/ steepening effect, the torque or a combination of these for either of the two treatment vectors. This can be performed under a real-time display of the intended topography which would result from any alteration of the treatment plan. Movement of the TIA in these modes away from the maximal correction target line would be performed only if maximal correction of astigmatism was not a priority.

14. Vector Change Maps

After surgery has been performed, the post-operative and the pre-operative topography maps can then be compared by examining the vectored change map in addition to performing simple arithmetic change or difference analysis at each point as is currently performed. This could he done for all relevant modalities of the vector analysis. For example, the correction index map would provide the relative areas of under and over-correction by the surgical laser or blade, and this could be expressed in terms of positive and negative amounts of magnitude of error. Absolute and relative areas of success can be mapped by the DV and Index of Success, and any variations in alignment or misalignment can be mapped by an Angle of Error map. The information generated by point-by-point vectored change can be used for individual or groups of patients to improve the performance of the refractive tool, whether it be laser or incisional.

In time, the current separate disciplines of CAVK and laser modulation of the corneal shape can merge as an integrated entity for the control and the evaluation of the surgical procedures where relative meridional changes in corneal shape are performed. The eventual coupling of these complementary and interdependent technologies can only synergistically enhance each of their individual values in the treatment and analysis of refractive errors.

15. Conclusion

The cornea is a transparent tissue whose function is affected by its shape. It consists of collagen and elastic tissue, which enables the induction of changes in shape by tissue ablation, incision and contraction. These relative steepening and flattening changes of the cornea occur as part of the concurrent general steepening or flattening spherical changes that occur in refractive surgery.

The planning of desired changes in toroidal shape to gain the maximum function requires the incorporation of measurement parameters for both modalities of topography (shape) and refraction (function). Recognizing and addressing the differences between not only the shape and the function, but also the two hemi-divisions of the shape, is an essential step on the path to realizing the maximum potential vision for an astigmatic eye.

The utilization of both subjective and objective parameters in the retrospective analysis further enhances the ability to fine-tune the devices employed to perform astigmatism surgery, by adjusting for any system inaccuracies. The laser machines of the future will need to address the requirement for asymmetrical as well as symmetrical treatments, to enable the modification of astigmatism on both sides of the cornea to either their chosen configuration or the optimal levels. Establishing the orthogonal symmetrical state will create regularity of topographic astigmatism, potentially improving the quality of the perceived image on the retina.

This invention has sought to extend the methodology of astigmatism analysis to gain predictive value in surgical planning and treatment. The incorporation of topography into the surgical plan provides the immediate benefit of reduced corneal astigmatism. However, complexity is introduced into the surgical decision-making process by the need to address the differences of symmetry in the two halves of the cornea, in addition to the differences between topography and refraction. The method detailed in this paper for determining the optimal treatment of astigmatism is guided by the targeted, not the preoperative astigmatism and can be applied separately to both halves of the cornea. This methodology provides a blueprint for the control of any desired change in the corneal shape. Furthermore, it presents a means for ultimately achieving the integration of diagnostic, analytic and therapeutic refractive surgery tools.

What is claimed is:

1. An article encoded with a computer readable program for operating a computer to obtain parameters related to a surgical procedure to correct astigmatism in the eye of a patient, said program being provided with magnitude and angle values of astigmatism measured topographically and determined refractively, and said program determining said surgical parameters based on the measurements of astigmatism both refractively and topographically by carrying out the operation comprising the steps of:

a) summating the values of astigmatism measured topographically on the values of astigmatism measured refractively, on the one hand, and the values of astigmatism measured refractively on the values of astigmatism measured topographically, on the other hand, to obtain respective non-zero target astigmatism values for refraction and topography, and b) establishing said surgical parameters based on both said target astigmatism values such that the sum of the target astigmatism values for refraction and topography is a minimum, whereby astigmatism in the eye following surgery based on said parameters will be a minimum when measured topographically and refractively.

2. The article with the program as claimed in claim 1, wherein magnitude and axis of astigmatism values obtained from refraction and topography measurements respectively are plotted on a double angle vector diagram to determine said parameters.

3. The article with the program as claimed in claim 2, wherein said target astigmatism values for the refractive and topographical measurements are calculated as vectors which lie on a straight line on said double angle vector diagram.

4. The article with the program as claimed in claim 2, further comprising the steps of apportioning said target astigmatism values between topographic and refractive measurements based on orientation of the respective target astigmatism values.

5. The article with the program as claimed in claim 4, wherein said apportioning of said target astigmatism values is based on orientation of the respective target astigmatism values relative to a "with the rule" orientation.

6. The article with the program as claimed in claim 1, wherein for an eye having a non-symmetrical topography of the cornea of the eye, said program further comprises the following steps:

considering the cornea as divided into two hemi-divisions, and determining said surgical parameters for each hemi-division independently of one another.

7. The article with the program as claimed in claim 6, wherein said program further comprises the steps of obtaining resolved treatment parameters for the entire eye based on the parameters for each hemi-division.

8. The article with the program as claimed in claim 1, wherein said program further comprises the steps of applying said parameters for surgical treatment which will alter the axis of astigmatism of the eye measured topographically or refractively without substantially altering the magnitude of said astigmatism.

9. The article with the program as claimed in claim 8, wherein said surgical parameters to alter the axis of astigmatism without altering the magnitude are obtained by said program which carries out the steps comprising applying a force to the cornea at an angle offset from 45° relative to the axis of astigmatism.

10. The article with the program as claimed in claim 9, in which the axis of astigmatism is altered as a function of the applied force.

11. The article with the program as claimed in claim 10, in which for altering the axis of astigmatism without altering the magnitude, said force is offset from said axis by an angle of 45° to include a component to flatten or steepen the cornea in the direction of said force to compensate a corresponding flattening or steepening produced by the component of said force resolved at said 45° angle.

12. The article with the program as claimed in claim 6, in which said surgical parameters include a force at an angle of 45° to act as a torque force to alter the axis of astigmatism and increase the magnitude of astigmatism.

13. The article with the program as claimed in claim 6, in which conditions in which topographic measurements in the hemi-divisions do not coincide in magnitude or axis or both, the program carries out steps further comprising effecting surgical treatment in equal magnitude and at 180° in the hemi-divisions to produce no net effect on refractive astigmatism while sculpting the cornea in said hemi-divisions to equalize the shape thereof.

14. The article with the program as claimed in claim 6, wherein for irregular astigmatism in which topographic measurements in the hemi-divisions do not coincide in magnitude and axis, the program further comprises the steps of correcting the astigmatism to an orthogonal symmetrical state.

15. The article with the program as claimed in claim 14, wherein the treatment is effected in only one hemi-division.

16. The article with the program as claimed in claim 15, wherein said correcting of the astigmatism is effected in said one hemi-division which is the more astigmatic to bring said one hemi-division into orthogonal symmetrical coincidence with the other hemi-division.

17. The article with the program as claimed in claim 15, further comprising the steps of determining which axis of the measured astigmatism in the hemi-divisions is closer to a "with the rule" orientation and directing a change in the orientation of the axis of the astigmatism of the other of the hemi-divisions by surgical intervention to move said axis in said other hemi-division in the direction of coincidence with the axis of the hemi-division closer to the "with the rule" orientation.

18. The article with the program as claimed in claim 17, wherein said surgical direction of the intervention comprises calculating a target induced astigmatism force to be applied in said other hemi-division.

19. The article with the program as claimed in claim 1, wherein said summating of the values of astigmatism comprises vectorially subtracting the values of magnitude and axis measured refractively and topographically to obtain a vector equal to the sum of said non-zero target astigmatism values for refraction and topography.

20. The article with the program as claimed in claim 19, comprising effecting the vectorial subtracting of the astigmatism values measured topographically and refractively on a double angle vector diagram.

21. The article with the program as claimed in claim 19, wherein the establishing of said surgical parameters comprises selecting a target induced astigmatism vector intermediate said values of astigmatism measured topographically and refractively to yield said respective non-zero target astigmatism values for refraction and topography.

22. An article encoded with a computer readable program for operating a computer to obtain parameters related to a surgical procedure to correct astigmatism in the eye of a patient, said program being provided with magnitude and angle values of astigmatism measured topographically on the cornea of the eye and determined refractively by the steps comprising:

determining said surgical parameters based on the measurements of astigmatism both refractively and topographically, a) summating the values of astigmatism measured topographically on the values of astigmatism measured refractively, on the one hand, and the values of astigmatism measured refractively on the values of astigmatism measured topographically, on the other hand, to obtain respective non-zero target astigmatism values for refraction and topography, b) establishing said surgical parameters based on both said target astigmatism values, and c) considering the cornea as divided into two hemi-divisions and determining said parameters for each hemi-division independently of one another.

23. The article with the program as claimed in claim 22, wherein the program carries out the steps further comprising targeting values of refractive magnitude and axis in each hemi-division to achieve orthogonal symmetrical astigmatism of the two hemi-divisions and thereby shifting refractive astigmatism to achieve equal residual astigmatisms in both hemi-divisions at minimum levels.

24. The article with the program as claimed in claim 22, wherein the program carries out the steps further comprising targeting values of topographical magnitude and axis in each hemi-division to achieve orthogonal symmetrical astigmatism with no change in the values of magnitude and axis of astigmatism measured refractively.

25. The article with the program as claimed in claim 24, wherein the program carries out the steps further comprising equalizing the magnitude of the parameters applied in the two hemi-divisions and placing said parameters at 90° to one another for carrying out a surgical procedure.

26. The article with the program as claimed in claim 22, wherein the program carries out the steps further comprising targeting values of topographical magnitude and axis in each hemi-division to achieve orthogonal symmetrical astigmatism following surgery with an axis of astigmatism shifted towards a "with the rule" orientation.

27. The article with the program as claimed in claim 22, wherein the program carries out the steps further comprising targeting equal values of magnitude of astigmatism in said two hemi-divisions topographically at 180° relative to one another and at respective axes in said hemi-divisions to achieve, following surgery, orthogonal symmetrical astigmatism with minimum values of residual astigmatism.

28. The article with the program as claimed in claim 22, wherein the program carries out the steps further comprising targeting equal values of magnitude for astigmatism in said two hemi-divisions topographically at 180° relative to one another and at respective axes in said hemi-divisions to achieve, following surgery, orthogonal symmetrical astigmatism with astigmatic orientation at a predetermined axis.

29. The article with the program as claimed in claim 22, wherein the program carries out the steps further comprising applying surgical parameters with targeted topographic magnitudes and axes in the two hemi-divisions which are different from one another to achieve in said hemi-divisions a determined corneal astigmatism.

30. An article encoded with a computer readable program for operating a computer to obtain parameters related to a surgical procedure to correct astigmatism in the eye of a patient, said program being provided with magnitude and angle values of astigmatism measured topographically and determined refractively, said program providing said parameters related to a surgical procedure by the steps comprising:

combining the measured values of astigmatism based on topography and refraction to obtain said surgical parameters which will produce a minimum resultant astigmatism measured topographically and refractively, or a determined shift of the axis of the astigmatism or orthogonal symmetry of the eye.

* * * * *